US011851651B2

(12) United States Patent
Banal et al.

(10) Patent No.: US 11,851,651 B2
(45) Date of Patent: Dec. 26, 2023

(54) AUTOMATED METHODS FOR SCALABLE, PARALLELIZED ENZYMATIC BIOPOLYMER SYNTHESIS AND MODIFICATION USING MICROFLUIDIC DEVICES

(71) Applicant: Massachusetts Institute of Technology, Cambridge, MA (US)

(72) Inventors: James Banal, Cambridge, MA (US); Joseph Don Berleant, Cambridge, MA (US); Tyson Shepherd, Arlington, MA (US); Mark Bathe, Cambridge, MA (US)

(73) Assignee: MASSACHUSETTS INSTITUTE OF TECHNOLOGY, Cambridge, MA (US)

( * ) Notice: Subject to any disclaimer, the term of this patent is extended or adjusted under 35 U.S.C. 154(b) by 494 days.

(21) Appl. No.: 16/012,583

(22) Filed: Jun. 19, 2018

(65) Prior Publication Data
US 2018/0362969 A1 Dec. 20, 2018

Related U.S. Application Data

(60) Provisional application No. 62/521,612, filed on Jun. 19, 2017.

(51) Int. Cl.
*B01L 9/00* (2006.01)
*C12N 15/10* (2006.01)
*G16B 35/00* (2019.01)
*G16C 20/60* (2019.01)
*C12P 19/34* (2006.01)
*B01J 19/00* (2006.01)
*B01L 3/00* (2006.01)
*C12Q 1/6811* (2018.01)
*G16B 40/00* (2019.01)

(52) U.S. Cl.
CPC ...... *C12N 15/1068* (2013.01); *B01J 19/0046* (2013.01); *C12P 19/34* (2013.01); *G16B 35/00* (2019.02); *G16C 20/60* (2019.02); *B01J 2219/0065* (2013.01); *B01J 2219/00675* (2013.01); *B01J 2219/00722* (2013.01); *B01J 2219/00725* (2013.01); *B01J 2219/00729* (2013.01); *B01L 3/502784* (2013.01); *B01L 3/502792* (2013.01); *B01L 2400/0427* (2013.01); *C12N 15/1093* (2013.01); *C12Q 1/6811* (2013.01); *C12Q 2565/629* (2013.01); *G16B 40/00* (2019.02)

(58) Field of Classification Search
CPC ............ G01N 35/08; G01N 2035/1034
USPC .............................. 436/53; 422/82
See application file for complete search history.

(56) References Cited

U.S. PATENT DOCUMENTS

| | | | |
|---|---|---|---|
| 4,816,567 A | 3/1989 | Cabilly |
| 5,091,652 A | 2/1992 | Mathies |
| 5,445,934 A | 8/1995 | Fodor |
| 5,624,821 A | 4/1997 | Winter |
| 6,194,551 B1 | 2/2001 | Idusogie |
| 8,071,755 B2 | 12/2011 | Efcavitch |
| 8,304,253 B2 | 11/2012 | Yi |
| 8,459,295 B2 | 6/2013 | Kim |
| 8,808,989 B1 | 8/2014 | Efcavitch |
| 8,834,695 B2 | 9/2014 | Wang |
| 8,883,014 B2 | 11/2014 | Nelson |
| 9,005,544 B2 | 4/2015 | Van Dam |
| 9,169,573 B2 | 10/2015 | Hadwen |
| 9,266,076 B2 | 2/2016 | Kim |
| 9,539,573 B1 | 1/2017 | Hadwen |
| 9,808,800 B2 | 11/2017 | Chen |
| 2003/0013880 A1 | 1/2003 | Murthy |

(Continued)

FOREIGN PATENT DOCUMENTS

WO 1999/058572 11/1999
WO 9958572 11/1999

(Continued)

OTHER PUBLICATIONS

Biebricher, et al., "Template-free generation of RNA species that replicate with bacteriophage T7 RNA polymerase," *EMBO J*, 15(13): 3458-3465 (1996).
Bornholt, et al., "Toward a DNA-Based Archival Storage System," *IEEE Micro*, 37 (3): 98-104 (2017).
Braasch, et al., "Locked nucleic acid (LNA): fine-tuning the recognition of DNA and RNA," *Chem. Biol.* 8(1):1-7 (2001).
Cho, et al., "An unnatural biopolymer," *Science*, 261, 1303-1305 (1993).

(Continued)

*Primary Examiner* — Natalia Levkovich
(74) *Attorney, Agent, or Firm* — PABST PATENT GROUP LLP

(57) ABSTRACT

Methods for the automated template-free synthesis of user-defined sequence controlled biopolymers using microfluidic devices are described. The methods facilitate simultaneous synthesis of up to thousands of uniquely addressed biopolymers from the controlled movement and combination of regents as fluid droplets using microfluidic and EWOD-based systems. In some forms, biopolymers including nucleic acids, peptides, carbohydrates, and lipids are synthesized from step-wise assembly of building blocks based on a user-defined sequence of droplet movements. In some forms, the methods synthesize uniquely addressed nucleic acids of up to 1,000 nucleotides in length. Methods for adding, removing and changing barcodes on biopolymers are also provided. Biopolymers synthesized according to the methods, and libraries and databases thereof are also described. Modified biopolymers, including chemically modified nucleotides and biopolymers conjugated to other molecules are described.

43 Claims, 2 Drawing Sheets

Specification includes a Sequence Listing.

(56) References Cited

U.S. PATENT DOCUMENTS

| | | | |
|---|---|---|---|
| 2007/0117102 A1 | 5/2007 | Buzby | |
| 2008/0053205 A1* | 3/2008 | Pollack | G01N 27/44717 73/61.71 |
| 2009/0186771 A1 | 7/2009 | Siddiqi | |
| 2011/0081647 A1 | 4/2011 | Siddiqi | |
| 2011/0217738 A1 | 9/2011 | Jacobson | |
| 2013/0189743 A1 | 7/2013 | Balasubramanian | |
| 2016/0108382 A1 | 4/2016 | Efcavitch | |
| 2017/0326524 A1 | 11/2017 | Hadwen | |

FOREIGN PATENT DOCUMENTS

| | | |
|---|---|---|
| WO | 2006/005880 | 1/2006 |
| WO | 2006005880 | 1/2006 |
| WO | 2013/102011 | 7/2013 |
| WO | 2013102011 | 7/2013 |
| WO | 2015/063767 | 5/2015 |
| WO | 2015063767 | 5/2015 |
| WO | 2016/111251 | 7/2016 |
| WO | 2016111251 | 7/2016 |
| WO | 2017/189914 | 11/2017 |
| WO | 2017189914 | 11/2017 |

OTHER PUBLICATIONS

Drmanac, et al., "Sequencing by hybridization: towards an automated sequencing of one million M13 clones arrayed on membranes," *Electrophoresis*, 13(8):566-73 (1992).

Gellman, "Foldamers: A Manifesto," *SH. Acc. Chem. Res.*, 31, 173-180 (1998).

Goldman, et al., "Towards practical, high-capacity, low-maintenance information storage in synthesized DNA," *Nature*, 494(7435): 77-80 (2013).

Gong, et al., "All-electronic droplet generation on-chip with real-time feedback control for EWOD digital microfluidics," *Lab Chip*.; 8(6): 898-906 (2008).

Gruber, et al., "Efficient tumor cell lysis mediated by a bispecific single chain antibody expressed in *Escherichia coli*," *J. Immunol.*, 152(11):5368-74 (1994).

Hollinger, et al., "Diabodies: small bivalent and bispecific antibody fragments," *Proc. Natl. Acad. Sci. U.S.A.*, 90:6444-48 (1993).

Kurreck, et al., "Design of antisense oligonucleotides stabilized by locked nucleic acids," *Nucleic Acids Res.* 30(9): 1911-1918 (2002).

Lin, et al., "Applications of EWOD Systems for DNA Reaction and Analysis," *Journal of Adhesion Science and Technology*, 26 (12-17): 1789-1804 (2012).

Lue, et al., "Telomerase can act as a template- and RNA-independent terminal transferase," *PNAS*. 102(28): 9778-9783 (2005).

Morrison, et al., "Chimeric human antibody molecules: mouse antigen-binding domains with human constant region domains," *Proc. Natl. Acad. Sci. USA*, 81: 6851-6855 (1984).

Organick, et al., "Random access in large-scale DNA data storage," *Nature Biotechnology*, 36(3): 242-248 (2018).

Paunescu, et al., "Reversible DNA encapsulation in silica to produce ROS-resistant and heat-resistant synthetic DNA 'fossils'," *Nature Protocols*, 8(12): 2440-2448 (2013).

Pease, et al., "Light-generated oligonucleotide arrays for rapid DNA sequence analysis,", *Proc. Natl. Acad. Sci.*, 91(11): 5022-5026 (1994).

Rouillard, et al., "OligoArray 2.0: design of oligonucleotide probes for DNA microarrays using a thermodynamic approach," *Nucleic Acids Res* 31:3057-3062 (2003).

Shin, et al., "Decoding neural transcriptomes and epigenomes via high-throughput sequencing", *Nature Neuroscience*, 17: 1463-1475 (2014).

Songsivilai, et al., "Bispecific antibody: a tool for diagnosis and treatment of disease", *Clin. Exp. Immunol.*, 79:315-321 (1990).

Stimpson, et al., "Real-time detection of DNA hybridization and melting on oligonucleotide arrays by using optical wave guides," *Proc. Natl. Acad. Sci. USA* 92:6379-6383 (1995).

Wahlestedt, et al., "Potent and nontoxic antisense oligonucleotides containing locked nucleic acids," *Proc. Natl Acad. Sci. USA*, 97(10): 5633-5638 (2000).

Wang, et al., "Selection of oligonucleotide probes for protein coding sequences," *Bioinformatics*, 19(7):796-802 (2003).

Xu, et al., "Design of 240,000 orthogonal 25mer DNA barcode probes," *Proc. Natl. Acad. Sci.*, 106 (7):2289-2294 (2009).

Yershov, et al., "DNA analysis and diagnostics on oligonucleotide microchips," *Proc. Natl. Aca. Sci.*, 93:4913 (1996).

Zhirnov, et al., "Nucleic acid memory," *Nature Materials*, 15(4): 366-370 (2016).

Biebricher, et al., "Template-free generation of RNA species that replicate with bacteriophage T7 RNA polymerase", EMBO J, 15(13): 3458-65 (1996).

Bornholt, et al., "Toward a DNA-Based Archival Storage System", IEEE Micro 37 (3); pp. 98-104 (2017).

Braasch, et al., "Locked nucleic acid (LNA): Fine-tuning the recognition of DNA and RNA", Chem. Biol. 81-7 (2001).

Caruthers "Deoxynucleoside phosphoramidites—A new class of key intermediates for deoxypolynucleotide synthesis," Tetrahedron Letters, 22(20): 1859-1862 (1981).

Cho, et al., "An unnatural biopolymer", Science, 261:1303-5 (1993).

Choi, et al., "Digital microfluidics", Annu. Rev. Anal. Chem. 5:413-40 (2012).

Church, et al., "Next-generation digital information storage in DNA", Science; 337 (6102):1628 (2012).

Drmanac, et al., "Sequencing by hybridization: towards an automated sequencing of one million M13 clones arrayed on membranes", Electrophoresis, 13:566 (1992).

Fair, "Parallel processing of multifunctional, point-of-care bio-applications on electrowetting cips", Department of Electrical and Computer Engineering, Annals of 14th International Conference on Miniaturized Systems for Chemistry and Life Sciences, 2095-2097 (2010).

Gellman, "Foldamers: A Manifesto", Acc. Chem. Res., 31:173-80 (1998).

Goldman, et al., "Towards practical, high-capacity, low-maintenance information storage in synthesized DNA", Nature, 494:77-80 (2013).

Goodman, "Error-prone repair DNA polymerases in prokaryotes and eukaryotes", Annu Rev Biochem. 71:17-50 (2002).

Gruber, et al., "Efficient tumor cell lysis mediated by a bispecific single chain antibody expressed in *Escherichia coli*", J. Immunol., 152:5368 (1994).

Guo et al., "Direct fluorescence analysis of genetic polymorphisms by hybridization with oligonucleotide arrays on glass supports", Nucleic acids Res. 22:5456-5465 (1994).

Hensley, "SOMAmers and SOMAscan—A Protein Biomarker Discovery Platform for Rapid Analysis of Sample Collections From Bench Top to the Clinic," Journal of Biomolecular Techniques: JBT. 24 (Suppl) S5 (2013).

Hollinger, et al., ""Diabodies": small bivalent and bispecific antibody fragments", PNAS, 90:6444-48 (1993).

Hu, et al. "Selection of long oligonucleotides for gene expression microarrays using weighted rank-sum strategy", BMC Bioinformatics 8:350 (2007).

Hughes, et al., "Expression profiling using microarrays fabricated by an ink-jet oligonucleotide synthesizer", Nature Biotechnology, 19:342:347 (2001).

International Search Report for PCT/US2018/038311 dated Jan. 30, 2019.

Jebrail, et al., "Combinatorial Synthesis of Peptidomimetics Using Digital Microfluidics", Journal of Flow Chemistry, 2(3): 103-107 (2012).

Kosuri, "Large-scale de novo DNA synthesis: technologies and applications", Nature Methods, 11(5):499:507(2014).

Kurreck, et al., "Design of antisense oligonucleotides stabilized by locked nucleic acids", Nucleic Acids Res. 301911-1918 (2002).

Lee et al., "Electrowetting and electrowetting-on-dielectric for microscale liquid handling," Sensors and Actuators A: Physical, 95(2-3): 259-268 (2002).

Lin, et al., J Adhesion Sci Tech, 26 (12-17): pp. 1789-1804; PMCID: PMC4770201 (2012).

(56) References Cited

OTHER PUBLICATIONS

Lue, et al., "elomerase can act as a template- and RNA-independent terminal transferase", PNAS. 102 (28) 9778-9783 (2005).

Markham, et al., "UNAFold: software for nucleic acid folding and hybridization", Methods Mol Biol 453:3-31 (2008).

Mathews, et al., "Photo-cleavable nucleotides for primer free enzyme mediated DNA synthesis," Org Biomol Chem. 14(35): 8278-88 (2016).

Morrison, et al., "Chimeric human antibody molecules: mouse antigen-binding domains with human constant region domains", PNAS, 81: 6851-6855 (1984).

Motea, et al., "Terminal deoxynucleotidyl transferase: the story of a misguided DNA polymerase," Biochimica et Biophysica Acta, 1804(5): 1151-1166 (2010).

Nielsen et al., "Design of oligonucleotides for microarrays and perspectives for design of multi-transcriptome arrays", Nucleic Acids Res 31:3491-3496 (2003).

Organick, et al., "Random access in large-scale DNA data storage", Nature Biotechnology, 36:242-8 (2018).

Paunescu, et al., "Reversible DNA encapsulation in silica to produce ROS-resistant and heat-resistant synthetic DNA fossils", Nature Protocols, 8:2440-8 (2013).

Pease, et al., "Light-generated oligonucleotide arrays for rapid DNA sequence analysis", PNAS, 91(11):5022-5026 (1994).

Rouillard, et al., "OligoArray 2.0: design of oligonucleotide probes for DNA microarrays using a thermodynamic approach", Nucleic Acids Res 31:3057-62 (2003).

Shin, et al., "Decoding neural transcriptomes and epigenomes via high-throughput sequencing", Nature Neuroscience 17, 1463-75 (2014).

Songsivilai et al., "Bispecific antibody: a tool for diagnosis and treatment of disease", Clin. Exp. Immunol., 79:315-21 (1990).

Stimpson, et al., "Real-time detection of DNA hybridization and melting on oligonucleotide arrays by using optical wave guides", PNAS, 92:6379-83 (1995).

Wahlestedt, et al., "Potent and nontoxic antisense oligonucleotides containing locked nucleic acids", PNAS, 97:5633-8 (2000).

Wang, et al., "Selection of oligonucleotide probes for protein coding sequences", Bioinformatics 19:796-802 (2003).

Xu, et al., "Design of 240,000 orthogonal 25mer DNA barcode probes", PNAS, 106 (7): 2289-94 (2009).

Yazdi, et al., "A Rewritable, Random-Access DNA-Based Storage System", Scientific Reports. V.5, Article No. 14138 (2015).

Yershov, et al., "DNA analysis and diagnostics on oligonucleotide microchips", PNAS. 93:4913 (1996).

Zhirnov, et al., "Nucleic acid memory", Nature Materials, V.15, pp. 366-370 (2016).

Zyrina, et al., "Ab initio synthesis by DNA polymerases", FEMS Microbiology Letters, 351(1):1-6 (2013).

* cited by examiner

SEQUENCE LISTING

<160> NUMBER OF SEQ ID NOS: 25

<210> SEQ ID NO 1
<211> LENGTH: 25
<212> TYPE: DNA
<213> ORGANISM: Artificial Sequence
<220> FEATURE:
<223> OTHER INFORMATION: Synthetic Sequence

<400> SEQUENCE: 1
cggcccatct ggtgtgatgc attac                25

<210> SEQ ID NO 2
<211> LENGTH: 25
<212> TYPE: DNA
<213> ORGANISM: Artificial Sequence
<220> FEATURE:
<223> OTHER INFORMATION: Synthetic Sequence

<400> SEQUENCE: 2
cggcccatct ggtgtgatgc agtac                25

<210> SEQ ID NO 3

```
<211> LENGTH: 25
<212> TYPE: DNA
<213> ORGANISM: Artificial Sequence
<220> FEATURE:
<223> OTHER INFORMATION: Synthetic Sequence

<400> SEQUENCE: 3
cggcccaact ggtgtgatgc agtac                                    25

<210> SEQ ID NO 4
<211> LENGTH: 25
<212> TYPE: DNA
<213> ORGANISM: Artificial Sequence
<220> FEATURE:
<223> OTHER INFORMATION: Synthetic Sequence

<400> SEQUENCE: 4
cggcccaact ggtgtcatgc agtac                                    25

<210> SEQ ID NO 5
<211> LENGTH: 25
<212> TYPE: DNA
<213> ORGANISM: Artificial Sequence
<220> FEATURE:
<223> OTHER INFORMATION: Synthetic Sequence

<400> SEQUENCE: 5
cggtccaact ggtgtcatgc agtac                                    25

<210> SEQ ID NO 6
<211> LENGTH: 25
<212> TYPE: DNA
<213> ORGANISM: Artificial Sequence
<220> FEATURE:
<223> OTHER INFORMATION: Synthetic Sequence

<400> SEQUENCE: 6
cggtccaact ggtgtcaggc agtac                                    25

<210> SEQ ID NO 7
<211> LENGTH: 25
<212> TYPE: DNA
<213> ORGANISM: Artificial Sequence
<220> FEATURE:
<223> OTHER INFORMATION: Synthetic Sequence

<400> SEQUENCE: 7
cggtcaaact ggtgtcaggc agtac                                    25

<210> SEQ ID NO 8
<211> LENGTH: 25
<212> TYPE: DNA
<213> ORGANISM: Artificial Sequence
<220> FEATURE:
<223> OTHER INFORMATION: Synthetic Sequence

<400> SEQUENCE: 8
cagtcaaact ggtgtcaggc agtac                                    25

<210> SEQ ID NO 9
<211> LENGTH: 25
<212> TYPE: DNA
<213> ORGANISM: Artificial Sequence
<220> FEATURE:
<223> OTHER INFORMATION: Synthetic Sequence
```

<400> SEQUENCE: 9
cagtcaaact ggtctcaggc agtac                                              25

<210> SEQ ID NO 10
<211> LENGTH: 25
<212> TYPE: DNA
<213> ORGANISM: Artificial Sequence
<220> FEATURE:
<223> OTHER INFORMATION: Synthetic Sequence

<400> SEQUENCE: 10
cagtcaaaca ggtctcaggc agtac                                              25

<210> SEQ ID NO 11
<211> LENGTH: 25
<212> TYPE: DNA
<213> ORGANISM: Artificial Sequence
<220> FEATURE:
<223> OTHER INFORMATION: Synthetic Sequence

<400> SEQUENCE: 11
cagtcaaaca gttctcaggc agtac                                              25

<210> SEQ ID NO 12
<211> LENGTH: 25
<212> TYPE: DNA
<213> ORGANISM: Artificial Sequence
<220> FEATURE:
<223> OTHER INFORMATION: Synthetic Sequence

<400> SEQUENCE: 12
ggccagatta tatgagcgtc tcctt                                              25

<210> SEQ ID NO 13
<211> LENGTH: 25
<212> TYPE: DNA
<213> ORGANISM: Artificial Sequence
<220> FEATURE:
<223> OTHER INFORMATION: Synthetic Sequence

<400> SEQUENCE: 13
ggccagatta tatgaacgtc tcctt                                              25

<210> SEQ ID NO 14
<211> LENGTH: 25
<212> TYPE: DNA
<213> ORGANISM: Artificial Sequence
<220> FEATURE:
<223> OTHER INFORMATION: Synthetic Sequence

<400> SEQUENCE: 14
ggccacatta tatgaacgtc tcctt                                              25

<210> SEQ ID NO 15
<211> LENGTH: 25
<212> TYPE: DNA
<213> ORGANISM: Artificial Sequence
<220> FEATURE:
<223> OTHER INFORMATION: Synthetic Sequence

<400> SEQUENCE: 15
ggccacatta gatgaacgtc tcctt                                              25

<210> SEQ ID NO 16

```
<211> LENGTH: 25
<212> TYPE: DNA
<213> ORGANISM: Artificial Sequence
<220> FEATURE:
<223> OTHER INFORMATION: Synthetic Sequence

<400> SEQUENCE: 16
ggccacatta gatgaacctc tcctt                                              25

<210> SEQ ID NO 17
<211> LENGTH: 25
<212> TYPE: DNA
<213> ORGANISM: Artificial Sequence
<220> FEATURE:
<223> OTHER INFORMATION: Synthetic Sequence

<400> SEQUENCE: 17
ggcaacatta gatgaacctc tcctt                                              25

<210> SEQ ID NO 18
<211> LENGTH: 25
<212> TYPE: DNA
<213> ORGANISM: Artificial Sequence
<220> FEATURE:
<223> OTHER INFORMATION: Synthetic Sequence

<400> SEQUENCE: 18
ggcaacatta gatgaacctg tcctt                                              25

<210> SEQ ID NO 19
<211> LENGTH: 25
<212> TYPE: DNA
<213> ORGANISM: Artificial Sequence
<220> FEATURE:
<223> OTHER INFORMATION: Synthetic Sequence

<400> SEQUENCE: 19
ggcaacatga gatgaacctg tcctt                                              25

<210> SEQ ID NO 20
<211> LENGTH: 25
<212> TYPE: DNA
<213> ORGANISM: Artificial Sequence
<220> FEATURE:
<223> OTHER INFORMATION: Synthetic Sequence

<400> SEQUENCE: 20
gtcaacatga gatgaacctg tcctt                                              25

<210> SEQ ID NO 21
<211> LENGTH: 25
<212> TYPE: DNA
<213> ORGANISM: Artificial Sequence
<220> FEATURE:
<223> OTHER INFORMATION: Synthetic Sequence

<400> SEQUENCE: 21
gtcaacatga gatcaacctg tcctt                                              25

<210> SEQ ID NO 22
<211> LENGTH: 19
<212> TYPE: DNA
<213> ORGANISM: Artificial Sequence
<220> FEATURE:
<223> OTHER INFORMATION: Synthetic Sequence
```

```
<400> SEQUENCE: 22
gtcgtcgtcc cctcaaact                                                     19

<210> SEQ ID NO 23
<211> LENGTH: 18
<212> TYPE: DNA
<213> ORGANISM: Artificial Sequence
<220> FEATURE:
<223> OTHER INFORMATION: Synthetic Sequence

<400> SEQUENCE: 23
taatacgact cactatag                                                      18

<210> SEQ ID NO 24
<211> LENGTH: 45
<212> TYPE: DNA
<213> ORGANISM: Artificial Sequence
<220> FEATURE:
<223> OTHER INFORMATION: Synthetic Sequence

<400> SEQUENCE: 24
atctctctct tttcctcctc ctccgttgtt gttgttgaga gagat                        45

<210> SEQ ID NO 25
<211> LENGTH: 11
<212> TYPE: DNA
<213> ORGANISM: Artificial Sequence
<220> FEATURE:
<223> OTHER INFORMATION: Synthetic Sequence

<400> SEQUENCE: 25
aaaaattttt t                                                             11
```

AUTOMATED METHODS FOR SCALABLE, PARALLELIZED ENZYMATIC BIOPOLYMER SYNTHESIS AND MODIFICATION USING MICROFLUIDIC DEVICES

CROSS-REFERENCE TO RELATED APPLICATIONS

This application claims the benefit of and priority to U.S. Application No. 62/521,612 filed Jun. 19, 2017, the contents of which is incorporated by reference in its entirety.

STATEMENT REGARDING FEDERALLY SPONSORED RESEARCH

This invention was made with government support under Grant No. N00014-16-121953 and Grant No. N00014-17-1-2609 awarded by the Office of Naval Research, under Grant No. DE-SC0001088 awarded by the U.S. Department of Energy Office of Basic Energy Sciences, and under Grant No. CCF-1564025 awarded by the National Science Foundation. The government has certain rights in the invention.

REFERENCE TO SEQUENCE LISTING

The Sequence Listing submitted Aug. 28, 2018, as a text file named "MIT_19620_ST25.txt," created on Aug. 10, 2018, and having a size of 5,128 bytes is hereby incorporated by reference pursuant to 37 C.F.R. § 1.52(e)(5).

FIELD OF THE INVENTION

The present invention relates to the automated de novo synthesis of nucleic acids and other biopolymers, and in particular to the use of electrowetting on dielectric, microfluidic, and liquid handling technology for high-throughput and dynamic production of biopolymers.

BACKGROUND OF THE INVENTION

DNA synthesis is often viewed as the next generation problem following on the successes of DNA sequencing. This global vision is embodied by recent efforts such as Human Genome Write where the goal is synthesis of a synthetic human genome. The need for synthesis of long strands of DNA (i.e., greater than 2,000 bases) is additionally shown by Yeast 2.0, minimal cell projects, and is a fundamental enabling technology of synthetic biology.

Two major approaches to DNA synthesis are phosphoramidite (chemical) synthesis and enzymatic synthesis. The synthesis of oligonucleotides (oligos) was first achieved in the 1950s by Todd, Khorana and co-workers using solution-based synthesis. (Todd, *J. Chem. Soc.*, pp. 2632-2638 (1955); Khorana, *J. Am. Chem. Soc.*, 79 (4): pp. 1002-1003 (1957)). In the 1980s Caruthers developed oligonucleotide synthesis on insoluble support using phosphoramidite synthons, which is currently the predominant method to synthesize oligonucleotide strands (Caruthers *Tetrahedr. Lett.* 22:1859-1862(1981)). The first step to synthesizing oligonucleotides using phosphoramidite precursors is to cleave the 5'-dimethoxytrityl protecting group from a 2'-deoxynucleoside covalently attached to controlled pore glass (the insoluble support). A protected 2'-deoxynucleoside-3'-phosphoramidite is then added to the support with tetrazole, which activates the added phosphoramidite. The formation of the covalent phosphite triester linkage occurs within 30 s. Next, an acetylation step using acetic anhydride with pyridine caps any unreacted 2'-deoxynucleoside, and removes phosphite adducts from the nucleobases. Finally, an oxidation step with iodine converts the phosphite linkage to a phosphate group. This cycle is repeated until the desired oligo sequence is synthesized, and then the oligo is cleaved from the solid support. Simultaneous synthesis of 96-768 oligonucleotides using this column-based approach is now feasible. However, the lengths of oligo that can be synthesized using the column-based approach is limited to up to only 200 nucleotides (Kosuri, *Nature Methods*, 11(5): 499:507(2014)). Other high-throughput oligo synthesis approaches have proliferated recently. Microarray-based approaches that also utilize phosphoramidite synthons are attractive for large scale synthesis of short oligonucleotide strands (*Science*, 251: pp. 767-773 (1991); *Proc. Natl. Acad. Sci.*, 91: pp. 5022-5026 (1994)). Photolithographic techniques are leveraged in array-based oligo synthesis approaches to selectively deprotect phosphoramidite precursors. Ink-jet based printing of nucleotides on microarray surfaces greatly increases the throughput of oligo synthesis (*Nature Biotechnology*, 19: 342:347 (2001)).

Template-free synthesis of DNA was discovered very early in biochemistry, noted by Arthur Kornberg. Other early examples include template free RNA polymerization with Qbeta replicase. Terminal deoxynucleotidyl transferase (TdT; terminal transferase) and telomerase are two more examples in biology where deoxynucleic acid (DNA) synthesis can occur in the absence of a DNA template, meaning that no first strand is needed (see, for example, U.S. Pat. Nos. 8,808,989 and 8,071,755, and U.S. Publication Nos. 2009/0186771, and 2011/0081647, and 2013/0189743). In the case of TdT, synthesis occurs in a 5' to 3' direction from an initiator primer and appends on deoxyribonucleic acid triphosphates (dNTPs) available in the surrounding solution. The TdT releases from the template after one or a few incorporations, and will a new polymerase will come on to continue affixing new nucleotides. Currently, sequence control of the incorporation of the nucleotides is achieved by addition of a single nucleotide to a solution, washing, and adding the next nucleotide in a cycle of additions of homopolymers.

Single-stranded Binding protein (SSB) is a protein found in many living systems and can bind non-specifically to single-stranded DNA. It is commercially available from New England Biolabs (NEB). For example, NEB offers highly thermostable ssDNA binding proteins that are ideal for nucleic acid amplification and sequencing (Tth RecA, NEB #M2402; and ET SSB, NEB #M2401). NEB also offers ssDNA proteins for use in visualization of DNA structures with electron microscopy and screening of DNA libraries (*E. coli* RecA, NEB #M0249, NEB #M0355) and to improve restriction enzyme digestion and enhance the yield of PCR products (T4 Gene 32 Protein, NEB #M0300).

Peptide synthesis on insoluble solid-support, pioneered by Robert Bruce Merrifield (*J. Am. Chem. Soc.*, 85(14): pp. 2149:2154 (1963)), is the standard method to synthesize peptides. A free N-terminal amine is coupled to an N-protected amino acid unit. The protecting group is then cleaved to introduce a free amino group to which another N-protected amino acid can be linked. The peptide is grown on the solid-support then finally cleaved to obtain the free synthesized peptide. Optional washing steps can be added for each step in the cycle to remove excess reagents from the column. The lengths of peptides that can be synthesized using the column approach is limited to 30-70 amino acid residues.

Longer polypeptides are realized by using native chemical ligation to "stitch" two or more polypeptides together.

Biotin is a small chemical adduct that can attached covalently to DNA at the 5' or 3' end or added covalently to proteins. Streptavidin is a protein that binds biotin tightly with ~10-14 mol/L Kd and this system is often used to attach proteins or DNA to a solid phase composed of a surface or to beads that can be manipulated through physical interactions, such as magnetically active beads. Many other methods of covalent or non-covalent attachment to solid-phase or surface supports are known in the art. Enzymes can also be controlled using temperature and small molecules including divalent ions such as magnesium, or drug molecules to either inhibit, decelerate, accelerate, or otherwise control their activity in vitro for functional applications such as programmed synthesis. Standard restriction enzymes also offer a way of manipulating synthesized DNA, for example, to cleave and release a nucleic acid from a substrate, etc., and in a sequence-specific manner when practical.

Microfluidics technologies exist for automated control of fluid movement actuated by various means. For example, Electrowetting On Dielectric (EWOD) is a method to control the movement of single picoliter to nanoliter droplets controlled through motive force by induced electric potential at the sight of the move (Sensors and Actuators A: Physical, 95(2-3), pp. 259-268 (2002)). Typically, a droplet of aqueous solution is held at a location by an induced electric potential on a dielectric. This droplet can be moved by moving the potential to a second adjacent location. By applying equal potential, the droplet can be split or merged, and movement of the droplet can induce mixing. Alternatively, the droplets in the EWOD device are steered by optical excitation of the electrode which creates a potential that induces droplet motion. The optical source can be shaped to create potential gradients to actuate the droplets in different directions. However, current methods using EWOD are restricted by the area of the EWOD surface, and the volume of the drop.

Digital information storage as sequences of nucleic acids is of interest in the storage market for archival memory storage Church, et al., Science; V. 337, (6102), pp. 1628 (2012); Goldman, et al., Nature, v. 494, pp 77-80 (2013); Zhirnov, et al., Nature Materials, V. 15, pp 366-370 (2016)). Methods of extraction of specific memory from a pool have also previously been implemented (Yazdi, et al., Scientific Reports V. 5, Article number: 14138 (2015); Bornholt, et al., IEEE Micro 37 (3); pp. 98-104 (2017); and Organick, et al., Nature Biotechnology, V36, pp. 242-248 (2018)), specifically showing the use of polymerase chain reaction with a hash table set of barcodes to amplify specific sequences from a pool. This approach is limited by the pool size that can be used due to PCR cross reactivity and amplification of spurious sequences that distract from the targeted sequence. Further, each data selection using a PCR-based approach either requires the extraction of the aliquot from the original sample, ultimately having to resynthesize the entire sample, or contaminates the original sample by introduction of enzymes.

There is a need for methods of biopolymer synthesis that are more efficient, more automatable, produce longer biopolymer strands, or combinations of these features.

There is also a need for methods of automated encapsulation of biopolymers for scalable, separable archival storage.

There is also a need for methods of barcode synthesis to retrieve the encapsulated product that can be dynamically allocated and rewritten without modifying the encapsulated product (such as a protected biopolymer).

Therefore, it is an object of the invention to provide systems and methods for automated synthesis of user-defined sequence-controlled biopolymers.

It is also an object of the invention to provide methods to dynamically alter biopolymer sequences using cutting enzymes or chemically-specific photo-degradation, followed by de novo enzymatic synthesis.

It is also an object of the invention to provide methods to simultaneously produce multiple distinctly addressed sequence-controlled biopolymers having distinct sequences and sizes.

It is also an object of the invention to provide fully automated systems and methods for large-scale synthesis of addressed biopolymers having user-defined sequence and size.

It is a further object of the invention to provide uniquely addressed synthesized biopolymers of user-defined sequence and size.

It is an object of the invention to provide methods of encapsulation of sequence-controlled biopolymers.

It is also an object of the invention to provide fully or partially automated systems and methods for pooling sequence-controlled biopolymers and encapsulating the pool into an encapsulated block.

It is also an object of the invention to provide fully or partially automated systems and methods for barcoding encapsulated blocks, removing the barcode, and/or re-attaching a barcode of the same or different sequence in a repeated way.

It is also an object of the invention to provide methods for selective modification of biopolymers.

It is also an object of the invention to provide fully or partially automated methods for the generation of barcode nucleic acid sequences of defined and adjustable melting temperatures.

It is also an object of the invention to provide methods of using fluorescent probe sequences complementary to barcode sequences to identify encapsulated blocks using fluorescence or other optical signature.

It is also an object of the invention to provide methods of using fluorescent probe sequences to sort encapsulated blocks.

It is a further object of the invention to provide methods of dynamically barcoding encapsulated blocks for retrieval and computation.

SUMMARY OF THE INVENTION

Methods for the scalable, automated, template-free synthesis, and/or modification of biopolymers using microfluidics systems have been developed. The methods optionally include encapsulation and dynamic molecular barcoding of nucleic acids and other biopolymers having a programmed sequence and size. Methods of using the synthesized biopolymers for archival storage, retrieval, modification, organization and re-organization of encoded data through movement of fluids using a microfluidic system are also provided.

The methods utilize microfluidic liquid handling technology for template-free synthesis and manipulation of biopolymers such as nucleic acids. In some forms, the methods enable massively parallelized nucleic acid synthesis with each location on a microfluidic platform growing an independent, geometrically addressed, long single-stranded nucleic acid by programmed movement of droplets containing nucleotides that are sequentially incorporated into the 3' end of the growing nucleic acid. The methods achieve the droplet cycling needed in the addition/de-protection steps for enzymatic DNA, RNA, and peptide synthesis. The methods optionally incorporate magnetic and/or temperature control globally or locally on the microfluidic platform, to enable additional control over the synthesis. Analogous methods can produce and/or modify sequences of numerous types of biopolymers using different component building blocks (such as monomers).

Exemplary microfluidic and liquid handling systems that can be employed for the methods include Electrowetting on Dielectric (EWOD) devices, acoustic droplet distribution devices, volumetric displacement distribution devices, ink-jet type fluidic distributors, or any other device that actuates micro-fluidic flow across a chip, for example, using microwells or synthetic compartments. A preferred microfluidic device is an EWOD chip.

In some forms, the methods generate biopolymers of programmed sequence and length in the absence of a template sequence. An exemplary biopolymer is single-stranded nucleic acid of greater than 200 nucleotides in length, for example, 500 nucleotides, 1,000 nucleotides, or 10,000 nucleotides, or greater than 10,000 nucleotides, for example up to 100,000 nucleotides in length. The methods optionally include the steps of purifying, amplifying, encapsulating, sequencing, functionalizing, and/or otherwise manipulating the synthesized biopolymers. In some forms, the methods add, remove, or modify one or more molecular sequence tags or barcodes within a biopolymer. In some forms the methods add, remove or modify one or more molecular sequence tags or barcodes on an encapsulated biopolymer. Some or all of the method steps can be carried out using a computer-controlled EWOD chip.

Typically, the methods for synthesizing biopolymers include the steps of (a) combining on a microfluidic device a droplet including a component initiation sequence with one or more droplets collectively comprising a component building block and an attachment catalyst to form a combined droplet; and (b) repeating step (a) to perform the step-wise addition of component building blocks to the biopolymer to form a biopolymer having a preselected, desired biopolymer sequence and length.

In an exemplary method, synthesis is carried out using movement of droplets actuated buy an Electrowetting on Dielectric (EWOD) microfluidic chip. Generally, the droplets including a component initiation sequence and each of the droplets collectively including the component building block and the attachment catalyst are, prior to the combining, at different locations on the EWOD chip. Generally, one or more additional droplets, each including an additional component building block, are at different locations on the EWOD chip than the droplet including the component initiation sequence, the droplets collectively including the component building block and the attachment catalyst, or the combined droplet. Generally, the combining includes conditions suitable for the attachment catalyst to attach the component initiation sequence to the component building block to form a biopolymer.

In some forms, the methods include the steps of (a) selecting a desired biopolymer sequence; (b) providing the component building blocks, attachment catalyst, component initiation sequence, wash reagents, and stop reagents as discrete droplets on a microfluidic device; (c) identifying the route and conditions for each droplet to combine with the other droplets to perform the step-wise addition, removal, or modification of building blocks to form a polymer having the desired biopolymer sequence; and (d) performing the step-wise addition, removal, or modification of building blocks to form a polymer having the desired biopolymer sequence according to the route identified in (c).

In some forms the methods optionally include the steps of isolating the biopolymer having the desired sequence from the microfluidic device. Exemplary attachment catalyst/agents include polymerase enzymes including TdT, Q-beta replicase, and teleomerase.

In some forms, the methods include the step of forming one or more of the droplets containing the component initiation sequence and the droplets collectively including the component building block and the attachment catalyst by splitting the droplets from reservoirs that collectively include the component initiation sequence, the component building block, and the attachment catalyst. In some forms, the methods include the step of forming one or more of the additional droplets by splitting the additional droplets from reservoirs that collectively comprise the additional component building blocks.

Methods of modifying a pre-existing biopolymer are also provided. For example, in some forms the methods attach component building blocks to a biopolymer to add one or more sections to one or more regions of the biopolymer. In other forms, the methods remove component building blocks from a biopolymer, for example, to remove one or more sections from the biopolymer. In some forms, the methods attach or remove a section to a biopolymer that is a molecular barcode. One or more molecular barcodes can be synthesized or attached to one or more positions of a biopolymer.

In some forms, the methods include one or more steps to alter the chemical or structural properties of synthesized single-stranded nucleic acid sequences. Therefore, methods for functionalizing single-stranded nucleic acid sequences using microfluidic systems are also provided. In some forms, methods include steps of functionalizing a newly-synthesized biopolymer by one or more processes that alter chemical or structural properties of the biopolymer. In some forms, chemical or structural properties of a newly-synthesized single-stranded nucleic acid are modified, for example, through addition of one or more oligonucleotide address sequences. In an exemplary form, methods of functionalizing single-stranded nucleic acids include conjugating a functionalized nucleic acid to the newly-synthesized nucleic acid prior to releasing or purifying the nucleic acid from the EWOD device.

In some forms, the methods manipulate a biopolymer to dynamically remove, modify, and/or attach one or more components. In some forms, the methods manipulate a section of a biopolymer that functions as a molecular barcode. For example, in some forms, the methods degrade a barcode site-specifically using cutting enzymes, or targeted photo-degradation, or other targeted cleavage, followed by elongating the polymer de novo to generate a new barcode sequence.

In some forms the methods include one or more steps to encapsulate a biopolymer. Encapsulation can be carried out using a material suitable for the encapsulation of the biopolymer. Preferably the encapsulation process occurs following polymer synthesis, and prior to purification. In some embodiments, two or more biopolymers are encapsulated together. Therefore, the step of encapsulating biopolymer(s) can include one or more steps of organizing, sorting and selecting biopolymers for encapsulation. In some forms, two or more biopolymers are encapsulated together according to identification of a common feature. An exemplary common feature is one or more components (e.g., sequences) that are common to molecular barcodes in two or more biopolymers.

In some forms optical activation of nucleotide precursors containing optically-cleavable functional groups that are known in the art is used to control nucleotide precursors incorporated by the enzyme (Mathews, et al., *Org Biomol Chem.* 14(35), pp. 8278-88 (2016)). In some forms, the methods modify nucleotides or other biopolymer subunits to improve the incorporation of additional moieties, or to facilitate sequencing. For example, in some forms, the methods include addition of hydrophobic moieties or conductive moieties to a biopolymer.

In some forms, the methods include substrates immobilized onto a solid support or surface. For example, in some forms, the methods include one or more component initiation sequences, a catalyst enzyme, and/or a biopolymer immobilized onto a solid support. In some forms, when a solid-support system is used, the methods employ continuous flow systems to actuate movement of substrates. For example, the growing biopolymer can be isolated from the continuous flow in a droplet that is contained within a covering material, for example, formed by a lipid or other chemical matrix. Access to the droplet including the immobilized initiator sequence, the catalyst enzyme, or biopolymer is controlled, for example, by opening or closing channels through the cover material or by direct penetration through the cover material.

In some forms, the methods include the step of encapsulating a biopolymer within an encapsulating agent. In other forms, the methods include the step of degrading or otherwise removing an existing encapsulating agent from one or more regions of the biopolymer. For example, in some forms, the methods remove an encapsulating agent, then remove, add, or substitute one or more sequences or other components of the biopolymer, then re-encapsulate the modified biopolymer in the same of different encapsulating agent.

In some forms, the step of purifying the synthesized nucleic acids from the microfluidic device includes polymerase chain reaction (PCR). For example, PCR using the desired sequence as a scaffold can be used to amplify and/or purify the desired sequence from the EWOD chip. In some forms, the length of the scaffold is 100 or more nucleotides in length, e.g., 1,000 nucleotides in length; 1,500 nucleotides in length; 2,000 nucleotides in length; 2,500 nucleotides in length; 3,281 nucleotides in length; 10,000 nucleotides in length; 12,000 nucleotides in length; or greater than 12,000 nucleotides.

In some forms, the biopolymer is functionalized by introduction of functionalized component building blocks into the solution. Exemplary functional components include fluorescent moieties, radio-labeled moieties, and magnetic moieties. In an exemplary form, modified nucleotides are used as component building blocks for nucleic acid polymer synthesis. Exemplary modified nucleotides include Cy5 fluorophore-modified nucleotides, phosphorothioate-modified nucleotides, and deoxyuridines.

Methods of using EWOD-based template-free synthesis for the parallel, simultaneous synthesis of multiple different biopolymers are provided. For example, in some forms, individual biopolymers having a pre-programmed length and sequence are prepared at individual locations on the same EWOD chip to simultaneously produce multiple independent, geometrically addressed, biopolymers. In an exemplary method, long single-stranded DNA is synthesized by programmed movement of droplets containing the nucleotide that will next be incorporated into the 3' location. This technology is broadly applicable to the same droplet cycling needed in the addition/deprotection steps of chemical DNA, RNA, and peptide synthesis. Incorporation of magnetic and/or temperature control globally or locally on the dielectric chip offers additional utility for control over the synthesis. Compositions of biopolymers synthesized according to the described methods are also provided.

Figure 1:
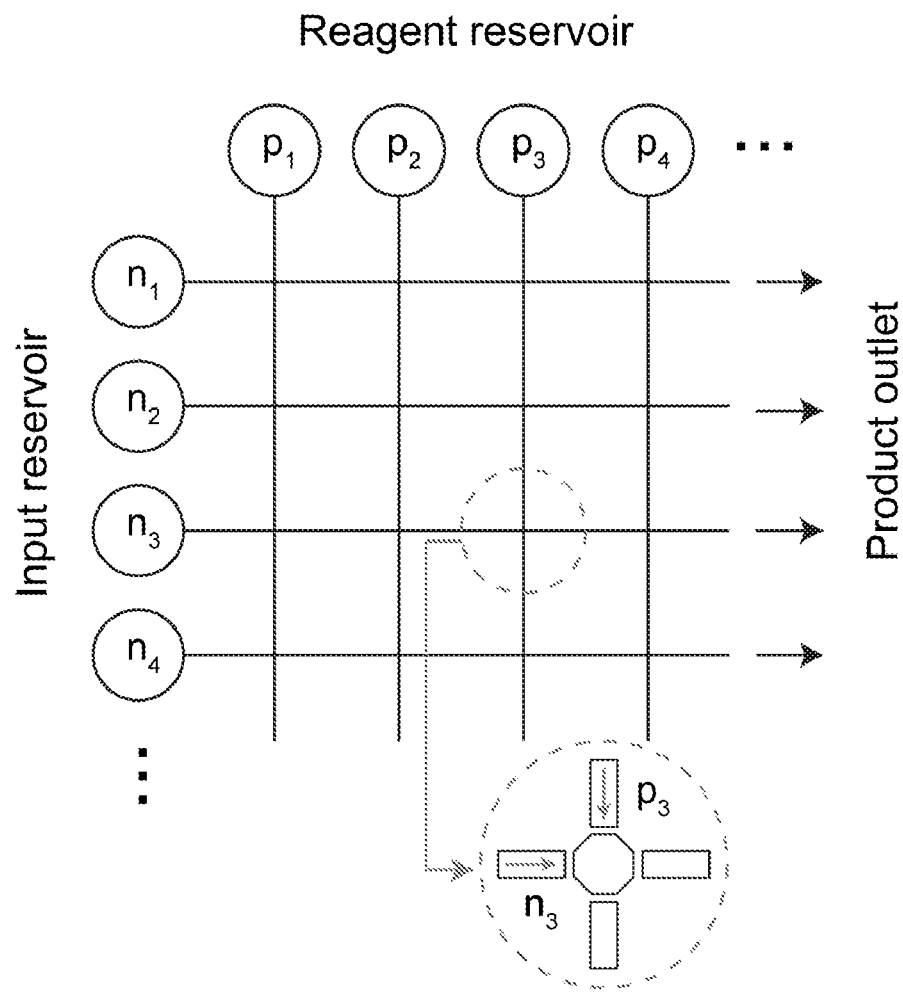
FIG. 1 is a schematic of an EWOD device that shows the reagent reservoirs and channel addressing of the reagents for parallelized DNA synthesis. For illustrative purposes, the channels are drawn to show the path of the droplets. In other forms, the channels are removed completely and the droplets are created and moved by an optical source. The channels can contain, but not limited to, the enzyme, the nucleotide precursors, the reaction initiator, a capping reagent, a washing reagent, and a chemical to halt enzymatic activity. The channels are attached to a collection reservoir where the DNA is capture for subsequent use.

In some forms, the methods synthesize and/or manipulate nucleic acid barcodes. For example, in some forms, the methods implement a scheme for molecular identification that includes mutations in the barcode for similar terms. In some forms, multiple point mutations within a nucleic acid sequence that is a barcode are combined to provide a molecular database of barcode. Therefore, in some forms, blocks of sequence-controlled biopolymers can be addressed by different identifying barcodes that are themselves separate sequence-controlled biopolymers that represent the metadata encoded by a memory object, similar to a "molecular hash". In some forms, the methods introduce sets of point mutations in barcodes. Therefore, in some forms the methods enable more similar polymer-blocks to be extracted from the solution more readily than sequences that are not similar. For example in one exemplary form, a 25-mer barcode sequence is selected to be representative of "red" and a separate 25-mer barcode sequence is selected to be representative of "blue" (exemplary barcodes are described in the article entitled "Design of 240,000 orthogonal 25mer DNA barcode probes", by Xu, et al., Proc Natl Acad Sci, 106 (7) 2289-2294 (2009)). Point mutations are made to make the barcode less similar to the original barcode, and reverse complements of each are obtained. A melting temperature is determined (e.g., by quantitative PCR) for each primer pair corresponding to metadata of "red"s, "like-red"s, "blue"s, and "like-blue"s, respectively. High melting temperatures indicate perfect complementarity, while the nearby neighbors indicate selections could include non-specific (i.e., "fuzzy", or "noisy") retrieval of corresponding metadata.

DETAILED DESCRIPTION OF THE INVENTION

I. Definitions

The term "nucleotide" refers to a molecule that contains a base moiety, a sugar moiety and a phosphate moiety. Nucleotides are typically linked together through their phosphate moieties and sugar moieties creating an inter-nucleoside linkage. The base moiety of a nucleotide can be adenin-9-yl (A), cytosin-1-yl (C), guanin-9-yl (G), uracil-1-yl (U), and thymin-1-yl (T). The sugar moiety of a nucleotide is a ribose or a deoxyribose. The phosphate moiety of a nucleotide is pentavalent phosphate. A non-limiting example of a nucleotide would be 3'-AMP (3'-adenosine monophosphate) or 5'-GMP (5'-guanosine monophosphate).

The term "residue" of a chemical species refers to the moiety that is the resulting product of the chemical species in a particular reaction scheme or subsequent formulation or chemical product, regardless of whether the moiety is actually obtained from the chemical species. Thus, an ethylene glycol residue in a polymer refers to one or more —OCH$_2$CH$_2$O— units in the polymer, regardless of whether ethylene glycol was used to prepare the polyester. As another example, in a polymer of monomer subunits, the incorporated monomer subunits can be referred to as residues of the un-polymerized monomer.

The term "nucleotide analog" refers to a nucleotide which contains some type of modification to the base, sugar, or phosphate moieties. Modifications to nucleotides are well known in the art and would include for example, 5-methylcytosine (5-me-C), 5-hydroxymethyl cytosine, xanthine, hypoxanthine, and 2-aminoadenine as well as modifications at the sugar or phosphate moieties. There are many varieties of these types of molecules available in the art and available herein.

The term "nucleotide substitute" refers to a nucleotide molecule having similar functional properties to nucleotides, but which does not contain a phosphate moiety. An exemplary nucleotide substitute is peptide nucleic acid (PNA). Nucleotide substitutes are molecules that will recognize nucleic acids in a Watson-Crick or Hoogsteen manner, but which are linked together through a moiety other than a phosphate moiety. Nucleotide substitutes are able to conform to a double helix type structure when interacting with the appropriate target nucleic acid. It is also possible to link other types of molecules (conjugates) to nucleotides or nucleotide analogs to enhance for example, interaction with DNA. Conjugates can be chemically linked to the nucleotide or nucleotide analogs. Exemplary conjugates include but are not limited to lipid moieties such as a cholesterol moiety.

The terms "nucleic acid," "polynucleotide," and "oligonucleotide" are interchangeable and refer to a deoxyribonucleotide or ribonucleotide biopolymer, in linear or circular conformation, and in either single- or double-stranded form. For the purposes of the present disclosure, these terms are not to be construed as limiting with respect to the length of a biopolymer. The terms can encompass known analogues of natural nucleotides, as well as nucleotides that are modified in the base, sugar and/or phosphate moieties (e.g., phosphorothioate backbones, locked nucleic acid). In general and unless otherwise specified, an analogue of a particular nucleotide has the same base-pairing specificity; i.e., an analogue of A will base-pair with T. When double-stranded DNA is described, the DNA can be described according to the conformation adopted by the helical DNA, as either A-DNA, B-DNA, or Z-DNA. The B-DNA described by James Watson and Francis Crick is believed to predominate in cells, and extends about 34 Å per 10 bp of sequence; A-DNA extends about 23 Å per 10 bp of sequence, and Z-DNA extends about 38 Å per 10 bp of sequence.

In some cases nucleotide sequences are provided using character representations recommended by the *International Union of Pure and Applied Chemistry* (IUPAC) or a subset thereof. IUPAC nucleotide codes include, A=Adenine; C=Cytosine; G=Guanine; T=Thymin; U=Uracil; R=A or G; Y=C or T; S=G or C; W=A or T; K=G or T; M=A or C; B=C or G or T; D=A or G or T; H=A or C or T; V=A or C or G; N=any base; "." or "-"=gap. In some forms the set of characters is (A, C, G, T, U) for adenosine, cytidine, guanosine, thymidine, and uridine respectively. In some forms the set of characters is (A, C, G, T, U, I, X, Ψ) for adenosine, cytidine, guanosine, thymidine, uridine, inosine, uridine, xanthosine, pseudouridine, respectively. In some forms the set of characters is (A, C, G, T, U, I, X, Ψ, R, Y, N) for adenosine, cytidine, guanosine, thymidine, uridine, inosine, uridine, xanthosine, pseudouridine, unspecified purine, unspecified pyrimidine, and unspecified nucleotide, respectively.

The terms "polypeptide," "peptide," and "protein" are used interchangeably to refer to a polymer of amino acid residues. The term also applies to amino acid polymers in which one or more amino acids are chemical analogues or modified derivatives of corresponding naturally-occurring amino acids.

The terms "cleavage" and "cleaving" of nucleic acids, refer to the breakage of the covalent backbone of a nucleic acid molecule. Cleavage can be initiated by a variety of methods including, but not limited to, enzymatic or chemical hydrolysis of a phosphodiester bond. Both single-stranded cleavage and double-stranded cleavage are possible, and double-stranded cleavage can occur as a result of two distinct single-stranded cleavage events. DNA cleavage can result in the production of either blunt ends or staggered "sticky" ends. In certain forms cleavage refers to the double-stranded cleavage between nucleic acids within a double-stranded DNA or RNA chain.

Nucleotide and/or amino acid sequence identity percent (%) is understood as the percentage of nucleotide or amino acid residues that are identical with nucleotide or amino acid residues in a candidate sequence in comparison to a reference sequence when the two sequences are aligned. To determine percent identity, sequences are aligned and if necessary, gaps are introduced to achieve the maximum percent sequence identity. Sequence alignment procedures to determine percent identity are well known to those of skill in the art. Often publicly available computer software such as BLAST, BLAST2, ALIGN2 or MEGALIGN (DNASTAR) software is used to align sequences. Those skilled in the art can determine appropriate parameters for measuring alignment, including any formulas needed to achieve maximal alignment over the full-length of the sequences being compared. When sequences are aligned, the percent sequence identity of a given sequence A to, with, or against a given sequence B (which can alternatively be phrased as a given sequence A that has or comprises a certain percent sequence identity to, with, or against a given sequence B) can be calculated as: percent sequence identity=X/Y100, where X is the number of residues scored as identical matches by the sequence alignment program's or formula's alignment of A and B and Y is the total number of residues in B. If the length of sequence A is not equal to the length of sequence B, the percent sequence identity of A to B will not equal the percent sequence identity of B to A. Mismatches can be similarly defined as differences between the natural binding partners of nucleotides. The number, position and type of mismatches can be calculated and used for identification or ranking purposes.

The term "endonuclease" refers to any wild-type or variant enzyme capable of catalyzing the hydrolysis (cleavage) of bonds between nucleic acids within a DNA or RNA molecule, preferably a DNA molecule. Non-limiting examples of endonucleases include type II restriction endonucleases such as FoId, HhaI, HindIII, NotI, BbvCl, EcoRI, BglII, and AlwI. Endonucleases comprise also rare-cutting endonucleases when having typically a polynucleotide recognition site of about 12-45 basepairs (bp) in length, more preferably of 14-45 bp. Rare-cutting endonucleases induce DNA double-strand breaks (DSBs) at a defined locus. Rare-cutting endonucleases can for example be a homing endonuclease, a mega-nuclease, a chimeric Zinc-Finger nuclease (ZFN) or TAL effector nuclease (TALEN) resulting from the fusion of engineered zinc-finger domains or TAL effector domain, respectively, with the catalytic domain of a restriction enzyme such as FoId, other nuclease or a chemical endonuclease including CRISPR/Cas9 or other variant and guide RNA.

The term "exonuclease" refers to any wild type or variant enzyme capable of removing nucleic acids from the terminus of a DNA or RNA molecule, preferably a DNA molecule. Non-limiting examples of exonucleases include exonuclease I, exonuclease II, exonuclease III, exonuclease IV, exonuclease V, exonuclease VI, exonuclease VII, exonuclease VII, Xm1, and Rat1. In some forms, an enzyme is capable of functioning both as an endonuclease and as an exonuclease. The term "nuclease" generally encompasses both endonucleases and exonucleases, however in some forms the terms "nuclease" and "endonuclease" are used interchangeably herein to refer to endonucleases, i.e., to refer to enzyme that catalyze bond cleavage within a DNA or RNA molecule.

The term "ligating" refers to enzymatic reactions in which two double-stranded DNA molecules are covalently joined, for example, as catalyzed by a ligase enzyme.

The terms "aligning" and "alignment" refer to the comparison of two or more nucleotide sequence based on the presence of short or long stretches of identical or similar nucleotides. Several methods for alignment of nucleotide sequences are known in the art, as will be further explained below.

The term "nucleic acid capture" refers to binding of any nucleic acid molecule of interest having complementary nucleic acid sequences to a corresponding sequence associated with a separate nucleic acid, or having affinity for the sequence employed, and being immobilized or attached to a solid support matrix. For example, "RNA capture" refers to binding of any ribonucleic acid molecule of interest to the complementary sequence on a nucleic acid coupled to a solid support matrix.

The phrase that a molecule "specifically binds" to a target refers to a binding reaction which is determinative of the presence of the molecule in the presence of a heterogeneous population of other biologics. Thus, under designated immunoassay conditions, a specified molecule binds preferentially to a particular target and does not bind in a significant amount to other biologics present in the sample. Specific binding of an antibody to a target under such conditions requires the antibody be selected for its specificity to the target. A variety of immunoassay formats may be used to select antibodies specifically immunoreactive with a particular protein. For example, solid-phase ELISA immunoassays are routinely used to select monoclonal antibodies specifically immunoreactive with a protein. See, e.g., Harlow and Lane (1988) Antibodies, A Laboratory Manual, Cold Spring Harbor Publications, New York, for a description of immunoassay formats and conditions that can be used to determine specific immunoreactivity. The term "specific binding", for example, between two entities, means an affinity of at least $10^6$, $10^7$, $10^8$, $10^9$, or $10^{10}$ M-1. Affinities greater than $10^8$ M-1 are preferred.

The term "targeting molecule" refers to a substance which can direct a synthesized biopolymer to a receptor site on a selected cell or tissue type, can serve as an attachment molecule, or serve to couple or attach another molecule. The term "direct" refers to causing a molecule to preferentially attach to a selected cell or tissue type. This can be used to direct cellular materials, molecules, or drugs, as discussed below.

The terms "antibody" and "immunoglobulin" include intact antibodies, and binding fragments thereof. Typically, fragments compete with the intact antibody from which they were derived for specific binding to an antigen fragment, including separate heavy chains, light chains Fab, Fab' F(ab')2, Fabc, and Fv. Fragments are produced by recombinant DNA techniques, or by enzymatic or chemical separation of intact immunoglobulins. The term "antibody" also includes one or more immunoglobulin chains that are chemically conjugated to, or expressed as, fusion proteins with other proteins. The term "antibody" also includes a bispecific antibody. A bispecific or bifunctional antibody is an artificial hybrid antibody having two different heavy/light chain pairs and two different binding sites. Bispecific antibodies can be produced by a variety of methods including fusion of hybridomas or linking of Fab' fragments. See, e.g., Songsivilai and Lachmann, Clin. Exp. Immunol., 79:315-321 (1990); Kostelny, et al., J. Immunol., 148, 1547-1553 (1992).

The terms "epitope" and "antigenic determinant" refer to a site on an antigen to which B and/or T cells respond. B-cell epitopes can be formed both from contiguous amino acids or noncontiguous amino acids juxtaposed by tertiary folding of a protein. Epitopes formed from contiguous amino acids are typically retained on exposure to denaturing solvents whereas epitopes formed by tertiary folding are typically lost on treatment with denaturing solvents. An epitope typically includes at least 3, and more usually, at least 5 or 8-10, amino acids, in a unique spatial conformation. Methods of determining spatial conformation of epitopes include, for example, x-ray crystallography and 2-dimensional nuclear magnetic resonance.

The term "small molecule," as used herein, generally refers to an organic molecule that is less than about 2,000 g/mol in molecular weight, less than about 1,500 g/mol, less than about 1,000 g/mol, less than about 800 g/mol, or less than about 500 g/mol. Small molecules are non-polymeric and/or non-oligomeric.

The term "droplet" refers to a distinct volume of a fluid that is distinct and separate from, and independently movable from, other droplets. Fluid droplets are generally formed by splitting a volume of fluid from a reservoir containing a larger volume of the same fluid.

The terms "attachment reagent," "attachment catalyst/agent," "assembly reagent," "catalyst," "assembly catalyst," "attachment catalyst," and "catalyst reagent" refer to a reagent that actuates, enhances, increases, or otherwise enables the addition of a component building block onto an initiator sequence or onto a growing biopolymer. Typically, the attachment of a component building block by a catalyst is controlled by movement of one or more fluid droplets according to an EWOD device. An exemplary molecule that specifically enhances the addition of one or more nucleotide building blocks to a growing nucleic acid biopolymer is a template-free polymerase. Exemplary attachment agents include TdT, Qbeta replicase, and telomerase enzymes.

The terms "building block" and "component building block" refer to a discrete component of the biopolymer that is formed by step-wise addition to an initiator. Building blocks are typically basic structural units of biopolymers, such that biopolymers result from the step-wise assembly of the building blocks. Exemplary building blocks include nucleotides, amino acids, monosaccharides and polypeptides. In some forms, building blocks are monomers. In other forms, building blocks are multimers, such as dimers, homodimers, heterodimers, oligomers etc. Exemplary multimers of basic structural units include short nucleic acid sequences, di-peptides, tri-peptides, and oligosaccharides.

The terms "initiator," "initiator sequence," "component initiation sequence," and "initiating oligomer" refer to a discrete sequence of component building blocks that acts as an initiation molecule for the step-wise template-free assembly of component building blocks for synthesis of a user-defined biopolymer. In some forms, the initiator molecule includes one or more recognition sequences for an attachment catalyst. An exemplary initiator sequence is an oligonucleotide including a nucleic acid sequence that is a recognition sequence of a TdT enzyme.

The term "sequence," in the context of the disclosed biopolymers, refers to the order of building blocks, such as nucleotides, in the biopolymer. For example, common DNA has a sequence of nucleotide building blocks chosen from A, C, G, and T. Biopolymers made from other types of building blocks will have sequences defined by the order of those building blocks in the biopolymer.

The term "bead" or "magnetic bead" refers to a solid structure that is used as a support matrix for one or more reagents when used in methods for synthesis of biopolymers. Beads can be any suitable bead.

The terms "wash reagent," "wash buffer," "wash," and "rinse solution" refer to a solution that is used to purify remove one or more reagents from a biopolymer, initiator or catalyst. Typically, the wash buffer is a solvent that is effective to solvate and remove reagents from a molecule that is immobilized, for example, an immobilized biopolymer. The wash buffer can be contacted with a droplet of solution, or can be the solvent used to dissolve one or more reagents, for example, to reduce or prevent the activity of the reagent.

The term "wash conditions" refers to the environmental/external conditions under which combination with a wash reagent (i.e., a distinct "wash step") is carried out. For example, a wash can be carried out by combining one or more wash reagents with a solution or immobilized support containing the biopolymer or initiator, and subsequent exposure of the combined solution to one or more environmental/external conditions. Exemplary conditions include the time of combination, the amount and concentration of each wash reagent, exposure to agitation, exposure to heat, light, vapor, changes in pressure, changes in electrical charge, etc.

The term "stop reagents" refers to a reagent that selectively or non-selectively reduces or prevents the activity of an active agent. For example, a stop-reagent can have a pH or contain a molecule that interferes with the activity of an enzyme. Typically, stop reagents change the parameters of a solution into which they are mixed, for example, to change pH, change temperature, change ion concentration, competitively bind to an active site on an active agent, etc. In some forms, stop reagents selectively bind and/or sequester co-factors necessary for enzyme function. Exemplary stop reagents include acids, bases, ionic solutions and glycerol. In some forms, stop reagents immediately prevent or impede one or more attachment reactions, for example, by inhibiting the activity of the catalyst enzyme, or by sequestering or otherwise reducing/altering the concentration of component building blocks available for addition.

The term "stop conditions" refers to the environmental/external conditions under which combination with a stope reagent (i.e., a distinct "stop step") is carried out. For example, stop conditions can include combining one or more stop reagents with a solution or immobilized support containing the biopolymer or initiator, and subsequent exposure of the combined solution to one or more environmental/external conditions. Exemplary conditions include the time of combination, the amount and concentration of each wash reagent, exposure to agitation, exposure to heat, light, vapor, changes in pressure, changes in electrical charge, etc.

The term "blocking reagents" refers to a reagent that specifically blocks a chemical reaction, for example, to prevent the addition of an amino acid to a growing polypeptide biopolymer. Typically, blocking reagents add a chemical "cap," or other molecule to the terminal component building block in the biopolymer "chain". The cap selectively prevents the addition of a subsequent component building block at the respective location on the biopolymer. The term "unblocking reagents" refers to any agent that reverses, reduces, or otherwise abrogates the effects of a blocking reagent. Unblocking agents are typically not wash reagents. Rather, unblocking agents actively modify the biopolymer to enable, induce or enhance the attachment of a component building block at a site that was previously blocked.

The term "attachment conditions" refers to the conditions under which the user-defined attachment of component building blocks to an initiator, or to the terminal component building block of a biopolymer (i.e., a distinct "attachment step") is carried out. For example, attachment can be carried out by combining the attachment agent with the initiator or biopolymer and one or more component building blocks under conditions amenable to the function of the catalyst. Exemplary conditions include the time of combination, the amount and concentration of each reagent, ionic concentration, presence of any necessary co-factors, absence of stop reagents, exposure to agitation, exposure to heat, light, vapor, changes in pressure, changes in electrical charge, etc.

The terms "encapsulating", "enveloping", "coating", "covering", and "shelling" are used interchangeably to refer to the process by which biopolymers, and optionally additional agents, are completely or partially enclosed by an encapsulating agent. The term "encapsulating agent" refers to a molecular entity, such as a polymer or other matrix.

The terms "microfluidic device", "microfluidics", "microfluidic chip", and "microfluidic platform" refer to any device, or system that supports and/or enables or actuates the movement of sub-microliter volumes of fluids, for example, as discrete droplets. Typically, microfluidic devices implement components and means for controlling the user-defined splitting, movement, and combining of discrete fluid droplets in a controlled manner, as well as modifying or altering one or more physicochemical properties, such as temperature, electric charge, light, magnetic force, etc. In some forms, microfluidic devices control the movement, behavior and manipulation of fluids through one or more means for actuating fluid movement. Exemplary microfluidic devices actuate fluid movements through mechanisms including continuous flow, fluid dispensing, EWOD, pressure, optical or combinations thereof. Microfluidic devices can be "open" (i.e., fluid is contained, moved and manipulated on a single surface), or "closed" (i.e., fluid is contained, moved and manipulated between two surfaces). In some forms, the term "microfluidic device" is used interchangeably with "microfluidic system", and includes the means for inputting user-defined control of fluid manipulation (e.g., through a general-user interface that employs computer software to control the movement of fluids within the device). The term "microfluidic system" also refers to additional equipment, such as equipment that is external to apparatus for controlling fluid movement, for example, devices for controlling parameters such as temperature, light, pressure, humidity, etc. In some form, "microfluidic devices" include devices and systems to input data for control of the movement or manipulation of the droplets on a microfluidic platform located close to, or at a distance from the site of data input. In some forms, the data input device is or incorporates a computer. In some forms, the system or device includes one or more systems for providing information to the control system, e.g., a device for proving feedback. In some forms, data input is autonomous (e.g., computational tasks can be performed, autonomously, like programs that run on conventional silicon computers, but here in the liquid state).

The terms "EWOD", or "Electrowetting" refers to the technique of Electrowetting on dielectric (EWOD) to control the movement of single picoliter to nanoliter droplets, e.g., through motive force by induced electric potential at the sight of the move (Sensors and Actuators A: Physical, 95(2-3), pp. 259-268 (2002)). The terms "EWOD chip", "EWOD platform", or "EWOD device" refer to a platform or similar equipment, for actuating the movement of fluids by the EWOD phenomenon. An exemplary EWOD chip is a microfluidic chip, such as a digital microfluidic chip. EWOD chips can be "open" (i.e., fluid droplets move across a surface without a layer above the fluid), or "closed" (i.e., fluid droplets move across a surface with a second layer above the fluid).

II. Methods for Automated Synthesis and Manipulation of Biopolymers

Systems and methods for the automated, step-wise synthesis and/or manipulation of a biopolymer having a user-defined sequence/structure and size have been established. The systems and methods do not require a pre-existing template sequence or structure. The methods generally involve step-wise assembly of distinct component building blocks (e.g., nucleotides, amino acids, monosaccharides, etc.) onto a component initiation sequence as droplets at one or more discrete locations on a microfluidic platform. In some forms, the methods synthesize and/or manipulation of user-defined sequences of nucleic acids (e.g., DNA or RNA) using a grid-addressable location in a sequence-specified manner in an absence of a template on an electrowetting-on-dielectric (EWOD) chip.

The addressed position of the growing polymer strand is determined by the position on a microfluidic platform, such as an EWOD chip. In some forms the growing biopolymer is held stationary on the microfluidic platform by fixing a component initiation sequence to a surface at the addressed location, or fixing the component initiation sequence to a magnetic bead and holding it in location by a strong magnet. The operating temperature can be varied according to the requirement of the synthesis. User-defined movement of droplets (e.g., through the electric potential induced by an EWOD chip) droplets containing component building blocks, buffers, and attachment catalyst, are moved and combined and mixed with the droplet containing the growing biopolymer sequence chain.

An exemplary catalyst is a template-free polymerase enzyme for the assembly of a nucleic acid. Upon combining appropriate droplets, the enzyme attaches available nucleotides to the 3' end of the polymer (see, for example, *Biochimica et Biophysica Acta,* 1804(5): pp. 1151-1166 (2010)). Droplets including one or more component building blocks are combined with the enzyme solution and are sequentially incorporated onto the growing biopolymer chain. Either by limiting the nucleic acid number available per reaction, or by removing the nucleotides and solution by removing the droplet but keeping the sequence fixed in its addressed grid location and washing 1, 2, 3, or more than 3 times with droplets containing just water or just buffer and salts will allow for programmed time stops of reactions.

Because microfluidic platforms, such as EWOD chips, are typically small in grid size, and can be simultaneously moved and controlled by preprogramming the steps of merging, mixing, and separating, a biopolymer having a pre-defined programmed sequence can be grown at the addressed locations. The movement, splitting, and merging of droplets is not limited to electrical operation (e.g., as implemented through an EWOD device), but can also be actuated utilizing optical control to perform operations using droplets. Thus, by increasing the size of the chip to include more grid points, 1 strand, 1,000 strands, 1,000,000 strands or more can be synthesized simultaneously. Because the TdT enzyme is only limited by occlusion from the 3' end by the single-stranded DNA, the growing polymer can be of size 100 nts, 1,000 nts, up to 10,000 nucleotides, or more than 10,000 nts.

In preferred forms, the assembly process is mediated by the activity of one or more attachment catalysts. Therefore, control of the assembly process is mediated by the rate and activity of the attachment catalyst. Attachment catalysts are selected according to the nature of the biopolymer that is the desired end-product of the synthesis. Exemplary attachment catalysts include enzymes (e.g., polymerases, phosphatases, esterases, lipases, glycosyl-transferases, and proteases), acids, as well as external conditions such as light (e.g., photo-switched assembly), air and heat. In other forms, the assembly process occurs in the absence of an attachment catalyst. For example, if the component building blocks are polypeptides, proteins, nanostructures, etc., assembly can occur through interaction specific or non-specific interaction between the initiator element and the component building block. An exemplary non-catalyzed assembly is the dimerization following interaction between two G actin proteins.

In some forms, the methods synthesize polymers onto one or more solid support matrices. In some forms, the component initiation sequence is coupled to a magnetic bead to facilitate the step-wise assembly process. The solid support anchors the initiator sequence in a user-determined address location on the microfluidic device, enabling the step-wise movement of reagents onto and away from the initiator sequence as required to achieve optimal assembly. When the component initiation sequence is coupled to a solid support, methods for assembling the biopolymer can include iterations of microfluidic device-mediated movement of aqueous droplets to sequentially combine the component initiation sequence with droplets containing different reagents. Therefore, in some forms the step of combining the initiator sequence and one or more component building blocks includes sequential combination of the immobilized initiator sequence with one or more droplets including one or more reagents including wash buffers, component building blocks, assembly catalysts, buffers, blocking reagents, and/ or stopping reagents. Each microfluidic device-mediated combination and separation event can be repeated one or more times to selectively combine/mix or separate/exclude one reagent from another. For example, the step-wise assembly of each building block can be carried out as a cycle including microfluidic device-mediated movement of droplets to combine an subsequently separate the immobilized initiator sequence with (1) wash buffer; (2) a component building block and assembly catalyst and optionally one or more buffers required for the assembly catalyst to combine the component building block with the initiator sequence; (3) a blocking reagent and/or stopping reagent to prevent the activity of the assembly catalyst, and (4) a wash buffer. The cycle can be repeated to sequentially add each component building block to the growing biopolymer. Factors such as the timing between each microfluidic device-mediated movement of droplets, and external conditions can be optimized according to the requirements of each biopolymer. The biopolymer remains attached to the solid support matrix throughout the cyclic assembly process, and can be cleaved away from the support matrix following addition of the last component building block.

In some forms, a software program is used to coordinate the microfluidic device-mediated movement of droplets.

Typically, the methods include one or more of the following steps:

(a) Selecting a target polymer;
(b) providing reagents as droplets on a microfluidic device, the reagents including
  (i) a component initiation sequence;
  (ii) one or more component building block(s); and
  (iii) an attachment catalyst;
  wherein the a component initiation sequence is provided as a separate droplet from the component building blocks;
(c) combining a droplet comprising the component initiation sequence with one or more droplet(s) comprising a component building block and an attachment catalyst to form a combined droplet,
  wherein the combining comprises conditions suitable for the attachment catalyst to attach the component initiation sequence to the component building block to form a biopolymer.

In some forms the methods further include the steps of
(i) Blocking or otherwise reducing, stopping or preventing the attachment of the component building block to the biopolymer;
(ii) Washing the biopolymer with one or more wash buffers to reduce or remove one or more reagents from the developing or completed biopolymer; and
(iii) Modifying the biopolymer, for example, by addition or removal of one or more functional motifs.

In some forms the methods further include the steps of
(d) Purifying or otherwise isolating the biopolymer from the EWOD chip.
(e) Confirming or assessing the microfluidic device-synthesized biopolymer. Confirming the biopolymer can include sequencing or amplifying the completed biopolymer.

A. Selecting a Target Biopolymer

The methods synthesize a sequence-controlled "target" biopolymer having user-defined sequence and size using addressed locations on an microfluidic device. Methods for microfluidic device-based template-free synthesis of target biopolymers from corresponding component building blocks provide the ability to simultaneously synthesize multiple biopolymers having the same or different sequences using the same microfluidic device. Automated synthesis can be carried out for one or more biopolymers simultaneously on the same microfluidic device from instructions input as a sequence of droplet movements corresponding to uniquely addressed locations on the chip.

The step of selecting a target biopolymer generally includes the steps of: (1) determining the number and composition of biopolymers to be synthesized; (2) rendering a microfluidic platform as a grid network; and (3) assigning a unique address to each node identified by intersecting grid-lines on the network. In some forms, biopolymers are synthesized at a single location on the microfluidic device grid. Biopolymers can be addressed according to the node/ location of synthesis on the grid network. Therefore, in some forms, the methods include the step of assigning a unique address to each biopolymer.

1. Selecting Number and Composition of Biopolymers

Methods for the programmable microfluidic device-mediated template-free synthesis of a user-defined biopolymer require the user-defined input of the sequence and size of the desired biopolymer. In some forms, biopolymer sequences are selected based upon one or more design criteria. In other forms biopolymer sequences are selected randomly.

The step-wise assembly of component building blocks onto an initiator sequence is aided when the relative location of each component building block is determined in one or more distinct fluid reservoirs on the microfluidic device to enable the appropriate coordinated movement of droplets. Therefore, in some forms the methods require input parameters that define the target sequence(s) to be synthesized. Input can be in the form of a computer-readable program. Therefore, in some forms, the starting point for the synthesis process is the identification of the target sequence. When multiple polymers having the same or different sequences are required, the user must designate each sequence as having a specific location on the microfluidic device for the synthesis to originate.

In an exemplary form, the user-defined sequence is a nucleic acid, and the reservoirs of component building blocks that are addressed are selected according to the number of different nucleotide bases to be incorporated into the biopolymer. For example, synthesis of a DNA sequence would typically require at least four distinct reservoirs of component building blocks, one for each of the main nucleobases found in DNA (i.e., one reservoir for each of adenine, cytosine, thymine, and guanine), as well as one or more reservoirs for each of the appropriate assembly catalyst (i.e., a template-free polymerase enzyme), a reaction buffer, one or more wash buffers (e.g., water), as well as a stopping buffer (e.g., to deactivate the polymerase enzyme). Some reagents used in the methods can be combined in the same reservoir or kept in separate reservoirs. Some reagents, such as individual nucleotides to be added in particular sequence order, should be in separate reservoirs from each other.

The number of different biopolymers that is to by synthesized is also considered. The methods enable the automated synthesis of up to 1,000,000 different polymers on the microfluidic device. In an exemplary form, the methods synthesize ten different nucleic acids, each including up to four different nucleobases, and having a different size/ length. Each of the different polymers is assigned a uniquely addressed reservoir (e.g., each reservoir is assigned a number between 1 and 10, inclusive, each integer corresponding to a single initiator sequence) and each of the reagents is assigned a unique integer (e.g., 1-4 for each nucleobase, 5-7 for polymerase enzyme and each of two buffers, 8-9 for each of two wash buffers, and 10 for a stop buffer, respectively). Accordingly, in the exemplary method, at least 20 nodes are required as distinct reagent reservoirs on the microfluidic device.

Methods for loading reagents to a specific location or reservoir in a microfluidic device, e.g., an EWOD chip, are known in the art, and the skilled person will understand the loading protocol can vary according to the type and size of microfluidic device that is employed, as well as the force through which droplet isolation and movement are actuated.

a. Conversion of Data to Biopolymer Sequence

In some forms, the methods include providing a biopolymer sequence that encodes a piece of desired information, such as bitstream data. An exemplary sequence-controlled polymer encoding information as bitstream data is a nucleic acid, such as single or double-stranded DNA, or RNA. For example, in some forms, a single-stranded nucleic acid sequence encoding user-defined bitstream data is input for the design of a nucleic acid. In some forms, a portion or portions of a digital format of information, such as an html format of information or any other digital format such as a book with text and/or images, audio, or movie data, is converted to bits, i.e., zeros and ones. In some forms, the information can be otherwise converted from one format (e.g., text) to other formats such as through compression by Lempel-Ziz-Markov chain algorithm (LZMA) or other methods of compression, or through encryption such as by Advanced Encryption Standard (AES) or other methods of encryption. Other formats of information that can be converted to bits are known to those of skill in the art.

Schemes and systems for encoding data in the form of a sequence, such as a biopolymer, are known in the art. Therefore, the described methods can include the step of converting data into or encrypting data within the sequence of one or more biopolymers. For example, in some forms, the step of inputting data includes steps of converting data into a biopolymer sequence. The corresponding sequence is subsequently used as input to coordinate the movement of droplets required for synthesis of the biopolymer.

2. Rendering a Microfluidic Device as a Grid Network

The methods require data input to coordinate the appropriate movement of droplets on a microfluidic device that can actuate movement of sub-microliter volumes of fluid as independent droplets to mediate polymer synthesis. In preferred forms, the microfluidic device is a device for actuating movement of sub-microliter droplets via EWOD. An exemplary EWOD device is an EWOD chip. The initial step in the process includes an assembly process, whereby the chip is rendered as a network grid, representing the relative locations of the channels and reservoirs on the chip.

To coordinate the step-wise assembly process, the chip is rendered as a network grid, representing the relative locations of the channels and reservoirs on the chip. For example, each vertex (node) of the network is represented by a point of intersecting/overlapping grid lines (interacting edges). For example, each vertex (node) of the network is assigned an address based on the intersection of corresponding grid lines. Each node represents the potential position, or destination of a droplet. Each line, or "edge" represents the potential passage of a droplet when it moves between the nodes connected by that edge. An exemplary grid network for a microfluidic device chip is represented in FIG. 1. The schematic in FIG. 1 depicts each channel for fluid movement as an edge on the grid. Each node is addressed according to its relative location. Generally, a fraction of the total number of nodes on a chip are addressed as reservoirs for reagents. The schematic grid represented in FIG. 1 depicts the outermost nodes as reservoirs for reagents. In some forms, the address of each node is determined and automatically assigned from input parameters, for example, a total number of channels on each side of the microfluidic device. Exemplary addressing schemes for each vertex include alphanumeric (e.g., a, b, c and 1, 2, 3, etc.).

The number of nodes available for droplet interface on the microfluidic device is proportional to the number of channels ("edges" in a node-edge network defined by the grid graph of the chip). A grid network having a nodes on one axis and b nodes on another axis (a×b grid graph) has the vertex set [a]×[b], and edges of two types: horizontal edges (i,j),(i+1,j) (of which there are (a−1)b); and vertical edges (i,j),(i,j+1) (of which there are a(b−1)), for a total of ab vertices and (a−1)b+a(b−1)=2ab−a−b edges. In some forms, each node is assigned a single integer value, for example, each node in a 10×10 grid is assigned a number from 1 to 100, inclusive. In some forms, each node is assigned a dual integer address, for example, each node in a 10×10 grid is assigned an address such as (a, 1) or (j, 10), etc.

3. Assigning Unique Addresses to Nodes at Intersecting Grid Lines in the Network In some forms, the channels that define edges of the grid network on the chip are physical channels (e.g., groves or recesses between reservoirs within the microfluidic device). In other forms, the channels are "virtual" channels, for example, where movement of droplets between the nodes of the grid is actuated by optical force.

Employing virtual channels for optical movement of droplets on the microfluidic device grid surface can greatly increase the number of addressed nodes that can be represented on a microfluidic device having defined dimensions, as compared with the potential maximum number of physical channels on a microfluidic device of equal dimensions. Therefore, in some forms, the separation and movement of droplets on the microfluidic device actuated by optical movement of droplets increases the number of "channels" and nodes on the grid relative to the number of nodes and channels on a microfluidic device (e.g., an EWOD chip) of equal size where the droplets are actuated by physical force. Therefore, in some forms, the methods assign a grid network having between 4 and 10,000,000 nodes, inclusive, to a microfluidic device. The number of nodes on the grid network correlates to the number of addressed nodes on the microfluidic device. The number of addressed nodes on the microfluidic device is directly proportional to the number of biopolymers that can be simultaneously synthesized on the microfluidic device. Therefore, in some forms, the methods include providing the addresses of up to 1,000,000 nodes at independent locations at on the same microfluidic device, for example, between 1 and 10 nodes, between 1 and 100 nodes, between 1 and 1,000 nodes, between 100 and 10,000 nodes, between 1,000 and 100,000 nodes.

When a node on the microfluidic device is the location of a reagent reservoir, the address of the node is used as input to direct the automated splitting and movement of droplets containing reagents from the corresponding reservoir. Therefore, the address of a node can be associated with one or more reagents. In some forms, when a node contains one or more immobilized component initiation sequence(s), the address of the node is the address of the corresponding synthesized biopolymer. In some forms, the step of assigning discrete addresses for each location on the grid network of the microfluidic device.

B. Providing Reagents as Discrete Fluid Droplets

The methods require utilizing microfluidic splitting and movement of fluid droplets containing reagents as solutions on a microfluidic device (e.g., actuated by EWOD on an EWOD chip). Therefore, the methods require providing reservoirs of substrates at addressed locations on a microfluidic device.

In some forms, growing biopolymer is immobilized at an addressed location on the microfluidic device. For example, in some forms, the component initiation sequence or the catalyst includes one or more sequences designed to hybridize or otherwise bind to stationary-phase objects such as magnetic beads, surfaces, agarose or other polymer beads. In other instances, the component initiation sequence or the catalyst includes one or more sites for conjugation to a molecule. For example, the component initiation sequence or the catalyst can be conjugated to a protein, or non-protein molecule, for example, to enable affinity-binding of the component initiation sequence or the catalyst, or of the synthesized polymer.

1. Providing Addressed Reagents

The methods include providing reagents as droplets split from larger fluid reservoirs on a microfluidic device. The size, concentration and position of fluid reservoirs is varied according to the reagent, the synthesis protocol, and the dimensions of the microfluidic device.

a. Providing Fluid Reservoirs

The methods include control of reagents as droplets split from larger fluid reservoirs on a microfluidic device. Each fluid reservoir on the microfluidic device can contain one or more reagents. Reservoirs are typically addressed according to the grid of the microfluidic device, and the relative location (address) of the reservoir forms part of the input data used to control and direct the microfluidic device-based synthesis. Parameters of droplets such as the fluid volume and concentration of reagents within each reservoir can be selected according to the specific requirements of the synthesis that is desired. Typically, the volume and concentration of a reagent reservoir used for microfluidic device-mediated fluid movement is proportional to the number, volume and concentration of droplets that are required to be split from the reservoir for synthesis to be completed. An exemplary fluid reservoir volume is between 1 nanoliter (1 nl) and 100 milliliters (100 ml), for example, between about 1 microliter (1 µl) and about 100 microliters (100 µl). A typical synthesis will have 10 µl reservoir containing, for example, 8 µM concentration of each monomer building block in a different reservoir and a reservoir containing 100 µl of buffer, and other 10 µl reservoirs containing 1 µM initiator sequences, and other 10 µl reservoirs containing 10 µM template-free polymerase, such as TdT.

b. Providing Fluid Droplets

The methods include movement and combination of reagents as droplets. Parameters of droplets such as volume and concentration can be selected according to the specific requirements of the synthesis that is desired. Typically, the volume of a droplet used for microfluidic device-mediated fluid movement is between about 0.1 Picoliter (pl), and about 100 microliters (µl), for example, between about 1 pl and about 50 nanoliters (nl). In an exemplary form, each droplet size is between about 0.5 NL and five NL. The concentration of reagents within each droplet is between about 0.1 femtomolar (1 fM) and about 100 micromolar (100 µM). In an exemplary form, the droplets contain reagents for microfluidic device-based synthesis of user-defined addressed nucleic acids. The amount of initiator sequence nucleic acid in a droplet is between about 1 femtomol (1 fmole; $10^{-5}$ moles) and 1,000 picomoles (1,000 pmoles; $10^{-9}$ moles) per 1 picoliter (1 pL) droplet size, up to 5 nanoliter (5 nL) droplet size, and beyond. A typical synthesis will have droplets either of 50 pL or 1 nL with concentrations of the initiator derived from the reservoir or diluted out of the reservoir, approximately 10 µM for the polymerase, 1 µM for the initiator, and 8 µM for the nucleotides, as one example.

C. Combining Droplets to Coordinate Biopolymer Synthesis

The methods include identifying the sequence of movement for reagents necessary to achieve fluid-based template-free synthesis of biopolymers. Typically, the movement enables the splitting, relocation and combination of droplets to achieve the step-wise assembly of the entire biopolymer sequence, based on the address information provided in the corresponding grid network. Therefore, the methods provide routing information for each of the droplets to complete the step-wise assembly of each biopolymer.

Any system that provides control of the coordinated movement of discrete sub-microliter amounts of fluids can be used to synthesis biopolymer according to the described methods. Exemplary systems are microfluidic systems and devices. Exemplary systems that can be employed for the distribution and movement of small fluid volumes as independent droplets according to the described methods include EWOD devices, acoustic droplet distribution devices, such as the commercially available Echo 555, volumetric displacement distribution devices, such as the Mosquito pipette robot, or ink-jet type fluidic distributors. Additionally, the synthesis may occur by flow across a chip, with microwells or synthetic compartments used for synthesis. In a preferred form, microfluidic devices/systems that employ electrowetting on dielectric (EWOD) actuated movement of sub-microliter fluid droplets are used for synthesis of biopolymers according to the described methods.

Methods for optical fluid motion are known in the art. In some forms, the methods employ fluid motion that results from the dynamic thermal expansion in a gradient of viscosity. For example, the viscosity of a fluid at a given spot is reduced by its enhanced temperature. This leads to a broken symmetry between thermal expansion and thermal contraction in the front and the wake of the spot. As result the fluid moves opposite to the spot direction due to both the asymmetric thermal expansion in the spot front and the asymmetric thermal contraction in its wake.

1. Electrowetting on Dielectric (EWOD) Techniques

In some forms, the assembly of biopolymers through step-wise addition of user-defined building block components occurs through EWOD-mediated movement of droplets containing substrates, enzymes, wash buffers and other reagents. The extent and direction of the movement of each droplet coordinates the combination of two or more droplets at any given location on the EWOD chip. The methods render an EWOD chip as a grid, with each discrete location at the intersection of one or more of the grid lines as a distinctly addressed location on the chip. Therefore, movement of droplets from one discrete addressed location on the EWOD chip to another discrete addressed location on the chip can be carried out as a computer-readable program to synthesize biopolymers having a programmable user-defined composition.

Electrowetting describes the electromechanical reduction of a liquid's contact angle as it sits on an electrically-charged solid surface. When an electric field is applied across the interface between a solid and a water droplet, the surface tension of the interface is changed, resulting in a change in the droplet's contact angle. In oil ambient (i.e., when the water droplet is surrounded by oil rather than air), the electrowetting effect can provide >100° of reversible contact angle change with fast velocities (>10 cm/s) and low electrical energy (~100 to 102 mJ/m² per switch).

Electrowetting has become one of the most widely used tools for manipulating tiny amounts of fluids on surfaces. A large number of applications based on electrowetting have now been demonstrated, including lab-on-a-chip devices, optics, and displays.

An important parameter in electrowetting studies is Young's angle ($\theta Y$), defined as follows:

$$\cos \theta Y = (\gamma od - \gamma ad)/\gamma ao \quad (1)$$

where; $\gamma od$ is the interfacial tension between the electrowetting liquid (a, typically aqueous) and the oil (o) surrounding the electrowetted liquid; $\gamma ad$ is the interfacial tension between (a) and the dielectric layer (d); and $\gamma ao$ is the interfacial tension between (a) and (o).

For most electrowetting applications, it is generally desirable to use low voltages (V) to switch from Young's angle to the electrowetted contact angle ($\theta V$). Low-voltage operation is particularly important for particular displays, such as e-paper displays, that require very large arrays (thousands or millions) of electrodes. These devices require active-matrix electrode control. Active matrix control makes use of thin film transistors (TFTs) that independently address each of the pixel states. TFTs typically provide reliable operation up to about only 15V. However, achieving reliable electrowetting devices operating at ≤15V has been a considerable challenge.

In an electrowetting system, Young's angle is reduced to the electrowetted contact angle (θV) as predicted by the electrowetting equation, $$\cos \theta V = (\gamma od - \gamma ad)/\gamma ao + \varepsilon V2/(2d\gamma ao) \quad (2)$$

where: $\varepsilon$ is the dielectric constant and d is the thickness of the dielectric; $\gamma$ is used for terms denoting the interfacial tension between the electrowetting liquid, the oil, and the dielectric, as described in equation 1, above; and V is the applied DC or AC RMS voltage.

Once surface tensions are optimized for a high Young's angle ($\theta Y$), the electrowetting equation predicts that lower voltages may be obtained only by reducing the thickness of the dielectric, or by using a dielectric with a higher dielectric constant. A change in contact angle on the order of 100 degrees is desirable for good electrowetting device function.

The methods require control of movement of reagents as droplets split from larger fluid reservoirs on an EWOD chip. Mechanisms for controlling extent and direction of movement of droplets using EWOD technology are known in the art. Exemplary mechanisms for actuating movement of droplets include electrical charge and optical control systems.

a. Optical Electrowetting Techniques

In some forms, movement of droplets on EWOD is actuated by an optical force. By optically modulating the number of carriers in the space-charge region of the semiconductor, the contact angle of a liquid droplet can be altered in a continuous way. This effect can be explained by a modification of the Young-Lippmann equation. Exemplary methods for optical movement of droplets include optoelectrowetting, and photo-electrowetting. Optical (light-manipulated) EWOD technology offers full programmability of droplet movement at the single-droplet level for up to millions of droplets simultaneously and instantaneously. An exemplary technology is the, OPTOSELECT™ technology, that uses low-intensity visible light to precisely manipulate cells, beads and reagents, commercially available from Berkeley Lights. OPTOSELECT™ consumable chips contain thousands of nanoliter pens, allowing the annotation and characterization of individual droplets.

i. Opto-Electrowetting

Optoelectrowetting (OEW) involves the use of a photoconductor. Where traditional electrowetting runs into challenges, however, such as in the simultaneous manipulation of multiple droplets, OEW presents a lucrative alternative that is both simpler and cheaper to produce. OEW surfaces are easy to fabricate, since they require no lithography, and have real-time, reconfigurable, large-scale manipulation control, due to its reaction to light intensity.

By shining an optical beam on one edge of a liquid droplet, the reduced contact angle creates a pressure difference throughout the droplet, and pushes the droplet's center of mass towards the illuminated side. Control of the optical beam results in control of the droplet's movement.

Using 4 mW laser beams, OEW has proven to move droplets of deionized water at speeds of 7 mm/s. Traditional electrowetting requires a two-dimensional array of electrodes for droplet actuation. The large number of electrodes leads to complexity for both control and packaging of these chips, especially for droplet sizes of smaller scales. While this problem can be solved through integration of electronic decoders, the cost of the chip would significantly increase ii. Photo-Electrowetting Photoelectrowetting (PEW) uses a photo capacitance and can be observed if the conductor in the liquid/insulator/conductor stack used for electrowetting is replaced by a semiconductor.

Photoelectrowetting using the photo capacitance in a liquid-insulator-semiconductor junction is achieved via optical modulation of carriers in the space charge region at the insulator-semiconductor junction that acts as a photodiode—similar to a charge-coupled device based on a metal-oxide-semiconductor. Droplet transport is achieved by focusing a laser at the leading edge of the droplet. Droplet speeds of more than 10 mm/s can be achieved without the necessity of underlying patterned electrodes.

In some forms methods for synthesis of biopolymers on EWOD employ photoactivated electrowetting-actuated movement of droplets. Typically, the methods employ a hydrophobic surface to enable movement of sessile droplets. An exemplary system for PEW includes a photoactive wafer that can be photoactivated to induce an electric field covered with a dielectric which actuates the droplet.

b. EWOD Synthesis on Solid Support

In some forms, a growing biopolymer is immobilized at an addressed location on the EWOD chip, such that movement of the biopolymer is not mediated by EWOD. For example, in some forms, the component initiation sequence or the catalyst includes one or more sequences designed to hybridize or otherwise bind to solid support or stationary-phase objects such as magnetic beads, surfaces, agarose or other polymer beads. In other instances, the component initiation sequence or the catalyst includes one or more sites for conjugation to a molecule. For example, the component initiation sequence or the catalyst can be conjugated to a protein, or non-protein molecule, for example, to enable affinity-binding of the component initiation sequence or the catalyst, or of the synthesized polymer.

When a solid support or stationary-phase object is used, the mechanism for moving droplets is distinct from, and does not induce movement of the solid support or stationary-phase object, such that droplets can be moved onto, or split from the immobilized reagent(s).

2. Providing Input for Microfluidic-Based Synthesis

In some forms the methods include inputting instructions for the movement of droplets on the pre-defined network grid of the microfluidic device to assemble each user-defined polymer using a computer-based interface. For example, in some forms, data corresponding to the addressed nodes of the network are input to a computer for the automated synthesis of one or more biopolymers on the microfluidic device.

Methods for inputting coordinates of a grid network in computer-readable form are known in the art. For example, in some forms the methods include providing the geometric parameters that define the grid network on the microfluidic device and/or the address of each reservoir of a reagent required for the synthesis of each biopolymer. Geometric parameters include the spatial coordinates of all vertices, the edge connectivity between vertices, and the faces to which vertices belong.

The extent of automation of control of microfluidic device-mediated movement of droplets can be varied from complete automation (e.g., random selection of target sequence and size, based on pre-determined grid coordinates for a microfluidic device having pre-addressed reservoirs having standard volumes of each reagent), to no automation (each step of droplet splitting and node to node movement of droplets is user-defined for a user-defined grid custom designed to include user-supplied reagents). In some forms, the input data includes only the address of each immobilized component initiation sequence (i.e., the location at which each biopolymer will be synthesized), and the desired target sequence. Input data controlling movement of droplets to achieve the cycle of adding each component building block (e.g., coordinated washing, adding component building blocks, catalysts, blocking catalysts), the number of cycles required, etc. is pre-programed, or otherwise provided independently. In other forms, input data controlling each node-to-node movement of a droplet throughout the entire synthesis process is also input, for each biopolymer.

Following sequence design, grid-determination and input of the instructions necessary for the microfluidic device-based synthesis of biopolymers according to the described methods, the addressed biopolymer sequences are synthesized, optionally functionalized and purified on the microfluidic device. Therefore, methods for the microfluidic device-based template-free synthesis of biopolymers having user-defined sequence include the step of producing the biopolymers. In some forms, the methods simultaneously synthesize up to 1,000,000 biopolymers at independently addressed locations on the same microfluidic device, for example, between 1 and 10 polymers, between 1 and 100 polymers, between 1 and 1,000 polymers, between 100 and 10,000 polymers, between 1,000 and 100,000 polymers.

Typically, parameters are determined as input data for each synthesis. Exemplary parameters include (a) the sequence of movement of droplets to contact the initiator sequence with each reagent in the appropriate order for synthesis of the desired biopolymer sequence, as well as (b) the conditions required for optimal activity of the reagent at each step of the synthesis.

Typically, the methods attach component building blocks to an initiator to synthesize a biopolymer having a user-defined sequence of component building blocks. Because the number of component building blocks that is attached to growing biopolymer cannot be controlled at the level of each individual molecule, the resulting biopolymers produced by each complete synthesis will typically include a bell curve for the number of component building blocks attached to the biopolymer molecules during each cycle. For example, in some forms, each attachment reaction may attach between zero and one hundred component building blocks to the initiator or biopolymer. Typically, the average number of component building blocks attached at each stage is one or two. In some experiments, the average number of component building blocks attached at each stage is eight and follows a Poisson distribution around 8 additions. Typically the number of homopolymer additions is controlled by the amount of precursors available and the ratio between the growing polymer and the available nucleotides, and the temperature of operation, and the buffer used, and the enzyme used. In some forms, the distribution of the number of building blocks attached at each stage is controlled, for example, by limiting the factors that enhance the attachment process. Exemplary factors that can be controlled include the concentration of substrates, catalysts, ions, and other reagents, as well as incubation times, and variation of other factors including light, agitation, temperature, pressure, electrical charge, etc.

In some embodiments, the time of each reaction step is determined by simulating the Michaelis-Menten equation for estimating the nucleotide usage. In further embodiments, the estimation of the number of additions needed to differentiate one sequence controlled polymer from another is determined by simulating the number of additions assuming a Poisson distribution.

In some embodiments, the addition of the nucleotide is blocked by optically activatable nucleotide analogs. In one implementation, the nucleotides or addressed strands will become activated to allow for the next incorporation by the specific projection of light, such as from a DLP chip (Texas Instruments). In some implementations, the specific nucleotide or polymer will be activatable based on the wavelength of the light used, such that some polymers or nucleotides become active only when, for example, blue light is used.

a. Sequences and Cycles of Droplet Movement

The assembly is carried out by step-wise movement of fluid droplet on a suitable microfluidic device surface. In preferred forms, the movement of droplets is carried out using a EWOD device. Movement of droplets on an EWOD device can be actuated by application of electric charge, or by optical force. Movement includes splitting of droplets from larger volumes, for example, to provide discrete volumes of reagents that are mixed in the appropriate quantities in an appropriate reaction volume to control attachment and biopolymer synthesis. In preferred forms, the reagents are split and combined in an amount effective to maximize the yield and correct assembly of the biopolymer.

The examples of DNA polymer synthesis can generally be applied to DNA or RNA synthesis using alternative enzymes such as Telomerase or Qbeta replicase. Additionally the examples herein describe droplet-based movement using EWOD, but are generally applicable to droplet merging, separating, and mixing offered by other devices such as through optical control, for example using fluid moved by a laser-scanning microscope.

In some forms, the methods initiate and complete synthesis of a biopolymer by step-wise addition of reagents to an initiator sequence that is maintained at a single location on a microfluidic device. In other forms, initiation and completion of the synthesis of a biopolymer by step-wise addition of reagents to an initiator sequence includes microfluidic device-based movement of a droplet containing the initiator sequence and growing biopolymer. Synthesis can be carried out in aqueous solution without a solid support or matrix, or can include one or more reagents immobilized onto a solid support or matrix.

In other forms, a growing biopolymer is immobilized at an addressed location on the microfluidic device. For example, in some forms, the component initiation sequence or the catalyst includes one or more sequences designed to hybridize or otherwise bind to solid support or stationary-phase objects such as magnetic beads, surfaces, agarose or other polymer beads. In other instances, the component initiation sequence or the catalyst includes one or more sites for conjugation to a molecule. For example, the component initiation sequence or the catalyst can be conjugated to a protein, or non-protein molecule, for example, to enable affinity-binding of the component initiation sequence or the catalyst, or of the synthesized polymer.

When a solid support or stationary-phase object is used, the mechanism for moving droplets is distinct from, and does not induce movement of the solid support or stationary-phase object, such that droplets can be moved onto, or split from the immobilized reagent(s).

In an exemplary form, a sequence of microfluidic device-mediated splitting, movement and combination of droplets enables assembly of a nucleic acid from fluid reservoirs containing an enzyme catalyst, component building blocks (e.g., nucleotides), and a component initiation sequence (e.g., oligonucleotide), respectively. In a first movement, droplets are simultaneously split from the enzyme (E+I), and one or more nucleotide (N1T, N2T, etc.) reservoirs. In a second movement, the droplets are merged to form a combined droplet. The combined droplet is incubated for 1 minute to achieve the reaction forming a product ("N1"). In a third movement, the droplet containing N1 is moved to the next droplet containing the next nucleotide reagent. The movement of droplets to split, steer, and merge fluids can be actuated by electrical potential (e.g., as in an EWOD device), or by optical excitation.

Typically, input parameters include instructions for the electrical or optical actuated initiation (splitting of a droplet from a reservoir), and directional of node-node movement of a droplet. The input parameters also include the amount of time between subsequent movement or splitting events at any given node (address on the grid). Therefore, parameters such as incubation time, amount of reagent added or removed, and the total volume of droplets at each location can be controlled, either directly, or as a pre-programmed template of instructions for each microfluidic device.

i. Solid Support-based Synthesis

In some forms, the methods synthesize biopolymers from multiple consecutive cycles of step-wise assembly of the component building blocks from an initiator sequence that is coupled to a solid support. The solid support can be a particle, such as a bead, that is loaded onto or otherwise present on the microfluidic device, or it can be a surface of the microfluidic device. The initiator sequence can be coupled to the solid support using any bond, material, or system known in the art for conjugating molecules together. In a preferred form, the initiator sequence is coupled to a solid support using the biotin/streptavidin conjugation system, for example, via a biotin sequence at the 5' region of the initiator tag (i.e., 5'-biotinylated initiator sequence).

An exemplary sequence of movement includes the steps of (1) combining a component building block with an initiator sequence; (2) combining an attachment reagent with the droplet containing a component building block with an initiator sequence to form an attachment reaction droplet; (3) optionally combining a buffer with the attachment reaction droplet to initiate, enhance or otherwise control the attachment; (4) combining a stop reagent with the attachment reaction droplet to stop the attachment; (5) optionally combining a wash reagent with the reaction droplet to create a washed reaction droplet; (6) splitting the majority of the washed reaction droplet to create a waste droplet and a washed biopolymer droplet; and repeating step (5) one or more times to thoroughly wash the biopolymer. Generally, the cycle including each of steps (1)-(6), above, is repeated for the addition of each component building block to the developing biopolymer.

Therefore, in some forms, the number of cycles required to construct the biopolymer is equal to the size of the sequence that is synthesized.

Each of the movement steps (1)-(6), above, can be further characterized by the sequence of (i) splitting of a droplet containing the fluid from the corresponding reservoir; (ii) moving the droplet to the location of a target droplet; and (iii) combining the droplet with the target droplet. In some forms, the target droplet contains the biopolymer, or the initiator. In other forms, the target droplet does not contain the biopolymer or the initiator. Therefore, in some forms each movement step can involve multiple steps of splitting, moving, and combining, for example, to prepare a droplet having a desired composition prior to combining with the biopolymer or the initiator.

One or more of the catalyst enzyme and/or initiator sequence can be immobilized or attached to one or more solid support matrices. In some forms, the addressed synthesis is carried out on a passivated surface or slide, for example, a slide that has the initiator and polymer on a surface, or in a picoliter-scale well etched into a slide. In some forms, the initiator sequence or the attachment enzyme is attached to a surface or a well by, for example, biotin, or other methods known in the art. In some forms, the initiator sequence and enzyme will be accessible to a lateral flow of washing solution or component building blocks (e.g., nucleotides). In such cases, the addressed growing strand will be programmed for the next incorporation by focused light on the surface using, for example, a 4 k DLP chip.

In some embodiments, the synthesis of the polymer will occur within a well or micrometer scale vesicle separated from an outside environment by the presence of a lipid bilayer or polymer mesh. In such embodiments, the mesh or layer can allow or disallow the crossing of building blocks by an external motive force, such as by electroporation or electrophoresis. This again can be addressed by circuit based design, creating the potential needed to allow for crossing the barrier to entry into the encapsulated region. In such cases, the encapsulated region would be 1-10 micrometers, and be similar to synthetic cells. In such cases, the growing polymer may be DNA or proteins or RNA and may encoding for genetic or information elements.

ii. Continuous Flow-Based Synthesis

Attaching the polymerase or catalyst or component initiation sequence to the surface of a chip by passivating the chip using techniques known in the art additionally allows continuous flow incorporation of component building blocks (e.g., nucleotides) to the growing polymer. In some forms, the initiator sequence and enzymes are segregated in different wells having micro-meter or nano-meter dimensions, with single polymerases and initiators within the well. Flow of the individual monomers can be controlled or diverted using electronic switches, heating, or through lithographic plates, or through coverage with lipid bilayer with or without embedded protein channels. Access to the well/solution containing the enzyme is controlled in order to direct synthesis of the biopolymer. Exemplary methods to control access to the well/solution containing the enzyme include direct penetration through the membrane or cover of the well, or by activating one or more channels through the cover or membrane.

In some forms, combining single or multiple component building blocks with the well/solution containing the enzyme is accomplished through activating a potential, for example, by using electric potential across the membrane to allow for the flowing nucleotides to pass through the surface (similar to electroporation that is well known, but in a micro- or nano-scale well) or by inducing an electric signal to activate a protein channel, or an electric potential that causes nucleotide or negatively charged monomers, or positively charged monomers to pass inside of an otherwise closed surface, such as electroporating through agarose, acrylamide, or other polymers. Therefore, in some forms, the well contains the initiator or growing polymer and polymerase that cannot pass out of the well due to blockade from a bilayer or chemical mesh. In some forms one or more of the channels may be optically controlled for nucleotide or polymer layer crossing using optical patterning.

iii. Solution-Based Synthesis

In some forms, the growing polymer is not affixed to beads or a surface, but is free in solution. For example, in some forms the droplet containing the initiator sequence will sequentially increase in volume with the addition of each reagent droplet throughout the synthesis process.

b. Incubation Conditions

The methods employ different conditions to achieve synthesis of biopolymers. In preferred forms, the sequence of splitting, moving and combining fluid droplets is interspersed with incubation periods to synthesize a biopolymer through cycles of steps (1)-(6), above. The incubation conditions can include changes to one or more parameters. Therefore, in some forms, incubation periods include changing or manipulating one or more physical or chemical parameters, such as temperature, ionic concentration, pH, pressure, charge, exposure to light, etc. In a preferred form, incubation conditions are used to control the attachment of a component building block to an initiator, for example, to enhance or optimize, or reduce or prevent the attachment.

In some forms, the methods include specifying optimal conditions for attachment of each component building block. Therefore, parameters of the droplet can be varied, including volume, concentration etc., and external parameters, including incubation time, temperature, etc. can be varied to control, optimize or minimize one or more aspects of the assembly process.

Exemplary incubation conditions include the conditions that produce the most effective results, as determined by the goal of the step of moving droplet, combining two or more droplets, or splitting a droplet. In an exemplary form, the goal of combining an attachment reagent with an initiator or a biopolymer and a component building block is optimized by enhancing the attachment of a single component building block to the initiator or biopolymer. Therefore, optimal conditions include those which most effectively achieve the attachment. Exemplary steps that can be optimized include optimal conditions for catalysis of attachment ("attachment conditions"), optimal conditions for stopping or blocking a reaction ("stop conditions", and "blocking conditions"), and optimal conditions for rinsing, dissolving or washing reagents ("wash conditions"). Typically, parameters that can be varied for each set of conditions include (i) incubation volume, (ii) incubation time, and (iii) other conditions, such as those external from or independent of the droplet. Each of these parameters can be optimized by one skilled in the art.

i. Incubation Volume

The methods include mixing of droplets of different sizes, or the same size. Therefore, the methods can vary the amount and concentration of the reagents after combination of two of more droplets (i.e., the "final" concentration).

In an exemplary form, a volume of a buffer, or attachment reagent is split from the corresponding reservoir and moved to combine with a droplet containing an initiator sequence, or a biopolymer, or a bead with the initiator sequence, or biopolymer bound thereto, in an amount sufficient to produce a desired concentration in the resulting droplet. For example, a droplet can be increased in size until a desired concentration of reagent(s) is reached. In some forms, a droplet including an active agent is combined with a droplet containing no active agent, such as a buffer or water droplet, to dissolve the active agent and/or reduce the concentration to a desired value. This droplet is subsequently combined with a droplet containing an initiator sequence, or a biopolymer. In this manner, the methods enable the user-defined creation of droplets of specified volume having a specified concentration of reagent(s), pH, ionic strength, etc. Therefore, in some forms, the methods include the step of creating droplet having a defined concentration, pH, salt concentration, amount of active agent, etc. prior to combining with the droplet containing an initiator sequence, or a biopolymer. In this manner, specific concentrations of reagents can be combined with the addressed biopolymer throughout the assembly process, for example, to control the rate and extent of attachment of a given building block, or to block enzyme activity.

In an exemplary form, the concentration of a component building block within a droplet is reduced such that only one or more such component building block are added to the initiator sequence, or terminal end of the biopolymer per cycle. Therefore, in some forms, the concentration of the component building block in the combined droplet determines the number of component building blocks that is added to the biopolymer per cycle.

In another form, the concentration of salt or pH in the combined droplet is used to control enzyme activity. For example, the amount of salt and pH in a droplet can effect the rate and fidelity of an enzyme-catalyzed addition reaction. Therefore, in some forms, droplets including a catalyst are combined with droplets including an amount of salt or a salt-free buffer sufficient to reduce or increase the salt concentration in the combined droplet such that the activity of an enzyme catalyst is reduced, increased, prevented or initiated. For example, in some forms the concentration of salt within the combined droplet is increased to an amount effective to initiate the activity of a catalyst. In other forms, the concentration of salt within the combined droplet is reduced to an amount effective to prevent the activity of a catalyst.

Typical incubation volumes are volumes between about 0.1 Picoliter (pl), and about 100 microliters (µl) (but can be larger), for example, between about 1 pl and about 50 nanoliters (nl). In an exemplary form, each droplet size is between about 0.5 nl and 5 nl.

ii. Incubation Time

The methods include combining droplets to form a larger combined droplet at a given location for a specific period of time. After two or more droplets are combined, they can be split, for example, to produce a large droplet of solvent and a smaller volume that includes the immobilized biopolymer, after a certain time period, for example to isolate the biopolymer form attachment reagents.

Therefore, in some forms the methods combine reagents for a specific period of time, for example, sufficient to achieve the goal of the combining step. Exemplary incubation times include one or more milliseconds (ms), one or more seconds, for example, 5 seconds, 10 seconds, 30 seconds, 40 seconds, 50 seconds, 1 minute, 2 minutes, 3 minutes, 5 minutes, 10 minutes, 20 minutes, 30 minutes, 45 minutes, 1 hour, 90 minutes, 2 hours, 3 hours, 6 hours, 12 hours, 24 hours or more than 24 hours. In some forms, the incubation time is determined according to the specific reactivity of the enzyme, reagent or catalyst that is required. For example, in some forms, the amount of time an attachment agent is incubated with an initiator or biopolymer and one or more component building blocks is varied to limit the number of component building blocks that are attached. In an exemplary form, two of more droplets of reagents are combined for a period of time between 30 seconds and 5 minutes. An exemplary incubation time for catalysis of attachment of a nucleotide component building block to a nucleic acid by the TdT enzyme is 10 minutes at 37° C.

iii. Other Conditions

The methods include mixing of droplets under different conditions to achieve optimal incubation parameters. Therefore, the methods can vary the conditions under which the reagents are combined, for example, to provide different amounts of heat, light, gas, electric charge, etc. In some forms, incubation is enhanced by mixing the combined droplets, for example by agitation of the support surface. An exemplary temperature for incubation of droplets for enzymic attachment is between 20° C. and 40° C., for example 37° C. An exemplary temperature for reducing or preventing the activity of a catalyst enzyme is a temperature greater than 40° C. for example, a temperature between 60° C. and 80° C. The temperature at a given location during the synthesis of a biopolymer can be controlled, for example, by a Peltier temperature control system. In some implementations the droplet is moved to a location on the grid that can be held at 37° C. from 1 second to 30 minutes, or for example 10 minutes. In another implementation, a mobile heat block can be moved in that sits at the base of the microfluidic channels that heat the channels to 37° C., or the desired operating temperature. In another implementation, the device is placed in a room that operates at 37° C. or the desired operating temperature.

c. Inhibition of Catalyst Activity

In some forms, the methods include the step of inhibiting the catalyst activity. Inhibiting the catalyst can include a process that reduces or prevents the addition of a component building block onto the biopolymer. Inhibiting the catalyst activity can be achieved by means including active inhibition of the catalyst enzyme; removal, or reduction in the amount of, one or more essential enzyme co-factors; removal, or reduction in the amount of, one or more component building blocks; disruption or degradation of the catalyst enzyme; physical separation of the biopolymer from the catalyst enzyme; and combinations of these. Therefore, in some forms, the methods inhibit the activity of the catalyst by combining the droplet including the biopolymer with one or more droplets including a reagent or molecule that inhibits or reduces the activity or presence of the enzyme.

In some forms the methods inhibit the activity of the catalyst by combining one or more inhibitory molecules into the biopolymer. The inhibitory molecules can reversibly block the incorporation of subsequent component building blocks onto the biopolymer. Therefore, in some embodiments, the methods coordinate the sequence-specific synthesis of biopolymers by employing a sequence of steps to (i) activate or combine, (ii) inhibit or remove, and (iii) re-activate or recombine the catalyst enzyme. In some forms, the step of activating the catalyst (for example, in the presence of a first component building block) includes one or more processes such as combining droplets including enzyme co-factors, buffers, or other reagents necessary for catalyst function. In some forms the activation step incudes incubating the combined droplet, for example, for a specified time, at a specified temperature, etc. In some forms the step of inhibiting the catalyst includes one or more processes such as combining droplets with reagents that chelate, sequester or otherwise remove the enzyme co-factors, buffers, or other reagents necessary for catalyst function. In some forms the inhibition step incudes incubating the combined droplet, for example, for a specified time, at a specified temperature, etc. to ensure the activity of the catalyst is inhibited. In some forms the step of reactivating the catalyst (for example, in the presence of a second component building block) includes one or more processes such as combining droplets with reagents including enzyme co-factors, buffers, or other reagents necessary for catalyst function.

In some forms the inhibition step includes the addition of one or more inhibitory component building blocks to the biopolymer, for example, an inhibitory nucleic acid that includes a charged moiety which sterically hinders the activity of the catalyst enzyme. Therefore, in some forms, the step of reactivating the catalyst activity includes removal of the charged moiety from the inhibitory nucleotide.

In some forms, the sequence of (i) activating or combining the catalyst, (ii) inhibiting or removing the catalyst, and (iii) reactivating or recombining the catalyst include one or more wash steps. For example, in some forms, one or more wash steps are carried out between (i) and (ii), between (ii) and (iii), between (i) and (iii), or between each of (i), (ii) and (iii).

In an exemplary form, the component building blocks are all inhibitory nucleic acids. Therefore, in some forms, every step for the addition of a component building block to the biopolymer includes (i) and (iii), above. For example, the step of reactivating the catalyst includes removal of the inhibitory moiety from the previously added nucleic acid.

In an exemplary form, the method employ a stop reagent that is a chelating agent that removes cations from the solution containing the catalyst enzyme. Therefore, in some forms the methods combine the use of limiting concentrations of catalysts and/or component building blocks with chelating agents to provide precise control over the number of component building blocks that is added to a biopolymer at each "cycle", for example to incorporate one, two, three, or four component building blocks to the growing biopolymer. Therefore, in some forms, the methods include stop reagents that provide precise control over the length and sequence of the biopolymers that are synthesized. Therefore, in some forms, the methods do not produce biopolymers having a range of sizes and sequences according to a binomial distribution.

3. Exemplary Methods

Exemplary methods for the microfluidic device-based synthesis of user-defined nucleic acids are provided. The exemplary methods synthesize nucleic acids in a highly parallel manner using template free enzymatic synthesis of DNA by using the addition of nucleotides, enzymes, washing solution, and blocking solutions through programmed movement with droplet-based microfluidic device technology. The exemplary methods define the sequences of movement and parameters required for template-free assembly of nucleic acids using TdT enzyme as an attachment agent. The exemplary methods employ grid-based EWOD as one method of droplet technology, but can be generalized to discrete grid-based movement of droplets by any applied potential, such as through circuits or through optics, or any continuous induced movement of droplets from such a system. Therefore, the exemplary methods can be generalized for use with any system that employs droplets of 1 pL, up to 1 µL to be split, merged, or mixed. The exemplary methods employ dNTPs (for example, ATP, UTP, GTP, and CTP) as component building blocks for user-defined nucleic acid sequences. The methods can be used to attach any bases known to the art that are recognized and can be attached by TdT polymerase.

Exemplary methods include (a) EWOD-based Synthesis of Nucleic Acid on solid support; (b) EWOD-based Synthesis of Nucleic Acid using immobilized TdT enzyme; (c) EWOD-based Synthesis of Nucleic Acid in Solution; and (d) encoding data within biopolymer sequences, are provided below.

a. EWOD-Based Synthesis of Nucleic Acid on Solid Support

In an exemplary method, EWOD-based synthesis is employed for template-free synthesis of a user-defined nucleic acid, using an initiator sequence specific for the Terminal deoxynucleotidyl transferase (TdT) polymerase enzyme coupled to a magnetic bead.

When deoxyribonucleotides polymerize to form DNA, the phosphate group from one nucleotide will bond to the 3' carbon on another nucleotide, forming a phosphodiester bond via dehydration synthesis. New nucleotides are always added to the 3' carbon of the last nucleotide, so synthesis always proceeds from 5' to 3'. An initiator sequence for the TdT enzyme is attached to magnetically active beads or directly to a surface by binding to the beads or surface modified with streptavidin. The concentration is generally between about 1 fmol and 100 picomole per 1 pL droplet size, up to 5 nL droplet size, or larger, for example, up to 1,000 nL.

The magnetic beads are held in place by the presence of a magnet external to the surface of the EWOD chip. The affixed DNA initiator sequence is maintained in aqueous solution throughout the synthesis. The aqueous solution can be any aqueous solution suitable for maintaining the synthesized nucleic acid. Using programmed droplet movement offered by EWOD, component building blocks are sequentially added to the immobilized initiator sequence by movement of a droplet containing the desired nucleotide. Exemplary dNTPs include canonical dATP, dTTP, dGTP, or dCTP, and non-canonical dNTPs. A droplet containing the selected component building block is split from the corresponding reservoir, and then moved across the grid network to the location (address) of the fixed strand droplet. Upon contacting the droplet containing the fixed strand, the combined droplets are mixed. In some forms, the incoming droplet containing the dNTP component building block may also contain buffering and salt components for the reaction and additionally TdT enzyme. Alternatively, the TdT enzyme could be separately mixed with the stationary droplet before or after the addition of nucleotides.

After mixing of the nucleotides with the growing DNA polymer and with the addition of buffer and enzyme, the addition of nucleotides to the growing affixed polymer to begin. The time for incorporation is generally from 1 second to 1 minute, and the number of additions of nucleotides as a homopolymer to the affixed polymer is determined by (1) temperature, (2) time in total solution, (3) presence of blocking moieties on the dNTP that was added, and (4) the amount of dNTP that were added to the total solution. In case 1, the temperature can be modified from 4° C. to 98° C. which has an effect on enzyme incorporation rates. Current standard operating temperatures are 37° C. The time the affixed growing polymer is subjected to the dNTPs and/or enzyme is also a factor for number of incorporations. By incubating the polymer with the enzyme and dATP (for example) for 1 minute at 37° C., incorporation of 1 to 10 to 100 homopolymer A's would assemble to the affixed polymer. The time that the affixed strand is subjected to the dNTPs can be controlled by removing and washing the fixed-position polymer away from the dNTPs. The presence of blocking nucleotides which can be modified at, for example their 2' or 3' position, can additionally be used to limit the length of the growing polymer, which can be achieved by having these modified nucleotides in the dNTP mix itself, or have them in high concentration in an external droplet that is moved into and mixed with the solution. Finally, the homopolymer addition of dNTPs can be limited by the concentration of the dNTPs, wherein the droplet might contain 1 pmol of dATP (for example) added to a droplet containing 1 pmol of affixed polymer. Thus, addition of the nucleotides will diminish to nothing as they are incorporated, and the number of additions per homopolymer will have a Poisson distribution around a single nucleotide incorporation.

Sequences of chosen length will finally be released by low-salt, heating, or cleaving with a nuclease-specific cut site incorporated 5' of the component initiation sequence (e.g., PstI), or will be amplified using polymerase chain reaction (PCR) off the chip. Alternatively the DNA polymer will not be released from the bead or surface, but will remain bound for further processing.

Ease of subsequent sequencing of ssDNA can be achieved by prepending or appending the SMRTbell (PacBio) polymerase sequence to the 5' or 3' of the growing DNA strand, or the component initiation sequence for nanopore sequencing (Oxford Nanopore). This allows for direct sequencing through adaptation to already discovered methods of sequencing.

b. Exemplary Method for EWOD-based Synthesis of Nucleic Acid using immobilized TdT enzyme In some forms, the template-free polymerase (e.g. TdT) is affixed to a solid support by biotin moieties or by cloning with streptavidin, or other methods of fixation known to the art. Furthermore, the enzyme (e.g. TdT) is additionally modified to enhance binding to the growing single-strand polymer, such as by cloning at the N-terminus or C-terminus a single-stranded DNA binding protein such as SSB, or zinc-finger domains. Thus the polymerase is affixed to a solid support (bead, surface) and the template is attached non-covalently to the template-free polymerase by interaction with a second domain. The addition of the nucleotides will then catalyze the addition and all methods applied in example 1 could be applied here for sequence control of the growing polymer.

c. Exemplary Method for EWOD-based Synthesis of Nucleic Acid in Solution

Starting with a low-volume, high concentration of Enzyme and initiator sequence, the addition of the dNTPs will be sequence-specified and in a concentration such that depletion will be limiting with each addition. Therefore if dATP (for example) was added to the enzyme and polymer mix at a 1:1 concentration, the dATP would be depleted over additions with a Poisson distribution of 1 A added per polymer. After reaction depletion, for example in 1 min at 37 C, the next nucleotide would be added and mixed to the solution, also in 1:1 amounts. Thus a growing, sequence-controlled DNA polymer could be made without affixing to a solid support and without requiring washing or removal of dNTPs.

Figure 2:
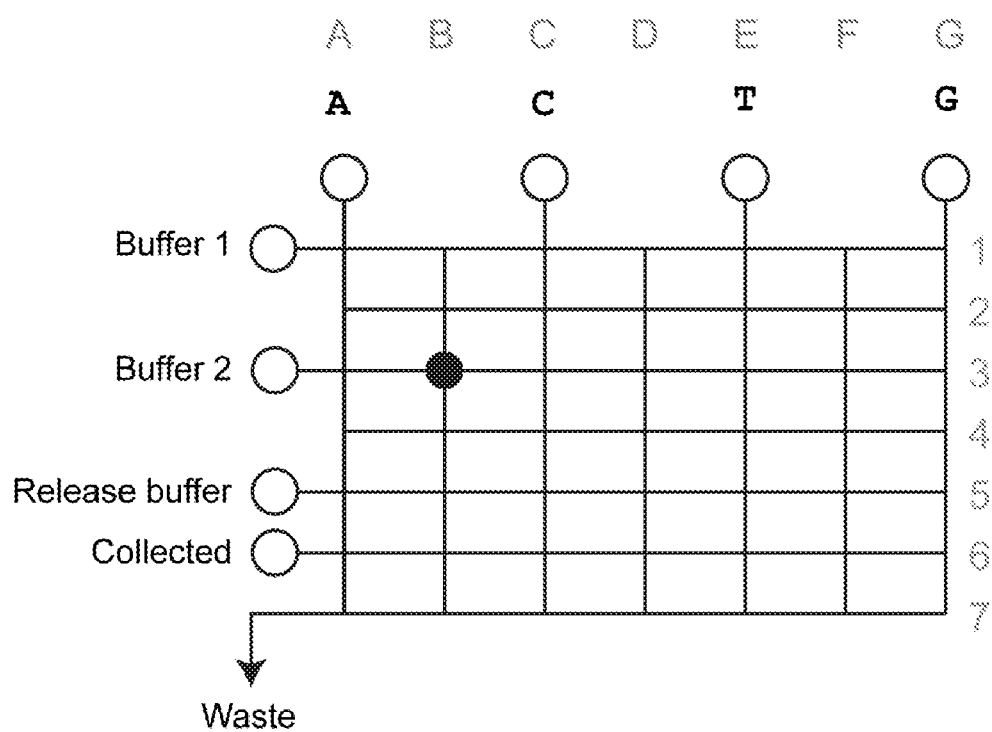
FIG. 2 is a schematic of movement of the droplets from necessary to synthesize a DNA fragment of sequence ATCG. This sequence of moves can be generalized to any nucleic acid sequence incorporation. It is shown with 4 wells containing dATP ("A"), dTTP ("T"), dCTP ("C"), and dGTP ("G"), 2 buffer wells, a release solution well, a collector output port, and a waste port. A magnetic bead with streptavidin bound to a biotinylated initiator strand is at B-3. Each of A, T, C, and G also contain buffer, salt, and template free polymerase (e.g., TdT). The grid layout and series of instructions to build the polymer "ATCG" are shown. In addition to the generality of the sequence that can be built, this is parallelizable across the EWOD chip, allowing for simultaneous growth of different sequences in as many addresses would be available per chip size.

An example of the steps necessary, for the sequence of EWOD-based loading, moving and incubating of fluid droplets to synthesize the nucleic acid sequence "A-T-C-G" on a solid support (e.g., magnetic bead) using EWOD technology on a device represented in FIG. 2 is set forth in Table 1, below.

For the sequence of movement described in Table 1, the chip represented in FIG. 2 is configured as follows: "A" contains buffer, salt (e.g., NaCl), dATP, and TdT; "T" contains buffer, salt (e.g., NaCl), dTTP, and TdT; "C" contains buffer, salt (e.g., NaCl), dCTP, and TdT; "G" contains buffer, salt (e.g., NaCl), dGTP, and TdT; "Buffer 1" contains a wash buffer; "Buffer 2" contains a second wash buffer; "Release" contains a buffer and/or components to release the polymer from the support. There is also a collection port to retrieve the polymers, and a waste port. Typically, the system is at 37° C. Many of the steps can be parallelized for efficiency, as allowed by EWOD technology.

TABLE 1

Exemplary system and sequence for movement of droplets on a microfluidic platform rendered as a grid according to FIG. 2.

| Sequence | FROM | TO |
| --- | --- | --- |
| 1 | Load "A" to A1 | |
| 2 | A1 | A3 |
| 3 | Load "T" to E1 | |
| 4 | A3 | B3 |
| 5 | B3 | C3 |
| 6 | C3 | B3 (mixing) |
| 7 | Incubate 1 minute (Add A) | |
| 8 | Buffer load to A1 | |
| 9 | Buffer load to A3 | |
| 10 | E1 | C1 |
| 11 | B3 | B7 |
| 12 | B7 | Waste |
| 13 | A3 | B3 |
| 14 | A1 | A3 |
| 15 | C1 | A1 |
| 16 | B3 | B7 |
| 17 | B7 | Waste |
| 18 | A3 | B3 |
| 19 | Load "C" to C1 | |
| 20 | A1 | A3 |
| 21 | B3 | B7 |
| 22 | B7 | Waste |
| 23 | A3 | B3 |
| 24 | Incubate 1 minute (Add T) | |
| 25 | Buffer load to A1 | |
| 26 | Buffer load to A3 | |
| 27 | B3 | B7 |
| 28 | B7 | Waste |
| 29 | A3 | B3 |
| 30 | A1 | A3 |
| 31 | C1 | A1 |
| 32 | B3 | B7 |
| 33 | B7 | Waste |
| 34 | A3 | B3 |
| 35 | A1 | A3 |
| 36 | B3 | B7 |
| 37 | B7 | Waste |
| 38 | A3 | B3 |
| 39 | Incubate 1 minute (Add C) | |
| 40 | Load "G" to G1 | |
| 41 | Buffer load to A1 | |

TABLE 1-continued

Exemplary system and sequence for movement of droplets on a microfluidic platform rendered as a grid according to FIG. 2.

| Sequence | FROM | TO |
| --- | --- | --- |
| 42 | Buffer load to A3 | |
| 43 | B3 | B7 |
| 44 | B7 | Waste |
| 45 | A3 | B3 |
| 46 | A1 | A3 |
| 47 | G1 | A1 |
| 48 | B3 | B7 |
| 49 | B7 | Waste |
| 50 | A3 | B3 |
| 51 | B3 | B7 |
| 52 | A1 | A3 |
| 53 | B7 | Waste |
| 54 | A3 | B3 |
| 55 | Incubate 1 minute (Add G) | |
| 56 | Release buffer load to A5 | |
| 57 | A5 | A3 |
| 58 | A3 | B3 |
| 59 | Incubate 1 minute | |
| 60 | B3 | B6 |
| 61 | B6 | Collect port |

In some forms the sequence of 61 steps of loading and moving droplets in and out of a fixed, growing polymer set forth in Table 1 is input as a computer-readable program.

d. Encoding of Digital Information

In an exemplary form, methods for microfluidic device-based template-free synthesis of DNA include encoding of digital information as the switch between a base type to another base type. For example, a series of 5 As ("AAAAA"), where 5 is representative of any number 1, 2, 3, or more than 3 and A is representative of any base, would be representative of a 0, and a subsequent series of 6 Ts ("TTTTTT"), where 6 is representative of any number 1, 2, 3, or more than 3 and T is representative of any other base, would be representative of a 1. Thus, in this specific instance, "AAAAATTTTTT" (SEQ ID NO: 25) would be representative of the digital equivalent of "01".

4. Manipulation of Biopolymers

In some forms, the methods add, remove, or modify a subset of component building blocks within an existing biopolymer. For example, in some forms, the methods attach additional component building blocks onto a biopolymer. In other forms, the methods remove one or more of the components of the biopolymer, for example, by degrading one or more component building blocks. In other forms, the methods modify an existing sequence within a biopolymer, for example, by modification of one or more chemical moieties of an existing residue, or by substitution of one component building block for another. In some forms, a biopolymer is manipulated by a combination of the addition of one or more components of a biopolymer and removal of one or more components of a biopolymer.

Manipulation of biopolymers is carried out according to the described methods for microfluidic-based movement of droplets including a droplet containing the biopolymer that is to be manipulated. In some forms the biopolymer is immobilized on the microfluidic system. In other forms, the biopolymer is present in solution, for example, present in one or more fluid reservoirs on a microfluidic device (e.g., an EWOD chip). In some forms the biopolymer is manipulated by substitution, removal, or addition of one or more sequences corresponding to a molecular or sequence barcode.

a. Molecular Barcoding

Molecular or sequence barcoding is a method of identifying molecules from within a pool of other molecules. Barcoding is used, for example, for sequencing identification in next generation sequencing with complex pools of DNA strands. Barcoding can also be implemented for cell-based identification and RNA identification in solutions where parsing the sequences and samples are important for downstream separation of the samples. The synthesis of the DNA for barcoding is typically achieved by pre-synthesis of the sequence using methods known in the art, and then ligated to the sample of interest by DNA ligase.

i. Adding Barcodes to Biopolymers

In some instances, the synthesized sequence-controlled polymer is a barcode for the recognition of the bead or the material within the bead. In some instances the barcode sequence is representative of information that is kept in silico for the access of the information. In some instances the DNA sequence is algorithmically generated and not kept on an external computer. In an exemplary method, a set of pre-designed orthogonal barcodes are used as a basis set for point mutations that either (i) maintain orthogonality similar to the original barcode set or (2) vary from one orthogonal barcode to another orthogonal barcode in a single, double, or greater than double mutations. In the exemplary method, a neighborhood of 10 barcodes are generated surrounding the original barcode. In each nearest neighbor of the barcode, a single point mutation or many point mutations are introduced such that the melting temperature between the mutated barcode and the capture reverse complement are varied by a pre-specified amount (e.g., 5 degrees). Thus, in each stepwise addition of more mutations, the temperature of capture lowers by, for example 5 degrees (or 1 degree or 20 degrees, or more than 20 degrees). Thus, the sequence of the barcode is changed and capture can be controlled by varying the sequence of the barcode or the capture strand.

In some forms, the molecular barcode that is varied in a neighborhood of sequences is representative of a description of underlying data, such as the amount of red that exists in a picture that is encoded by the DNA sequences that are encapsulated. For example, in some experiments, a picture of a red Ferrari is converted to DNA sequences through methods known in the art. The DNA strands are then encapsulated in silica, and the bead is barcoded to represent that the picture contains a red car. However, other images contain only partially red objects, such as a picture of a pink dress, that is only sometimes referred to as red, and thus would have a barcode of the red neighborhood, but would contain several point mutations compared to true red. In other cases, the picture may contain no red, such as a picture of a blue sky. In such cases, the bead may not have a red barcode, or may have a barcode with enough mutations to render it "not red." That picture may also then contain a "100% Blue" barcode. Exemplary values that can be identified using a corresponding nucleic acid barcode are presented in Table 2, below. Sequences in Table 2 represent twenty sequences that form a "neighborhood" of point mutations around the nucleic acid sequence CGGCC-CATCTGGTGTGATGCATTAC (SEQ ID NO: 1). In some forms, the sequences of SEQ ID Nos. 2-21 in Table 2 represent an exemplary barcode "hash" for SEQ ID NO: 1.

TABLE 2

Exemplary Sequence Barcodes and corresponding values

| Barcode Number | Metadata associated value | Nucleotide Barcode | Seq ID No. |
|---|---|---|---|
| 1 | 100% Red | CGGCCCATCTGGTGTGATGCATTAC | Seq ID No. 1 |
| 2 | 90% Red | CGGCCCATCTGGTGTGATGCAGTAC | Seq ID No. 2 |
| 3 | 80% Red | CGGCCCAACTGGTGTGATGCAGTAC | Seq ID No. 3 |
| 4 | 70% Red | CGGCCCAACTGGTGTCATGCAGTAC | Seq ID No. 4 |
| 5 | 60% Red | CGGTCCAACTGGTGTCATGCAGTAC | Seq ID No. 5 |
| 6 | 50% Red | CGGTCCAACTGGTGTCAGGCAGTAC | Seq ID No. 6 |
| 7 | 40% Red | CGGTCAAACTGGTGTCAGGCAGTAC | Seq ID No. 7 |
| 8 | 30% Red | CAGTCAAACTGGTGTCAGGCAGTAC | Seq ID No. 8 |
| 9 | 20% Red | CAGTCAAACTGGTCTCAGGCAGTAC | Seq ID No. 9 |
| 10 | 10% Red | CAGTCAAACAGGTCTCAGGCAGTAC | Seq ID No. 10 |
| 11 | 0% Red | CAGTCAAACAGTTCTCAGGCAGTAC | Seq ID No. 11 |
| 12 | 100% Blue | GGCCAGATTATATGAGCGTCTCCTT | Seq ID No. 12 |
| 13 | 90% Blue | GGCCAGATTATATGAACGTCTCCTT | Seq ID No. 13 |
| 14 | 80% Blue | GGCCACATTATATGAACGTCTCCTT | Seq ID No. 14 |
| 15 | 70% Blue | GGCCACATTAGATGAACGTCTCCTT | Seq ID No. 15 |
| 16 | 60% Blue | GGCCACATTAGATGAACCTCTCCTT | Seq ID No. 16 |
| 17 | 50% Blue | GGCAACATTAGATGAACCTCTCCTT | Seq ID No. 17 |
| 18 | 40% Blue | GGCAACATTAGATGAACCTGTCCTT | Seq ID No. 18 |
| 19 | 30% Blue | GGCAACATGAGATGAACCTGTCCTT | Seq ID No. 19 |
| 20 | 20% Blue | GTCAACATGAGATGAACCTGTCCTT | Seq ID No. 20 |
| 21 | 10% Blue | GTCAACATGAGATCAACCTGTCCTT | Seq ID No. 21 | ii. Removing Barcodes of Biopolymers

In some forms, the barcodes are removed from a biopolymer. For example, if a biopolymer or bead includes a barcode, the sequence that includes one or more components of the barcode can be removed from the biopolymer or bead. In some forms the methods subsequently re-synthesize a new barcode on the same biopolymer or bead. In some forms, the methods include a sequence of steps for rebarcoding of a biopolymer or bead. Therefore, automated microfluidic-based methods for re-barcoding a biopolymer or bead are provided. In such cases, one or more barcodes are removed from the biopolymer or bead.

Exemplary steps for removal of one or more component building blocks from a biopolymer include enzymatic cleavage or degradation, preferably at one or more sequence-specific sites within the biopolymer. In an exemplary form, one or more nucleotides are removed from a biopolymer by the activity of a nuclease enzyme, such as an exonuclease, or restriction enzymes, or RNases that degrade the material of the barcode. In some forms, one or more amino acids are removed from a polypeptide sequence by a protease enzyme. In some forms, one or more component building blocks are removed from a biopolymer using chemistries that destabilize the molecule, such as a high pH (>10), for example, to remove RNA tags. In some forms the methods include one or more steps to wash away the degrading or cleaving enzyme, or to remove the chemically-destructive factor from the biopolymer. In some forms the methods include one or more steps to synthesize a new barcode onto the biopolymer.

In some forms, the methods further include removing or neutralizing the inhibitor in order to facilitate further nucleotide incorporation. Finally, nucleotides that are incorporated into a biopolymer can be detectably labeled to monitor incorporation.

b. Encapsulation

In some forms, the methods encapsulate biopolymers. For example, in some forms, the methods include an additional step of encapsulating or otherwise covering a biopolymer in one or more outer layers. The outer layers can be any material that is useful for the encapsulation of a biopolymer. Exemplary encapsulation materials include gels, silicates, lipids, proteins, oils, polymers and combinations of these. Reversible encapsulation of nucleic acids in silica is describe in Paunescu, et al., *Nature Protocols*, volume 8, pages 2440-2448 (2013).

Synthesis of a biopolymer including the step encapsulation can enhance the stability of the biopolymer. In an exemplary form, a biopolymer is a nucleic acid sequence encoding one or more pieces of discrete data, for example, bit-stream data. Encapsulation of data-sequences protects the data-sequence from interrogation by other DNA sequences, in addition to adding thermal and chemical protection to the DNA.

In some forms, the encapsulated biopolymers are manipulated following encapsulation. For example, in some forms the protected DNA are barcoded using molecular recognition sequences such as biochemical tags and optical signatures. These identifying barcodes can be used to segregate the encapsulated data for retrieval and subsequent readout and conversion back to digital information.

Encapsulation or re-encapsulation of biopolymers can be carried out using methods and materials known in the art. In some methods the well or solution or synthetic cell-like compartment contains silica and all precursors for optical barcoding with quantum dots, or calcium alginate, or polyacrylamide, or PEG or PEI, or other polymers typically used in the formation of mineralized or hydrogel encapsulation. The catalyst for encapsulation will then be additionally added for the formation of nano- to micro-scale mineralized or hydrogel beads that encapsulate the internal contents of the synthetic cell compartment or the well, or the droplet in oil as implemented in the microfluidic device.

Typically, biopolymers having a sequence of any desired length are packaged, encapsulated, enveloped, or encased in gel-based beads, protein viral packages, micelles, mineralized structures, siliconized structures, or polymer packaging, herein referred to as "sequence-controlled polymer objects". In some forms, the synthesized biopolymers consist of a single, continuous polymer, contained within an encapsulation particle having nanometer dimensions. In some forms, the biopolymers consist of many such polymers that are combined to be contained together within a single encapsulation particle. These discrete biopolymer "packages" allow incorporation of one or more specific molecular "tags" (such as barcodes) on the surface of the structures. Some exemplary tags include nucleic acid sequence tags, protein tags, carbohydrate tags, and any affinity tags.

In some forms, the encapsulated particle will be barcoded or tagged by a molecular identifier such as an RNA, DNA, Locked nucleic acid, peptide nucleic acid, or peptide or protein or sugar or other recognition polymer that can be used to identify the particle by molecular interrogation. In some instances, this identifier may be an antibody. In other instances, this identifier may be a sequence specific polymer such as a sequence of DNA. In some implementations this may be synthesized using the techniques described above by using a template free polymerase and sequence-controlled additions for the active synthesis of the nucleic acid barcode. In some implementations, this may be synthesized by addition of a pre-synthesized primer using a ligase, or a template free polymerase, or through chemical addition of the pre-synthesized primer to the particle through methods known in the art. In some cases the barcode can be sequence-controlled but specifically generated for molecular recognition such as for a RNA aptamer or fluorescent RNA aptamer such as the Spinach aptamer, or by other RNA aptamers that can be identified by interactions with other proteins or RNAs.

When an encapsulating agent is used to completely encase a one or more biopolymers, the one or more biopolymer sequences can be present either within the particle core, or associated with one or more encapsulating layers surrounding the core, for example, embedded within an encapsulating material. Any indices/affinity/barcode tags are typically exposed and accessible at the surface of the particle. For example, in some forms, the indices/affinity tags are added in such a manner as to be embedded within or otherwise attached to the external surface of the particles.

In some forms, a molecular tag or barcode may need to be removed or altered dynamically in an automated and pre-defined way, or in an active way with feedback from a user or computer for dynamic memory allocation and re-allocation. In some implementations, the barcode can be digested by a DNase, exonuclease, or restriction enzyme. In some instances where the barcode is RNA, RNase A or RNase T1, or other RNases can be used for barcode removal, or can be removed by the presence of high pH. In some instances, where the barcode is a peptide or protein or antibody or protein tag such as a polyhistidine tag, the barcode can be removed by peptidase or proteinase enzymes, or through pH. In another implementation targeted photo/UV-degradation may be used. In each case, the encapsulated product may be optionally purified from the removal solution and residual debris for later use.

Nanometer to micrometer-scale beads synthesized from polymers or compounds such as, for example, silicon dioxide, can be synthesized by flow chemistry and microfluidics approaches. Silica precursors and optical barcodes, such as dyes, quantum dots, lanthanides, and/or color centers are mixed with solvent and catalyst, and agitated until silica particles form. In another implementation, a reservoir containing silane precursors with dyes and/or quantum dots, lanthanide emitters, or color centers is mixed with DNA memory with other chemical precursors, such as catalyst and solvent, through flow injection through a fluid junction in a flow chemistry set-up. The mixed precursors are passed through a heater to allow for silica formation.

In some forms, silica cores are synthesized with DNA memory and optical barcodes by mixing the silica precursors, optical barcodes, and DNA memory with surfactant to form water-in-oil droplets. Resulting droplets are incubated at 65° C. until silica forms. Precise size control of particles can be achieved by controlling the size of the water-in-oil emulsion.

In other forms, silica precursors, DNA memory, and optical barcodes are mixed using an automated liquid-handling device wherein specific volumes are dispensed into specific wells in 96-, 384-, 1536-well plates. After the precursors are added into the well-plates, the well-plates are mixed with agitation to produce silica particles.

In another form, silica precursors, DNA memory, and optical barcodes are mixed using droplets on a microfluidic device, for example, using EWOD-actuated movement of droplets.

In some forms, sequence-controlled polymers synthesized either using the approach defined here, or using another approach are grouped together on the EWOD or other microfluidics device. In some forms, sequence-controlled polymers are grouped together by mixing synthesized or added strands, or are kept separate. In a typical workflow, the strands that are mixed are associated either for their sequences or for the purpose of encoding similar data or part of the same bitstream sequence.

In some instances, the mixed strands will be encapsulated. Encapsulation of biopolymers for use in nucleic acid memory systems is described in International publication No. WO 2017/189914. In some forms, silica nanoparticles can be pre-manufactured, or manufactured on the microfluidics device. Biopolymers, such as DNA, can be added into the silica by ion-pairing of the phosphate backbone with the ammonium-functionalized surface of silica particles. Therefore, in some forms, the methods include the step of encapsulating biopolymers within silica. In some forms, the methods produce ammonium functionalized particles by preparing a silica core containing one or more agents, such as dyes, quantum dots, lanthanide emitters, or color centers, at specific concentrations for optical barcoding. In some forms, the optically-barcoded silica core is functionalized, for example, by addition of 3-(trimethoxysilyl)propyl-trimethylammonium chloride. The methods adsorb biopolymers into the silica core by combining the biopolymer with the silica core. The methods optionally add a further layer of silica (e.g., a silica "shell" is added), for encapsulation using tetraethoxysilane.

Silica cores can be prepared in large-scale through flow chemistry and microfluidics approaches. Therefore, in some forms, a reservoir containing silane precursors with dyes and/or quantum dots, lanthanide emitters, or color centers is mixed with biopolymers (e.g., bitstream-encoded nucleic acids), and with other chemical precursors, such as catalyst and solvent, through flow injection through a fluid junction in a continuous-flow microfluidic system.

In some forms, fluid including combined precursors is passed through a heater to allow for silica formation. The methods purify silica cores, which are then and passed through another tube for DNA barcoding of the silica.

In some forms, silica cores are synthesized with biopolymers (e.g., bitstream-encoded DNA) and optical barcodes, for example, by combining the silica precursors, optical barcodes, and DNA memory with surfactant to form water-in-oil droplets. The methods the step of incubating the resulting droplets at a suitable temperature (e.g., 65° C.), for sufficient time to allow the silica to form.

In some forms, silica precursors, DNA memory, and optical barcodes are mixed using droplets on an electrowetting device.

In some instances, the solid support is on a bead that is itself composed all or in part of sequence controlled polymers such as DNA. In one such example, the solid support is a bead that contains DNA sequences that are either generated by the system in previous runs, or externally generated using methods known in the art. In some cases, the addition of nucleotides to the solid support bead is using all of the methods described here. In other cases, the bead is a solid support and the additional nucleotides are added by incubation with ligases, or other template-free polymerases or chemically synthesized using standard and known chemistries to generate the nucleic acid or other sequence in place.

DNA barcodes are attached to the surface through covalent approaches, for example (but not limited to) amide bond linkage using N-hydroxysuccinimidyl esters, Michael addition through by sulfur groups, azide-alkyne cycloaddition, strain-release cycloaddition, or other covalent attachment chemistries that are known in the art. In one example, silica containing DNA memory is coated with amine functional groups using 3-aminopropytriethoxysilane, 3-aminopropyltrimethoxysilane, or other chemical derivatives that introduce amine functional groups that are known in the art. Treatment with glutaric anhydride, succinic anhydride, or other ring anhydrides known in the art to the amino-functionalized silica introduces carboxylic acid functional group Amino-modified DNA is then attached using 1-ethyl-3-(3-dimethylaminopropyl)carbodiimide (EDC) and N-hydroxysuccinimide (NHS), dicyclohexylcarbodiimide, 1-hydroxybenzotriazole (HOBt), hydroxy-3,4-dihydro-4-oxo-1, 2,3-benzotriazine (HOOBt), 1-hydroxy-7-aza-benzotriazole (HOAt), ethyl 2-cyano-2-(hydroxyimino)acetate, 4-N,N-dimethylamino pyridine (DMAP), or other activating reagents that are known in the art. In another example, bifunctional crosslinker succinimidyl 4-(N-maleimidomethyl)cyclohexane-1-carboxylate (SMCC) is added to the amino-functionalized silica to introduce a maleimide functional group. DNA barcodes are then introduced via Michael addition using sulfhydryl groups on DNA. In another example, amino-functionalized silica is treated with 1-akyne NHS ester or dibenzocyclooctyne (DBC) NHS ester to introduce alkynyl groups on the surface of the silica. Azide-containing DNA is attached using Cu-catalyzed cycloaddition or strain-release cycloaddition. Any "click"-type functional groups known in the art can be used to attach DNA barcodes on silica.

In some forms, the encapsulated product can be barcoded again with the same or different barcode sequence. This addition of a new barcode is synthesized by methods listed above. This new synthesis allows for rebarcoding the system, or a single object, or two objects, or more than two objects.

Each case of the barcoding, barcode removal, and re-barcoding, can be accomplished on a microfluidic device where the solution is moving across the bead or encapsulated product, or surface to allow for washing or monomeric additions to the product.

In some implementations the barcodes used as identifiers to the particles are orthogonal to other particles containing the same or different sets of sequences. In some cases, the barcodes are designed to have minimal cross-talk between them and other barcodes and other barcode complementary sequences.

In some instances, the barcodes are error prone and may vary by 1, 2, 3, 4, or more than 4 nucleotides from the user specified barcode. In some instances, the barcodes may be specified to have 1, 2, 3, 4, or more than 4 mutations from the initial barcode. In some implementations, the barcodes are equated with meanings, such as representative of the color red, or blue, or the year, or a geographic location. In some instances, the specified point mutations are representative of the measure of barcode representation, such as a measuring the representation of red from 1 to 10 as how exact the barcode sequence is to the original system-or-thogonal sequence. In some instances, the barcode representing the color red and the barcode representing blue can be mutated by 1, 2, 3, 4, or more than 4 point mutations to allow the red barcode to be more similar to the blue barcode. Thus the underlying polymer may be described as a variation of the red to blue spectrum based on the amount of mutations from the pure red or pure blue associated barcodes.

In some implementations, the representative barcodes can be algorithmically generated or can be associated by an external table or database.

In some implementations, the representative barcodes can be extracted or pulled down based on the correctness compared to the original barcode. Thus a barcode sequence more similar to red would get pulled down with a red complementary sequence and a "blue-er" barcode could be pulled down with a blue complementary sequence.

The algorithmic control of the orthogonality of the barcodes is generally applicable to barcoding any molecule used for sequencing, polymerase chain reaction, single-cell sequencing, or any application where fuzzy searches over molecular data are applicable.

In some forms, the complementary sequences to the barcodes are labeled with a fluorescent moiety such as Cy5, Cy3, ROX, Atto, or other fluorescent molecules on the 5', 3' or internally. In these cases, the complementary sequence to the barcode of interest will interact by Watson-Crick base pairing. Using methods described above by the EWOD device, or by other microfluidics devices and channels, the pool of barcoded particles can be washed and the particles can be sorted by FACS, or microscope imaging, or other imaging platforms that would subsequently allow for sorting. In one form, the fluorescent read from a camera could be used to track a certain tagged particle, that could then be segregated from the population by an optically controlled EWOD device, or by separation by FACS based sorting of the particles. In all cases, barcodes may be dynamically altered on-the-fly to relabel or alter barcodes based on external requirements, using the preceding strategies.

D. Purification of Biopolymers

The methods include purification of the assembled biopolymers. Purification separates assembled biopolymers/encapsulated biopolymers from the substrates and buffers required during the assembly process. Typically, purification is carried out according to the physical characteristics of biopolymers. For example, the use of filters and/or chromatographic processes (FPLC, etc.) is carried out according to the size and structural properties of the biopolymers.

1. Isolating Biopolymers from the Microfluidic Device

In some forms, biopolymers are purified from the synthesis device using affinity chromatography, or by filtration, such as by centrifugal filtration, or gravity filtration. In some forms, filtration is carried out using an Amicon Ultra-0.5 mL centrifugal filter (MWCO 100 kDa).

In some forms, isolating and/or purifying biopolymers includes separation of the newly-synthesized biopolymer from a solid support matrix. When a solid support matrix is employed to anchor or otherwise control the initiator sequence throughout synthesis, the biopolymer is cleaved or otherwise separated from the solid support following completion of synthesis. Removing the biopolymer from a solid support can be carried out according to methods generally known in the art. For example, in some forms, the biopolymer is designed to include one or more cleavage enzyme recognition sequences for cleavage of the biopolymer following synthesis. Biopolymers can be removed from a solid support during or after synthesis, or after purification, or after one or more steps for post-purification modification of the biopolymer.

When an enzyme is used to cleave a biopolymer from a solid support matrix, the biopolymer can be designed to include a specific cleavage enzyme recognition sequence at or near the desired cut-site. In an exemplary form, the cleavage recognition sequence is within or near to the initiator sequence. For example, in some forms the biopolymer is a nucleic acid, and the cleavage enzyme is an enzyme that specifically cuts nucleic acid upon recognition of a nucleic acid sequence. Exemplary enzymes for use in the methods include restriction endonuclease (RE) enzymes, such as blunt cutting RE and overhang-producing RE.

Following purification, biopolymers can be placed into an appropriate buffer for storage, and/or subsequent structural analysis and validation. Storage can be carried out at room temperature (i.e., 25° C.), 4° C., or below 4° C., for example, at −20° C. Suitable storage buffers include PBS, TAE-$Mg^{2+}$ or DMEM.

2. Validation of Synthesized Biopolymers

In some forms, the methods include steps for the validation of the synthesized biopolymers.

a. Sequence Determination

Methods for validating biopolymers include sequencing of biopolymers. Sequencing can be carried out before, or following one or more purification steps. Compositions and methods for sequencing of biopolymers are known in the art. In some forms, biopolymers are engineered either during or after synthesis to include one or more reagents or functional molecules to facilitate sequencing. For example, blunt ends produced by blunt-cutting RE are compatible with universal sequence adapters. In some forms, sequencing adapters for use in the described methods are universal adapters that bind to DNA fragments produced by any blunt-cutting restriction endonuclease enzyme. Universal adapters are compatible with the blunt ended DNA fragments created by all blunt-cutting RE enzymes. In some forms, the adapters are compatible with any double stranded DNA fragment having a single base overhang. For example, universal adapters can have a single-base overhang that is complementary to a single base overhang that is common to a pool of double stranded DNA fragments. In some forms, the universal adapters are compatible with all DNA fragments having a single adenine. Preferred universal sequencing adapters are "Y-shaped" adapters (Y-adaptors). Y adapters allow different sequences to be annealed to the 5' and 3' ends of each nucleic acid in a library (Shin, et al., *Nature Neuroscience* 17, 1463-1475 (2014)).

In some forms, the sequencing adapters are ILLUMINA® Y-adaptors, paired with the dA tailing step, prevent concatamer formation, increase the sequenceable fraction of the library, and allows for paired-end sequencing. Use of ILLUMINA® Y-adaptors also enables incorporation of dual-indexed barcodes during library amplification, which facilitates large-scale, inexpensive multiplexing. In some forms, the adapters enable selective PCR enrichment of adapter-ligated DNA fragments. Preferably, sequence adapters can bind to a flow cell. Therefore, the sequence adapters enable the associated DNA fragments to be manipulated through multiple applications for next generation sequencing.

In some forms, the methods include the step of nucleic acid sequence determination. The biopolymers can be sequenced according to sequencing methods known in the art, for example, using techniques described in U.S. Patent Publication No. 2007/0117102, and U.S. Patent Publication No. 2003/013880. In general, methods for nucleic acid sequence determination include exposing the target nucleic acid to a primer that is complementary to at least a portion of the target nucleic acid, under conditions suitable for hybridizing the primer to the target nucleic acid, forming a template/primer duplex.

b. Detection of Labels

In some forms, the methods include the step of detecting one or more labels or detectable moieties incorporated into the biopolymer. For example, any suitable/appropriate detection method may be used to identify an incorporated label (e.g., a labelled nucleotide analog), including radioactive detection, optical absorbance detection, e.g., UV-visible absorbance detection, optical emission detection, e.g., fluorescence or chemiluminescence. Single-molecule fluorescence can be carried out using a conventional microscope equipped with total internal reflection (TIR) objective. The detectable moiety can be detected on a substrate by scanning all or portions of each substrate simultaneously or serially, depending on the scanning method used. For fluorescence labeling, selected regions on a substrate may be serially scanned one-by-one or row-by-row using a fluorescence microscope apparatus (see U.S. Pat. Nos. 5,445,934; and 5,091,652). Devices capable of sensing fluorescence from a single molecule include scanning tunneling microscope (STM) and the atomic force microscope (AFM). Hybridization patterns may also be scanned using a CCD camera (e.g., Model TE/CCD512SF, Princeton Instruments, Trenton, N.J.) with suitable optics (Ploem, CCD (Chase-Completed-Device) in Fluorescent and Luminescent Probes for Biological Activity Mason, T. G. Ed., Academic Press, Landon, pp. 1-11 (1993), such as described in Yershov et al., Proc. Natl. Aca. Sci. 93:4913 (1996), or may be imaged by TV monitoring. For radioactive signals, a phosphorimager device can be used (Johnston et al., Electrophoresis, 13566, 1990; Drmanac et al., Electrophoresis, 13:566, 1992; 1993). Other commercial suppliers of imaging instruments include General Scanning Inc., (Watertown, Mass. on the World Wide Web at genscan.com), Genix Technologies (Waterloo, Ontario, Canada; on the World Wide Web at confocal.com), and Applied Precision Inc. Such detection methods are particularly useful to achieve simultaneous scanning of multiple attached target nucleic acids.

III. Systems for Synthesis of Biopolymers

A. Computer Implemented Systems

The systems and methods provided herein are generally useful for predicting the design parameters that produce a biopolymer having a user-defined sequence. In some forms, the parameters corresponding to the desired form and the desired sequence are input using a computer-based interface that allows for the sequence input process to be carried out in a completely in-silico manner. For example, in certain forms, the methods are implemented in computer software, or as part of a computer program that is accessed and operated using a host computer. In other forms, the methods are implemented on a computer server accessible over one or more computer networks.

FIG. 1 depicts the work flow of methods that can be implemented. In some forms, a user accesses a computer system that is in communication with a server computer system via a network, i.e., the Internet or in some cases a private network or a local intranet. One or both of the connections to the network may be wireless. In a preferred form the server is in communication with a multitude of clients over the network, preferably a heterogeneous multitude of clients including personal computers and other computer servers as well as hand-held devices such as smartphones or tablet computers. In some forms the server computer is in communication, i.e., is able to receive an input query from or direct output results to, one or more laboratory automation systems, i.e., one or more automated laboratory systems or automation robotics configured to automate synthesis of biopolymers according to the described methods.

The computer server where the methods are implemented may in principle be any computing system or architecture capable of performing the computations and storing the necessary data. The exact specifications of such a system will change with the growth and pace of technology, so the exemplary computer systems and components should not be seen as limiting. The systems will typically contain storage space, memory, one or more processors, and one or more input/output devices. It is to be appreciated that the term "processor" as used herein is intended to include any processing device, such as, for example, one that includes a CPU (central processing unit). The term "memory" as used herein is intended to include memory associated with a processor or CPU, such as, for example, RAM, ROM, etc. In addition, the term "input/output devices" or "I/O devices" as used herein is intended to include, for example, one or more input devices, e.g., keyboard, for making queries and/or inputting data to the processing unit, and/or one or more output devices, e.g., a display and/or printer, for presenting query results and/or other results associated with the processing unit. An I/O device might also be a connection to the network where queries are received from and results are directed to one or more client computers. It is also to be understood that the term "processor" may refer to more than one processing device. Other processing devices, either on a computer cluster or in a multi-processor computer server, may share the elements associated with the processing device. Accordingly, software components including instructions or code for performing the methodologies of the invention, as described herein, may be stored in one or more of the associated memory or storage devices (e.g., ROM, fixed or removable memory) and, when ready to be utilized, loaded in part or in whole into memory (e.g., into RAM) and executed by a CPU. The storage may be further utilized for storing program codes, databases of genomic sequences, etc. The storage can be any suitable form of computer storage including traditional hard-disk drives, solid-state drives, or ultrafast disk arrays. In some forms the storage includes network-attached storage that may be operatively connected to multiple similar computer servers that comprise a computing cluster.

1. Preparation of Libraries of Addressed Biopolymers

In some forms, biopolymer libraries are designed by automated methods. Automated design programs for generating uniquely addressed biopolymers allow for a diverse set of sequences to be made, towards the synthesis of a library of biopolymer for diverse applications. In an exemplary form, libraries of biopolymers with diverse sequences are useful for applications in memory storage, or applications for the analysis of a genome. For example, in some forms, a library or libraries of biopolymers can be constructed with the same or different labels, such as capture tags or target sequences complementary to one or more target molecules.

a. High-throughput Production of Biopolymers and Modifications

Systems for the automated synthesis of libraries of biopolymers including different modifications can be implemented using automated methods. Typically, computational systems are applied to automate sequence designs of a diverse set of uniquely addressed biopolymers, such as nucleic acids. Generally, the high-throughput library generation of user-defined biopolymers is achieved via multiple automated steps. Automated design programs for synthesizing from hundreds to thousands of biopolymer sequences, such as nucleic acid sequences, allows for a diverse set of molecules to be made, towards the synthesis of libraries of sequences for diverse applications.

In some forms, the sequences of biopolymers to be synthesized are input as a batch or set of sequences, for example, from a library or database. In other forms, the sequences of biopolymers are generated prior to or at the point of being input, for example, by a computational algorithm. An exemplary computational approach generates a set of biopolymers with specific sequences, sizes, structural or functional properties. For example, the number of biopolymer sequences generated in silico is about $10^5$, $2\times10^5$, $3\times10^5$, $4\times10^5$, $5\times10^5$, $6\times10^5$, $7\times10^5$, $8\times10^5$, $9\times10^5$, $10^6$, $10^7$, or more than $10^7$.

In preferred forms, high-throughput methods for generation of tens, hundreds or thousands of biopolymers employ automated liquid handlers. For example, high-throughput methods employ liquid dispensers for providing reagents as reservoirs to a surface for automated droplet splitting, movement and combining. The automation of the methods can include providing reagents as reservoirs to designated locations on a suitable microfluidic device surface, such as an EWOD chip. Generally, automation is preferred for synthesizing libraries of biopolymers. Using stocks of component building blocks, in combination with EWOD-mediated automated droplet movement, high-throughput combinatorial libraries of biopolymers are readily generated. In some forms, the volumes and concentrations of the reagent reservoirs are taken into consideration when deciding on the plate format.

In preferred forms, the automated methods simultaneously coordinate movement of droplets to synthesize more than ten biopolymers at a given time. The high-throughput methods allow fast generation of any number of biopolymers as desired for a library, for example, one thousand, two thousand, three thousand, four thousand, five thousand, six thousand, seven thousand, eight thousand, nine thousand, ten thousand, twenty thousand, thirty thousand, forty thousand, fifty thousand, one hundred thousand, one million, and more than one million user-defined sequence controlled biopolymers. In some forms, combinatorial libraries of biopolymers include variations in, size, sequence, and optionally modifications, allowing for one thousand, one million, or more than one million sequences in a library synthesized according to the automated methods.

In some forms, the methods employ custom-designed microfluidic device platforms, such as a chip including a custom-designed number of channels and wells. Techniques for the isolation, purification, or modification of biopolymers that are describe for single structures are applicable to high-throughput systems, typically via filtration and buffer exchange. In further forms, techniques such as rapid-run gel based assays, quantitative PCR (qPCR) and sequencing are used for amplification, structural analysis, and validation.

In some forms all of the parameters for a synthesis process are determined from the input sequences(s), for example, by a computer program. The program will provide a grid network, and assign sequences to corresponding addresses on the grid. For example, each unique sequence is assigned to a unique address on the computer-generated grid for fluid movement. In some forms, the program will also provide the sequences and other parameters for each initiator, corresponding catalysts, wash and block buffers. The amount, concentration and address of each reagent reservoir is determined, as well as the sequence of movement required to synthesize each biopolymer.

B. Graphical User Interface

In a preferred set of forms a computer server receives input submitted through a graphical user interface (GUI). The GUI may be presented on an attached monitor or display and may accept input through a touch screen, attached mouse or pointing device, or from an attached keyboard. In some forms the GUI will be communicated across a network using an accepted standard to be rendered on a monitor or display attached to a client computer and capable of accepting input from one or more input devices attached to the client computer. In other forms, a phone interface can identify, read and or run entered sequences.

In the exemplary form, the GUI contains a target sequence selection region where the user selects the parameters to be input. In this exemplary system a target sequence is indicated by clicking, touching, highlighting or selecting one of the sequence, or subsets of sequences, that are listed. In preferred forms, the target sequence is selected from a user-selected library. In some forms, the target sequence is selected and then customized to include user-defined features. Customization may include using any computer programs capable of such functions. Other parameters relating to the target sequence, such as length, molecular weight, overall size, charge, structure, etc.

In some forms, the GUI enables entering or uploading one or more sequences, such as libraries of nucleic acid sequences. For example, the GUI typically includes a text box for the user to input one or more sequences. The GUI may additionally or alternatively contain an interface for uploading a text file containing one or more query sequences.

In forms that include both options, the GUI may also contain radio buttons that allow the user to select if the target sequence will be entered in a text box or uploaded from a text file. The GUI may include a button for choosing the file, may allow a user to drag and drop the intended file, or other ways of having the file uploaded. Any of the parameters can be entered by hand to further customize The GUI also typically includes an interface for the user to initiate the methods based on the sequence(s) requested or other parameters. The exemplary GUI form includes a submit button or tab that when selected initiates a search according to the user entered or default criteria. The GUI can also include a reset button or tab when selected removes that user input and/or restores the default settings.

The GUI will in some forms have an example button that, when selected by the user, populates all of the input fields with default values. The option selected by the example values may in some forms coincide with an example described in detail in a tutorial, manual, or help section. The GUI will in some forms contain all or only some of the elements described above. The GUI may contain any graphical user input element or combination thereof including one or more menu bars, text boxes, buttons, hyperlinks, drop-down lists, list boxes, combo boxes, check boxes, radio buttons, cycle buttons, data grids, or tabs.

In some forms, the described systems and methods for the automated, programmed enzymic synthesis of biopolymers using a microfluidic device are controlled through one or more systems, databases or other resources that are implemented within Cloud computing. Cloud computing is an information technology paradigm that enables ubiquitous access to shared pools of configurable system resources and higher-level services that can be rapidly provisioned with minimal management effort, for example, over the Internet. For example, in some forms, the sequence of one or more biopolymers is selected from one or more databases accessed via cloud-based computing. In other forms, a general user interface interfaces with one or more databases implemented through cloud-based computing, for example, to design a synthesis or manipulation sequence for a given biopolymer. For example, in some forms, data is input at a cloud-based GUI specifying one or more biopolymer sequences, and the output includes one or more of a component initiation sequence, the locations and amounts of each component building block, enzyme catalyst, buffers, stop or blocking reagents (each as uniquely addressed positions on a microfluidic device, such as an EWOD chip), and a sequence of movements and other intermediary steps (incubations, temperature, light, etc.) required for synthesis. The sequence of movements for droplets or fluid flow parameters can be output in any suitable format, for example, computer-readable code. Output can include some or all of the information required for synthesis or manipulation of one or several biopolymers. In some forms, the output provides sequences of movement for simultaneous synthesis or manipulation of tens, hundreds, thousands or tens of thousands of biopolymers on one or more microfluidic systems. Exemplary information that can be provided as databases (e.g., cloud-based databases) include target biopolymer sequences, barcode sequences, component initiation sequences, and encoded bitstream data, for example, as implemented in nucleic-acid memory systems.

In some forms, cloud-based resources are accessed and implemented to direct manipulation of barcoded nucleic acids and/or memory objects. Therefore, in some forms, the methods employ cloud-based systems to design, synthesize and alter barcodes for use in the preparation and access of nucleic acid memory storage systems. In some forms, the methods construct and/or degrade one or more sequence barcodes present on a nucleic acid or memory object, according to one or more commands entered via a graphical user interface. For example, computer-based systems can be used to provide the sequences of movements and other parameters required to prepare databases of nucleic acid memory objects. Therefore, in some forms, systems and methods implement graphical user interfaces to access and organize the databases. In some forms, the user input requests access to one or more pieces of data stored within a database. The data request can be any format, for example, a request for one or more images, or one or more pieces of literature or data. The systems and methods can direct selection of one or more pieces of data, degradation of non-selected data, and/or reproduction of the selected data, according to the requirements of the user, for example, by providing the sequence of movements and other parameters necessary to actuate a microfluidic device loaded with the corresponding library of nucleic acid memory objects and other reagents.

IV. Compositions for Microfluidic Device-Mediated Biopolymer Synthesis

Biopolymers having a user-defined sequence, synthesized according to the described methods are provided. Methods for template-free synthesis of biopolymers require reagents including initiator sequences, component building blocks, assembly catalysts, assembly buffers, wash buffers, stop-buffers and block buffers, as well as reagents for manipulation and purification of the assembled biopolymer, including reagents for cleavage, sequencing and amplification of the biopolymer.

Compositions for synthesizing modified biopolymers are also described. The microfluidic device-based synthesis for assembling biopolymers according to the described methods can include one or more modified component building blocks, such as non-naturally occurring derivatives and analogs. In some forms, the biopolymers are synthesized to include one or more modified component building blocks. In other forms, the biopolymers are modified by the addition of functional moieties on the microfluidic device following synthesis. For example, in some forms, biopolymers are functionalized to include one or more molecules that are capable of binding or otherwise interacting with one or more target molecules. Compositions for the microfluidic device-based synthesis, manipulation, and purification or amplification of biopolymers are described in further detail below.

A. Microfluidic Devices for Biopolymer Synthesis

Microfluidic devices and systems for the distribution and movement of small volumes required for synthesis are provided. Platforms for actuating splitting, movement, and combining of sub-microliter volumes of fluid as independent droplets can be employed for the described methods. Exemplary systems and devices include acoustic droplet distribution such as the ECHO® 555 liquid handling device available commercially, volumetric displacement distribution such as the Mosquito pipette robot, or ink-jet type fluidic distributors. Additionally, the synthesis may occur by flow across a chip, with microwells or synthetic compartments used for synthesis.

In some forms, the microfluidic device uses acoustic droplet ejection (ADE) to actuate movement of fluids. In other forms, the microfluidic device uses electrowetting on dielectric (EWOD) to actuate fluid movement. In further forms, the microfluidic device utilizes photo-electrowetting to actuate movement. In some forms, the microfluidics device utilizes a combination of different mechanisms for fluid handling/controlled fluid movement. Typically, the microfluidic device will be integrated with a computer to enable the automated, programmed control of the device. Systems and software for computer-mediated control of microfluidic devices are known in the art (see, for example, ECHO® Software Applications, commercially available from Labcyte).

1. Electrowetting on Dielectric (EWOD) Devices

In some forms, growing biopolymer is immobilized at an addressed location on the EWOD chip. For example, in some forms, the component initiation sequence or the catalyst includes one or more sequences designed to hybridize or otherwise bind to stationary-phase objects such as magnetic beads, surfaces, agarose or other polymer beads. In other instances, the component initiation sequence or the catalyst includes one or more sites for conjugation to a molecule. For example, the component initiation sequence or the catalyst can be conjugated to a protein, or non-protein molecule, for example, to enable affinity-binding of the initiation sequence or the catalyst, or of the synthesized polymer. Electrowetting-on-dielectric (EWOD) actuation enables digital (or droplet) microfluidics where small packets of liquids are manipulated on a two-dimensional surface. An exemplary EWOD platform is a chip, such as a microfluidic chip. EWOD chip liquid droplet driving systems are described for use in methods for EWOD-based synthesis of biopolymers. The EWOD chips actuate movement of fluid droplets, for example, by electrifying one or more driving electrodes to direct movement of liquid droplets to target positions. Therefore, the EWOD chip has the capability of moving droplets from one addressed position to another by the application of electric potential at a neighboring location.

In some forms, the electrowetting device employs channels and wells for the controlled movement and combining of fluids from reservoirs along the channels in the chip.

In some forms, the electrowetting device is a chip using an all-electronic (i.e., no ancillary pumping) real-time feedback control of on-chip droplet generation. Therefore, digital microfluidic systems that operate without carrier flows and preferably without any micro-channels are described for use with the described methods. Typically, the movement of fluids is actuated by driving mechanisms acting on the droplets locally, i.e., on individual droplets. EWOD devices and methods of use thereof are known in the art, for example, as described in WO 2006/005880, WO 2013/102011, WO 2016/111251, US 2017/0326524 A1, U.S. Pat. No. 8,304,253 B2, U.S. Pat. No. 8,883,014 B2, U.S. Pat. No. 8,459,295 B2, U.S. Pat. No. 8,834,695 B2, U.S. Pat. No. 9,266,076 B2, U.S. Pat. No. 9,169,573 B2, U.S. Pat. No. 9,539,573 B1, U.S. Pat. No. 9,005,544 B2, U.S. Pat. No. 9,808,800 B2, and in Gong, et al., *Lab Chip.*; 8(6): 898-906 (2008). EWOD devices for DNA manipulation including polymerase chain reaction, ligation, cloning, generation of larger DNAs from smaller primers are described in Lin, et al., *Journal of Adhesion Science and Technology*, 26 (12-17): pp. 1789-1804; PMCID: PMC4770201 (2012); and Choi, et al., *Annu. Rev. Anal. Chem.* 5, pp. 413-40 (2012)). Systems for electrowetting on dielectric microfluidics using chips for high-throughput EWOD applications are described in the review article entitled Parallel processing of multi-functional, point-of-care bio-applications on electrowetting chips published by Fair in the annals of 14th International Conference on Miniaturized Systems for Chemistry and Life Sciences, pp. 2095-2097 (2010).

The systems and devices described by Fair utilize an electric field established in the dielectric layer to create an imbalance of interfacial tension if the electric field is applied to only one portion of the droplet, which forces the droplet to move. Droplets are usually sandwiched between two parallel plates with a filler medium, such as silicone oil. Requirements for high throughput, point-of-care microfluidic chips that can process raw physiological samples include: 1) low number of input/output (I/O) ports and on-chip reagent storage; 2) flexible chip architecture for efficient use of fluidic processing elements; 3) programmable electronic control; 4) parallel or multiplexed operation; 5) low cross-contamination to allow resource sharing; and 6) scalability.

B. Addressed Biopolymers

Template-free synthesis of biopolymers according to the described methods can simultaneously produce from one up to several tens of thousands of addressed biopolymers having user-defined sequences. Exemplary classes of biopolymers that can be synthesized using automated methods include nucleic acids (e.g., DNA, RNA) polypeptides (e.g., proteins, peptidomimetics), oligosaccharides (e.g., carbohydrates), lipids, block co-polymers, and combinations of these (glycol-peptides, lipo-peptides, glycolipids, etc.).

The methods synthesize Biopolymers in the absence of a template sequence. Rather, the desired sequence of the biopolymer is provided, for example, as computer-readable data, to coordinate the sequential movement of droplets to assemble the desired molecule. In some forms, the input sequence is user-defined. In other forms, the user can select the sequence and size of the biopolymer to be generated at random.

Input data for a polymer sequence is typically provided in a computer readable format that is converted to from a non-computer readable format. In some forms, input data is in the form of biopolymer sequence that is converted (e.g., by computer software) to control movement of droplets for microfluidic device-based synthesis of an encoded biopolymer sequence that is distinct to the input sequence. For example, in some forms, input data is in the form of a nucleic acid sequence that includes one or more sequences of genomic DNA or messenger RNA (mRNA), and the DNA or mRNA sequence is converted to control movement of droplets for microfluidic device-based synthesis of the polypeptide sequence corresponding to the translated genomic DNA or mRNA sequence. In other forms, input data is in the form of a polypeptide sequence that is converted to control movement of droplets to actuate synthesis of the corresponding nucleic acid coding sequence. In some forms, the input is in the form of bitstream data, which is converted to control movement of droplets to actuate synthesis of a corresponding biopolymer sequence encoding the bitstream data.

Schemes, techniques, and systems for encoding data in the form of a sequence, such as a biopolymer, are known in the art. The described methods can include the step of converting data into or encrypting data within the sequence of one or more biopolymers.

A non-limiting list of sequence-controlled biopolymers includes naturally occurring nucleic acids, non-naturally occurring nucleic acids, naturally occurring amino acids, non-naturally occurring amino acids, peptidomimetics, such as polypeptides formed from alpha peptides, beta peptides, delta peptides, gamma peptides and combinations, carbohydrates, block co-polymers, and combinations thereof. Sequence-defined unnatural polymers closely resemble biopolymers, such as polymers incorporating non-canonical amino acids. e.g., peptidomimetics, such as β-peptides (Gellman, S H. Acc. Chem. Res., 31, 173-180 (1998)), peptide nucleic acids (PNA), peptoids or poly-N-substituted glycines (Zuckermann, et al., J. Am. Chem. Soc., 1 14, 10646-10647(1992)), Oligocarbamates (Cho, C Y et al., Science, 261, 1303-1305(1993), glycomacromolecules, Nylon-type polyamides, and vinyl copolymers.

In some forms, the methods employ microfluidic device-mediated movement of droplets for synthesis of uniquely addressed sequences of nucleic acids. In some forms, the methods employ microfluidic device-mediated movement of droplets for synthesis of uniquely addressed sequences of polypeptides. In some forms, the methods employ microfluidic device-mediated movement of droplets for synthesis of uniquely addressed sequences of carbohydrates. In other forms, the methods employ microfluidic device-mediated movement of droplets for synthesis of uniquely addressed biopolymers that contain two or more classes of molecules, such as glycopeptides, glycolipids, lipopeptides, etc., or modified variants of nucleic acids, peptides or carbohydrates. An exemplary modified peptide is a peptidomimetic, such as an α-peptide peptidomimetic, a β-peptide peptidomimetic, a δ-peptide peptidomimetic, or a γ-peptide peptidomimetic, or combinations of these.

In some forms, the methods include providing a biopolymer sequence from a pool containing a multiplicity of similar or different sequences. In some forms, the pool is a database of known sequences.

1. Nucleic Acid Biopolymers

In a preferred form, the methods employ microfluidic device-mediated movement of droplets for synthesis of uniquely addressed nucleic acids. One or more of the parameters of the nucleic acid, including nucleotide sequence, size, melting temperature, charge, conformation, etc. are user-defined. Nucleic acids synthesized according to the described microfluidic device-based methods can be from 2 nucleotides in length, up to 100,000 nucleotides in length. In preferred forms, synthesized nucleic acids have a sequence of greater than 100 nucleotides in length, up to 1,000, 2,000, 3,000, 4,000, 5,000, or 10,000 nucleotides in length. In some forms, the microfluidic device-based methods synthesize one or more nucleic acids of more than 10,000 nucleotides in length. In some forms, the methods simultaneously synthesize multiple different nucleic acids, for example, between 1 and 10,000 uniquely addressed nucleic acids having the same or different sequences can be synthesized at any given time. In some forms, the methods simultaneously synthesize more than 10,000 uniquely addressed nucleic acids having the same or different sequences, for example, up to 20,000, 30,000, 40,000, 50,000, 60,000, 70,000, 80,000, 90,000, up to 100,000 nucleotides in length.

In certain forms information is contained within the nucleic acid sequence that is provided. Therefore, in some forms, discrete sets of data are rendered as sequences of nucleic acids, for example, in a pool or library of nucleic acids. In some forms, a pool of nucleic acid sequences ranging from about 100-1,000,000 bases in size is provided. In some forms, the nucleic acid sequences within a pool of multiple nucleic acid sequences share one or more common sequences. When nucleic acids that are provided are selected from a pool of sequences, the selection process can be carried out manually, for example, by selection based on user-preference, or automatically.

In some forms, the input nucleic acid sequence is not the same sequence as chromosomal DNA, or mRNA, or prokaryotic DNA. For example, in some forms, the sequence has less than 20% sequence identity to a naturally-occurring nucleic acid sequence, for example, less than 10% identity, or less than 5% identity, or less than 1% identity, up to 0.001% identity. Therefore, in some forms, the nucleic acid sequence provided as input is not the nucleic acid sequence of an entire gene, or a complete mRNA. For example, in some forms the input sequence is not the same sequence as the open-reading frame (ORF) of a gene. In some forms, the input sequence is not the same nucleic acid sequence as a plasmid, such as a cloning vector. Therefore, in some forms, the input sequence does not include one or more sequence motifs associated with the start of transcription of a gene, such as a promoter sequence, an operator sequence, a response element, an activator, etc. In some forms, the input sequence is not a nucleic acid sequence of a viral genome, such as a single-stranded RNA or single-stranded DNA virus. In other forms, the input sequence(s) are composed of the sequences of cDNAs, genes, protein sequences, protein coding open reading frames, or biological sequences that together in a pool form a database of biological sequences.

2. Encapsulated Biopolymers

The described methods for microfluidic-based assembly of can encapsulate biopolymers to produce discrete "objects" or "units" having a range of different structures. For example, in some forms, biopolymer objects include a core particle, onto which one or more sequence-encoded biopolymers is bound.

Binding of sequence encoded biopolymers to a particle core can be achieved using covalent or non-covalent linkages. In some forms, a core molecule is coated or coupled to a molecule which is an intermediary receptor, for example, a binding site that is recognized by one or more ligands associated with the sequence encoded biopolymer. Sequence-encoded biopolymers can be coupled or hybridized to the receptor-coated core molecule. In some forms, the polymer/core substructure is then coated with one or more encapsulating agents (i.e., "molecular shelling") to produce a coated biopolymer/core structure, which is then optionally coupled to one or more address labels. Binding of address labels to a coated biopolymer/core particle can be achieved using covalent or non-covalent linkages, or hybridization of complementary nucleic acids. DNA barcodes linked to genetic features greatly facilitate screening these features in pooled formats using microarray hybridization, and new tools are needed to design large sets of barcodes to allow construction of large barcoded mammalian libraries such as shRNA libraries. A framework for designing large sets of orthogonal barcode probes is described here. The utility of this framework was demonstrated by designing 240,000 barcode probes and testing their performance by hybridization. From the test hybridizations, new probe design rules were discovered that significantly reduce cross-hybridization after their introduction into the framework of the algorithm. These rules should improve the performance of DNA microarray probe designs for many applications.

3. Barcodes and Labels

In some forms, biopolymers synthesized according to the methods can include one or more components that act as a barcode or label. Barcodes and/or labels can be used to identify, isolate, sort, organize, degrade, maintain, store, purify or otherwise characterize or manipulate the biopolymer, or pool of biopolymers to which they are associated. Barcodes and labels can be selected from a wide variety of detectable, sortable or otherwise scorable molecules. Exemplary barcodes and labels include sequence identifiers, such as nucleotide or amino acid sequences; capture tags; and dyes or other detectable molecules. In some forms, one biopolymer includes one or more barcode or label. Barcodes or labels that can be used to capture the barcoded biopolymer for a pool of similar biopolymers are provided. Barcodes or labels that can be used to detect, quantify or otherwise assay the presence or absence of the biopolymer are provided. Barcodes or labels that enable the sorting or manipulation of the associated biopolymers are also provided. In some forms, the barcodes permit sorting, selecting, ordering, degradation, synthesis and manipulation of the associate biopolymers using microfluidic systems.

a. Sequence Identifiers

In some forms, the biopolymers include sequence identifiers (i.e., indexing or "barcoding" regions). Sequence identifiers can identify a biopolymer upon further processing. For example, in the case of combining biopolymers, the different sequences can be identified using different tags. Exemplary sequence identifiers include a nucleotide sequence of varying but defined length that is uniquely used for identification of one or more specific nucleic acids.

In certain forms, each biopolymer includes one or more unique sequences of component building blocks which enables identification of each biopolymer. In some forms, the biopolymers include two or more sequence identifiers, for identification using a dual-index system.

The length of the sequence identifier can be adjusted according to the needs of the user. For example, a length of 4 component building blocks is sufficient to produce up to 256 different sequences. Exemplary barcode sequences are nucleic acid sequences of between 4 and 10 nucleotides in length, inclusive. Preferably, the tag sequence identifiers differ by at least one nucleotide amongst all the different samples. An exemplary sequence identifier is 6 nucleotides in length.

An exemplary barcoded biopolymer is a nucleic acid encoding bitstream data including a nucleotide sequence that acts as a barcode to identify the encoded data. A DNA barcode is a short DNA sequence that uniquely identifies a certain linked feature, such as nucleic acid sequence encoding one or more genes, or pieces of metadata. Linking features to DNA barcodes of homogenous length and melting temperature (Tm) allows experiments to be performed on the features in a pooled format, with subsequent deconvolution by PCR followed by microarray hybridization or high throughput sequencing. DNA barcode technology greatly improves the throughput of genetic screens, making possible experiments that would otherwise be quite time-consuming or laborious. Numerous resources and software tools are currently available for designing DNA microarray barcodes/probes (see, for example, Nielsen et al. *Nucleic Acids Res* 31:3491-3496 (2003); Rouillard, et al., *Nucleic Acids Res* 31:3057-3062 (2003); Wang, et al., *Bioinformatics* 19:796-802 (2003); Hu, et al. BMC Bioinformatics 8:350 (2007); and Markham et al., *Methods Mol Biol* 453:3-31 (2008)).

DNA barcodes linked to genetic features greatly facilitate screening these features in pooled formats using microarray hybridization. Compositions of nucleic acid barcodes having distinct and detectable properties are known in the art. Xu et al describe the generation and characterization of 240,000 barcode probes, and test their performance by hybridization. Test hybridizations identified new probe design rules that significantly reduce cross-hybridization after their introduction into the framework of the algorithm. These rules should improve the performance of DNA microarray probe designs for many applications (Xu, et al., *Proc Nall Acad Sci*, 106 (7) 2289-2294 (2009)). Therefore, the described methods for microfluidic-based synthesis of biopolymers can produce barcoded nucleic acids including one or more barcodes that can be used to select a distinct biopolymer, or pool of biopolymers, based upon one or more of the sequence characteristics of the barcode. Exemplary characteristics that can be sued for the selection and isolation include thermal hybridization and melting temperature. The application of melting temperature to select and isolate a pool of biopolymers based upon melting and hybridization characteristics is represented in the Examples.

In some forms, sequence identifiers (i.e., barcodes) are included within initiator sequences. In other forms, the identifiers are attached to the initiator or to the growing biopolymer during the synthesis. In an exemplary form, a sequence identifier is attached to an initiator, or to a growing biopolymer as a single, pre-assembled unit.

Molecular or sequence barcoding is a method of identifying molecules from within a pool of other molecules. Barcoding is used for sequencing identification in next generation sequencing with complex pools of DNA strands. Barcoding can also be implemented for cell-based identification and RNA identification in solutions where parsing the sequences and samples are important for downstream separation of the samples. The synthesis of the DNA for barcoding is typically achieved by pre-synthesis of the sequence using methods known in the art, and then ligated to the sample of interest by DNA ligase.

Nanometer to micrometer-scale beads synthesized from polymers or compounds such as, for example, silicon dioxide, can be synthesized by flow chemistry and microfluidics approaches. Silica precursors and optical barcodes, such as dyes, quantum dots, lanthanides, and/or color centers are mixed with solvent and catalyst, and agitated until silica particles form. In another implementation, a reservoir containing silane precursors with dyes and/or quantum dots, lanthanide emitters, or color centers is mixed with DNA memory with other chemical precursors, such as catalyst and solvent, through flow injection through a fluid junction in a flow chemistry set-up. The mixed precursors are passed through a heater to allow for silica formation.

In another implementation, silica cores are synthesized with DNA memory and optical barcodes by mixing the silica precursors, optical barcodes, and DNA memory with surfactant to form water-in-oil droplets. Resulting droplets are incubated at 65° C. until silica forms. Precise size control of particles can be achieved by controlling the size of the water-in-oil emulsion.

In another implementation, silica precursors, DNA memory, and optical barcodes are mixed using an automated liquid-handling device wherein specific volumes are dispensed into specific wells in 96-, 384-, 1536-well plates. After the precursors are added into the well-plates, the well-plates are mixed with agitation to produce silica particles.

In another implementation, silica precursors, DNA memory, and optical barcodes are mixed using droplets on an electrowetting device. For example, nucleic acids can be modified to include proteins or RNAs having a known function, such as antibodies or RNA aptamers having an affinity to one or more target molecules. Therefore, the biopolymers designed and synthesized according to the described microfluidic device-based methods can be functionalized biopolymers.

Biopolymers synthesized according to the described microfluidic device-methods can include one or more functional molecules at one or more locations on or within the polymer. In some forms, the functional group is located at one or more termini. In other forms, the functional moiety is located within the biopolymer sequence at a distance from either terminus. In other forms, biopolymers include one or more functional moieties located within the sequence, and within one or both termini. When a biopolymer is modified to include two or more functional moieties, the functional moieties can be the same, or different.

Typically, biopolymers are modified by chemical or physical association with one or more functional molecules. Exemplary methods of conjugation include covalent or non-covalent linkages between the biopolymer and a functional molecule. In some forms, conjugation with functional molecules is through click-chemistry. In some forms, conjugation with functional molecules is through hybridization with one or more nucleic acid sequences present on the biopolymer.

b. Capture Tags

In some forms, the sequence of a biopolymer includes a capture tag. A capture tag is any compound that is used to separate compounds or complexes having the capture tag from those that do not. Preferably, a capture tag is a compound, such as a ligand or hapten, which binds to or interacts with another compound, such as ligand-binding molecule or an antibody. It is also preferred that such interaction between the capture tag and the capturing component be a specific interaction, such as between a hapten and an antibody or a ligand and a ligand-binding molecule.

A preferred capture tag is biotin. In some forms, biopolymers include one or more sequences of component building blocks that act as capture tags, or "Bait" sequences to specifically bind one or more targeted molecules. For example, in some forms, overhang sequences include nucleotide "bait" sequences that are complementary to any target nucleotide sequence, for example HIV-1 RNA viral genome.

Typically, targeting moieties exploit the surface-markers specific to a group of cells to be targeted. Exemplary targeting elements include proteins, peptides, nucleic acids, lipids, saccharides, or polysaccharides that bind to one or more targets associated with cell, or extracellular matrix, or specific type of tumor or infected cell. Targeting molecules can be selected based on the desired physical properties, such as the appropriate affinity and specificity for the target. Exemplary targeting molecules having high specificity and affinity include antibodies, or antigen-binding fragments thereof. Therefore, in some forms, biopolymers include one or more antibodies or antigen binding fragments specific to an epitope. The epitope can be a linear epitope. The epitope can be specific to one cell type or can be expressed by multiple different cell types. In other forms, the antibody or antigen binding fragment thereof can bind a conformational epitope that includes a 3-D surface feature, shape, or tertiary structure at the surface of a target cell.

Biopolymers and encapsulated biopolymer objects can include one or more functional sequences that can capture one or more functional moieties, including but not limited to single-guide- or crispr-RNAs (crRNA), anti-sense DNA, anti-sense RNA as well as DNA coding for proteins, mRNA, miRNA, piRNA and siRNA, DNA-interacting proteins such as CRISPR, TAL effector proteins, or zinc-finger proteins, lipids, and carbohydrates. In other forms, synthesized biopolymers are modified with naturally or non-naturally occurring nucleotides having a known biological function. Exemplary functional groups include targeting elements, immunomodulatory elements, chemical groups, biological macromolecules, and combinations thereof.

In some forms, functionalized synthesized biopolymers include one or more DNA sequences that are complementary to the loop region of an RNA, such as an mRNA. Synthesized nucleic acids functionalized with mRNAs encoding one or more proteins are described. In one exemplary case, a synthesized biopolymer can be functionalized with 1 or 2 or more nucleic acid sequences that are complementary to the loop region of an RNA, for example an mRNA, for example an mRNA expressing a protein.

In some forms, biopolymers include one or more targeting elements, for example, to enhance targeting of the synthesized biopolymers to one or more cells, tissues or to mediate specific binding to a protein, lipid, polysaccharide, nucleic acid, etc. For example, for use as biosensors, additional nucleotide sequences are included in the synthesized biopolymers.

Exemplary targeting elements include proteins, peptides, nucleic acids, lipids, saccharides, or polysaccharides that bind to one or more targets associated with an organ, tissue, cell, or extracellular matrix, or specific type of tumor or infected cell. The degree of specificity with which the synthesized biopolymers are targeted can be modulated through the selection of a targeting molecule with the appropriate affinity and specificity. For example, antibodies, or antigen-binding fragments thereof are very specific.

Typically, the targeting moieties exploit the surface-markers specific to a biologically functional class of cells, such as antigen presenting cells. Dendritic cells express a number of cell surface receptors that can mediate endocytosis. In some forms, synthesized biopolymers include nucleotide sequences that are complementary to nucleotide sequences of interest, for example HIV-1 RNA viral genome.

Additional functional groups can be introduced to synthesized biopolymers for example by incorporating biotinylated nucleotides into the synthesized biopolymers. Any streptavidin-coated targeting molecules are therefore introduced via biotin-streptavidin interaction. In other forms, non-naturally occurring nucleotides are included for desired functional groups for further modification. Exemplary functional groups include targeting elements, immunomodulatory elements, chemical groups, biological macromolecules, and combinations thereof.

Typically, the targeting moieties exploit the surface-markers specific to a group of cells to be targeted. Exemplary targeting elements include proteins, peptides, nucleic acids, lipids, saccharides, or polysaccharides that bind to one or more targets associated with cell, or extracellular matrix, or specific type of tumor or infected cell. The degree of specificity with which the synthesized biopolymers are targeted can be modulated through the selection of a targeting molecule with the appropriate affinity and specificity. For example, antibodies, or antigen-binding fragments thereof are very specific.

In some forms, biopolymers are modified to include one or more antibodies. Antibodies that function by binding directly to one or more epitopes, other ligands, or accessory molecules at the surface of cells can be coupled directly or indirectly to the biopolymers. In some forms, the antibody or antigen binding fragment thereof has affinity for a receptor at the surface of a specific cell type, such as a receptor expressed at the surface of macrophage cells, dendritic cells, or epithelial lining cells. In some forms the antibody binds one or more target receptors at the surface of a cell that enables, enhances or otherwise mediates cellular uptake of the antibody-bound biopolymers, or intracellular translocation of the antibody-bound biopolymer, or both.

Any specific antibody can be used to modify the nucleic acid biopolymers. For example, antibodies can include an antigen binding site that binds to an epitope on the target cell. Binding of an antibody to a "target" cell can enhance or induce uptake of the associated nucleic acid biopolymers by the target cell protein via one or more distinct mechanisms.

In some forms, the antibody or antigen binding fragment binds specifically to an epitope. The epitope can be a linear epitope. The epitope can be specific to one cell type or can be expressed by multiple different cell types. In other forms, the antibody or antigen binding fragment thereof can bind a conformational epitope that includes a 3-D surface feature, shape, or tertiary structure at the surface of the target cell.

In some forms, the antibody or antigen binding fragment that binds specifically to an epitope on the target cell can only bind if the protein epitope is not bound by a ligand or small molecule.

Various types of antibodies and antibody fragments can be used to modify nucleic acid biopolymers, including whole immunoglobulin of any class, fragments thereof, and synthetic proteins containing at least the antigen binding variable domain of an antibody. The antibody can be an IgG antibody, such as IgG1, IgG2, IgG3, or IgG4 subtypes. An antibody can be in the form of an antigen binding fragment including a Fab fragment, F(ab')2 fragment, a single chain variable region, and the like. Antibodies can be polyclonal, or monoclonal (mAb). Monoclonal antibodies include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they specifically bind the target antigen and/or exhibit the desired biological activity (U.S. Pat. No. 4,816,567; and Morrison, et al., Proc. Natl. Acad. Sci. USA, 81: 6851-6855 (1984)). The antibodies can also be modified by recombinant techniques, for example by deletions, additions or substitutions of amino acids, to increase efficacy of the antibody in mediating the desired function. Substitutions can be conservative substitutions. For example, at least one amino acid in the constant region of the antibody can be replaced with a different residue (see, e.g., U.S. Pat. Nos. 5,624,821; 6,194,551; WO 9958572; and Angal, et al., Mol. Immunol. 30:105-08 (1993)). In some cases changes are made to reduce undesired activities, e.g., complement-dependent cytotoxicity. The antibody can be a bi-specific antibody having binding specificities for at least two different antigenic epitopes. In one form, the epitopes are from the same antigen. In another form, the epitopes are from two different antigens. Bi-specific antibodies can include bi-specific antibody fragments (see, e.g., Hollinger, et al., Proc. Natl. Acad. Sci. U.S.A., 90:6444-48 (1993); Gruber, et al., *J. Immunol.*, 152:5368 (1994)).

Antibodies that target the biopolymers to a specific epitope can be generated by any techniques known in the art. Exemplary descriptions of techniques for antibody generation and production include Delves, Antibody Production: Essential Techniques (Wiley, 1997); Shephard, et al., Monoclonal Antibodies (Oxford University Press, 2000); Goding, Monoclonal Antibodies: Principles And Practice (Academic Press, 1993); and Current Protocols In Immunology (John Wiley & Sons, most recent edition). Fragments of intact Ig molecules can be generated using methods well known in the art, including enzymatic digestion and recombinant techniques.

c. Dyes or Other Detectable Labels

In some forms, biopolymers include one or more molecules that act as a detectable label or dye.

In some forms, the label is an optically-detectable moiety (e.g., a fluorophore). Non-limiting examples of types of optically-detectable labels include a fluorescent, chemiluminescence, or electrochemically luminescent label. Examples of fluorescent labels include, but are not limited to, 4-acetamido-4'-isothiocyanatostilbene-2,2'disulfonic acid; acridine and derivatives thereof such as acridine, acridine isothiocyanate; 5-(2'-aminoethyl)aminonaphthalene-1-sulfonic acid (EDANS); 4-amino-N-[3-vinylsulfonyl)phenyl]naphthalimide-3,5disulfonate; N-(4-anilino-1-naphthyl)maleimide; anthranilamide; BODIPY; Brilliant Yellow; coumarin and derivatives; coumarin, 7-amino-4-methylcoumarin (AMC, Coumarin 120), 7-amino-4-trifluoromethylcouluarin (Coumaran 15 1); cyanine dyes; cyanosine; 4',6-diamidino-2-phenylindole (DAPI); 5',5"-dibromopyrogallol-sulfonaphthalein (Bromopyrogallol Red); 7-diethylamine-3-(4'-isothiocyanatophenyl)-4-methylcoumarin; diethylenetriamine pentaacetate; 4,4'-diisothiocyanatodihydro-stilbene-2,2'-disulfonic acid; 4,4'-diisothiocyanatostilbene-2,2'-disulfonic acid; 5-[dimethylaminolnaphthalene-1-sulfonyl chloride (DNS, dansylchloride); 4-dimethylaminophenylazophenyl-4'-isothiocyanate (DABITC); eosin and derivatives; eosin, eosin isothiocyanate, erythrosin and derivatives; erythrosin B, erythrosin, isothiocyanate; ethidium; fluorescein and derivatives; 5-carboxyfluorescein (FAM), 5-(4,6-dichlorotriazin-2-yl)aminofluorescein (DTAF), 2',7'-dimethoxy-4'5'-dichloro-6-carboxyfluorescein, fluorescein, fluorescein isothiocyanate, QFITC, (XRITC); fluorescamine; IR144; IR1446; Malachite Green isothiocyanate; 4-methylumbelliferoneortho cresolphthalein; nitrotyrosine; pararosanilin; Phenol Red; B-phycoerythrin; o-phthaldialdehyde; pyrene and derivatives: pyrene, pyrene butyrate, succinimidyl 1-pyrene; butyrate quantum dots; Reactive Red 4 (Cibacron™ Brilliant Red 3B-A) rhodamine and derivatives: 6-carboxy-X-rhodamine (ROX), 6-carboxyrhodamine (R6G), lissamine rhodamine B sulfonyl chloride rhodamine (Rhod), rhodamine B, rhodamine 123, rhodamine X isothiocyanate, sulforhodamine B, sulforhodamine 101, sulfonyl chloride derivatives of sulforhodamine 101 (Texas Red); N,N,N',N'-tetramethyl-6-carboxyrhodamine (TAMRA); tetramethyl rhodamine; tetramethyl rhodamine isothiocyanate (TRITC); riboflavin; rosolic acid; terbium chelate derivatives; Cy3; Cy5; Cy5.5; Cy7; IRD 700; IRD 800; La Jolta Blue; phthalocyanine; naphthalocyanine; any of the fluorescent labels available from Atto-Tec, such as Atto 390, Atto 425, Atto 465, Atto 488, Atto 495, Atto 520, Atto 532, Atto 550, Atto 565, Atto 590, Atto 594, Atto 610, Atto 611X, Atto 620, Atto 633, Atto 635, Atto 637, Atto 647, Atto 647N, Atto 655, Atto 680, Atto 700, Atto 725, Atto 740, etc.; any of the fluorescent labels available from Dyomics such as DY-630, DY-631, DY-632, DY-633, DY-634, DY-635, DY-636, Dy-647, Dy-648, DY-649, Dy-650, Dy-651, DY-652, etc.; any of the fluorescent labels available from Pierce such as DyLight 405, DyLight 488, DyLight 549, DyLight 633, DyLight 649, DyLight 680, DyLight 800, etc.; any of the fluorescent labels available from AnaSpec such as HiLyte Fluor™ 488 dyes, HiLyte Fluor™ 555 dyes, HiLyte Fluor™ 647 dyes, HiLyte Fluor™ 680 dyes, HiLyte Fluor™ 750 dyes, HiLytePlus™ 555 dyes, HiLytePlus™ 647 dyes, HiLytePius™ 750 dyes, etc.; any of the fluorescent labels available from Denovo Biolables such as Oyster 500, Oyster 550 P, Oyster 550 D, Oyster 556, Oyster 645, Oyster 650 P, Oyster 650 D, Oyster 656, etc.; IRDye® 680, IRDye® 700, IRDye® 700DX, IRDye® 800, IRDye® 800 RS, IRDye® 800 CW, etc.; any of the fluorescent labels available from SETA Biomedicals such as Seta K1-204, Seta K5-3212, Seta K8-1342, Seta K8-1352, Seta K8-1357, Seta K8-1407, Seta K8-1642, Seta K8-1644, Seta K8-1663, Seta K8-1664, Seta K8-1669, Seta K8-3002, Seta K4-1082, Seta K8-1669, Seta K7-545, Seta K7-547, Seta K7-549, Seta K8-1252, Seta K8-1261, Seta K8-1262, Seta K8-1320, Seta K8-1344, Seta K8-1367, Seta K8-1377, Seta K8-1382, Seta K8-1446, Seta K8-1667, Seta K8-1752, Seta K8-1762, Seta K8-1767, Seta K8-1777, Seta K8-1782, etc.

C. Substrates for Solid-Support Based Synthesis

Substrates for use as solid support matrices in methods for the template-free synthesis of biopolymers are described. In some forms, capture tags incorporated into initiator sequences allow the initiator sequence and growing biopolymer to be captured by, adhered to, or coupled to a substrate. Such capture allows simplified washing and handling of the biopolymers, and allows automation of all or part of the method.

Capturing biopolymers on a substrate may be accomplished in several ways. In some forms, capture docks are adhered or coupled to the substrate. Capture docks are compounds or moieties that mediate adherence of a biopolymer by binding to, or interacting with, a capture tag on the fragment. Capture docks immobilized on a substrate allow capture of the biopolymers on the substrate. Such capture provides a convenient way of washing away reaction components that might interfere with subsequent steps.

Solid support substrates for use in the disclosed method can include any solid material to which components of the assay can be adhered or coupled. Examples of substrates include, but are not limited to, materials such as acrylamide, cellulose, nitrocellulose, glass, polystyrene, polyethylene vinyl acetate, polypropylene, polymethacrylate, polyethylene, polyethylene oxide, polysilicates, polycarbonates, teflon, fluorocarbons, nylon, silicon rubber, polyanhydrides, polyglycolic acid, polylactic acid, polyorthoesters, polypropylfumerate, collagen, glycosaminoglycans, and polyamino acids. Substrates can have any useful form including thin films or membranes, beads, bottles, dishes, fibers, woven fibers, shaped polymers, particles and microparticles. Some forms of substrates are plates and beads. A useful form of beads is magnetic beads.

In some forms, the capture dock is an oligonucleotide. Methods for immobilizing and coupling oligonucleotides to substrates are well established. For example, suitable attachment methods are described by Pease et al., Proc. Natl. Acad. Sci. USA 91(11):5022-5026 (1994), and Khrapko et al., Mol Biol (Mosk) (USSR) 25:718-730 (1991). A method for immobilization of 3'-amine oligonucleotides on casein-coated slides is described by Stimpson et al., Proc. Natl. Acad. Sci. USA 92:6379-6383 (1995). A preferred method of attaching oligonucleotides to solid-state substrates is described by Guo et al., Nucleic acids Res. 22:5456-5465 (1994).

In some forms, the capture dock is the anti-hybrid antibody. Methods for immobilizing antibodies to substrates are well established. Immobilization can be accomplished by attachment, for example, to aminated surfaces, carboxylated surfaces or hydroxylated surfaces using standard immobilization chemistries. Examples of attachment agents are cyanogen bromide, succinimide, aldehydes, tosyl chloride, avidin-biotin, photocrosslinkable agents, epoxides and maleimides. A preferred attachment agent is glutaraldehyde. These and other attachment agents, as well as methods for their use in attachment, are described in Protein immobilization: fundamentals and applications, Richard F. Taylor, ed. (M. Dekker, New York, 1991), Johnstone and Thorpe, Immunochemistry In Practice (Blackwell Scientific Publications, Oxford, England, 1987) pages 209-216 and 241-242, and Immobilized Affinity Ligands, Craig T. Hermanson et al., eds. (Academic Press, New York, 1992). Antibodies can be attached to a substrate by chemically cross-linking a free amino group on the antibody to reactive side groups present within the substrate. For example, antibodies may be chemically cross-linked to a substrate that contains free amino or carboxyl groups using glutaraldehyde or carbodiimides as cross-linker agents. In this method, aqueous solutions containing free antibodies are incubated with the solid-state substrate in the presence of glutaraldehyde or carbodiimide. For crosslinking with glutaraldehyde the reactants can be incubated with 2% glutaraldehyde by volume in a buffered solution such as 0.1 M sodium cacodylate at pH 7.4. Other standard immobilization chemistries are known by those of skill in the art.

D. Component Initiation Sequences

Methods for microfluidic device-based synthesis of biopolymers employ initiator sequences. An initiator sequence for use in the microfluidic device-based synthesis of biopolymers includes a recognition site for a catalyst. The initiator sequence will be selected according to class and composition of biopolymer that is to be synthesized.

In some forms, the initiator sequence is a component of the user-defined biopolymer. In other forms, the initiator sequence is not a component of the user-defined polymer, but is removed following or during synthesis, for example, by exposure to one or more specific cutting enzymes.

In some forms, the component initiation sequence includes one or more sequences designed to hybridize or otherwise bind to solid support or stationary-phase objects such as magnetic beads, surfaces, agarose or other polymer beads. In other instances, the component initiation sequence includes one or more sites for conjugation to a molecule. For example, the component initiation sequence can be conjugated to a protein, or non-protein molecule, for example, to enable affinity-binding of the component initiation sequence, or of the synthesized polymer.

In some instances, the initiator is biotinylated for capturing the biopolymer on a streptavidin-coated bead. In some instances, the initiator sequence is modified with chemical moieties. Non-limiting examples include Click-chemistry groups (e.g., azide group, alkyne group, DIBO/DBCO), amine groups, and Thiol groups. In some instances some bases located inside a nucleic acid initiator sequence are modified using base analogs (e.g., 2-Aminopurine, Locked nucleic acids, such as those modified with an extra bridge connecting the 2' oxygen and 4' carbon) to serve as linker to attach functional moieties (e.g., lipids, proteins). Alternatively DNA-binding proteins or guide RNAs can be used to attach secondary molecules to the initiator sequence.

Exemplary component initiation sequences include nearly any single-strand DNA sequence longer than 2, 3, 4, or greater than 4 nucleotides. In one example, the sequence GTCGTCGTCCCCTCAAACT (SEQ ID NO: 22) was used for initiation. In another example, the T7 promoter sequence was used (TAATACGACTCACTATAG; SEQ ID NO: 23). In another possibility, the sequence used for sequencing adapters could be used for initiation such as, for example, the SmrtBell PacBio sequence (ATCTCTCTCTTTTCCTCCTCCTCCGTTGTTGTTGTT-GAGAGAGAT; SEQ ID NO: 24) or the initiator sequence for Oxford Nanopore sequencing devices. In addition, other sequences may be used that include sites for nuclease and restriction enzymes to function such as including a PstI cut site (CTGCAG) or EcoRI cut site (GAATTC).

1. Capture Tags

In some forms the initiator sequence includes one or more capture tags, for example, to couple the initiator/the growing biopolymer to a solid support matrix, or another molecule. Preferably, the capture tag is a compound, such as a ligand or hapten, which binds to or interacts with another compound, such as ligand-binding molecule or an antibody. It is also preferred that such interaction between the capture tag and the capturing component be a specific interaction, such as between a hapten and an antibody or a ligand and a ligand-binding molecule.

A preferred capture tag is biotin. In an exemplary form, the initiator is a biotinylated initiator. In a preferred form the biotinylated initiator is a biotinylated nucleic acid initiator.

In the disclosed method, capture tags incorporated into initiator sequences allow the initiator to be captured by, adhered to, or coupled to a substrate, such as magnetic bead.

E. Component Building Blocks

Component building blocks that can be assembled into biopolymers are described. The component building blocks can be any primary structural unit that an initiator sequence for use in the microfluidic device-based synthesis of biopolymers includes a recognition site for a catalyst.

Exemplary recognition sequences include naturally-occurring nucleotides, amino acids, monosaccharides, lipids, as well as non-naturally occurring derivatives thereof.

1. Nucleotide Component Building Blocks

In some forms, the component building block is a deoxyribonucleotide monomer ("nucleotide"). Nucleotide component building blocks can be naturally-occurring nucleotides, or non-naturally occurring derivatives. For example, when a nucleic acid sequence is synthesized, the microfluidic device is loaded with one or more reservoirs including one or more nucleic acids in a suitable buffer. Exemplary buffers include sterile filtered water and physiological saline.

Exemplary nucleotide component building blocks include, but are not limited to the four standard nucleobases, adenine, guanine, cytosine, and thymine, as well as uracil, and modified variants thereof.

Reservoirs of nucleotide component building blocks can include a single nucleotide species, or mixtures of two or more nucleotides. When reservoirs of nucleotides include mixtures, the relative amounts and/or molar ratios of each nucleotide species can be varied according to the desired compositions of the user-defined sequences to be synthesized. In some forms, the reservoirs of nucleotides include oligomers of two or more nucleic acids covalently linked by a phosphodiester bond. Incorporation of pre-determined oligomers of nucleotides as component building blocks can enhance the speed and efficacy of microfluidic device-based nucleic acid synthesis, reduce errors, include specific functionalized molecules, etc.

In some forms, the reservoir well contains one or more types of naturally occurring nucleotides, or one or more types of functionalized nucleotides, or mixtures, at a concentration of about 100 nM, 200 nM, 300 nM, 400 nM, 500 nM, 600 nM, 700 nM, 800 nM, 900 nM, 1 mM, or more than 1 mM. For example, in certain forms, a droplet of 1 nL of nucleotide component building blocks is split from a source well containing nucleotide component building blocks at a concentration of more than 1 mM.

a. Modified Nucleotides

In some forms, the nucleotide component building blocks are "modified" nucleotides. Modified nucleotides include any non-naturally-occurring derivative of a naturally-occurring deoxyribonucleotide. When modified nucleotides are to be incorporated into growing nucleic acid biopolymers, the modified nucleotides can be present in a reservoir on the microfluidic device (e.g., EWOD chip) as an independently addressed reservoir, or they can be mixed into a reservoir containing native (non-modified) nucleotides. For example, modified nucleotides can be mixed as a percentage or ratio of the total nucleotides within the reservoir. In some forms, the modified nucleotides represent 0.1% or more than 0.1% of the total number of nucleotides in the reservoir, up to or approaching 100% of the total nucleotides in the reservoir, between 0.1% and 100% inclusive, such as 0.1%-0.5%, 1%-2%, 1%-5%, 1%-10%, 10%-20%, 20%-30%, 30%-40%, 40%-50%, or more than 50% of the total, such as 60%, 70%, 75%, 80%, 85%, 90%, 95% or 99% of the total.

When modified nucleotides are used, they can be present in the same or different regions of two or more simultaneously synthesized biopolymers. In some forms, synthesized biopolymers include the same or different numbers of modified nucleotides. In some forms, the modified nucleotides are present at the equivalent position in every simultaneously synthesized biopolymer. Therefore, in some forms, a population of simultaneously synthesized nucleic acids include modified nucleotides at precise locations and in specific numbers or proportions as determined by the input sequence(s). In some forms, synthesized nucleic acids include a defined number or percentage of modified nucleotides at specified positions within the synthesized biopolymer. In some forms, synthesized nucleic acids produced according to the described microfluidic device-based methods include more than a single type of modified nucleic acid.

Modified nucleic acid building blocks can be included to produce structural, and/or functional changes in a synthesized nucleic acid relative to the equivalent non-modified form. In some forms, nucleic acid component building blocks are modified at the base moiety (e.g., at one or more atoms that typically are available to form a hydrogen bond with a complementary nucleotide and/or at one or more atoms that are not typically capable of forming a hydrogen bond with a complementary nucleotide), sugar moiety or phosphate backbone.

In some forms, nucleic acid component building block contain amine-modified groups, such as aminoallyl-dUTP (aa-dUTP) and aminohexylacrylamide-dCTP (aha-dCTP) to allow covalent attachment of amine reactive moieties, such as N-hydroxy succinimide esters (NHS).

In other forms, nucleotide component building blocks include a phosphorothioate modified backbone to increase the stability of the synthesized nucleic acid relative to non-modified nucleic acids, for example, to protect against or reduce degradation by exonuclease.

Exemplary modified nucleotide component building blocks include, but are not limited to, diaminopurine, S2T, 5-fluorouracil, 5-bromouracil, 5-chlorouracil, 5-iodouracil, hypoxanthine, xantine, 4-acetylcytosine, 5-(carboxyhydroxylmethyl)uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-D46-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3)w, and 2,6-diaminopurine, pyrazolo[3,4-d]pyrimidines, 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-propynyl uracil and cytosine, 6-azo uracil, cytosine and thymine, 5-uracil (pseudouracil), 4-thiouracil, 8-halo (e.g., 8-bromo), 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 8-azaguanine and 8-azaadenine, deazaguanine, 7-deazaguanine, 3-deazaguanine, deazaadenine, 7-deazaadenine, 3-deazaadenine, pyrazolo[3,4-d]pyrimidine, imidazo[1,5-a]1,3,5 triazinones, 9-deazapurines, imidazo[4,5-d]pyrazines, thiazolo[4,5-d]pyrimidines, pyrazin-2-ones, 1,2,4-triazine, pyridazine; and 1,3,5 triazine.

In some forms, the nucleotide component building blocks are locked nucleic acids (LNA) or peptide nucleic acids (PNA).

i. Locked Nucleic Acids

In some forms, the component building blocks are locked nucleic acids (LNA). LNA is a family of conformationally locked nucleotide analogues which, amongst other benefits, imposes truly unprecedented affinity and very high nuclease resistance to DNA and RNA oligonucleotides (Wahlestedt, et al., *Proc. Natl Acad. Sci. USA*, 975633-5638 (2000); Braasch, et al., *Chem. Biol.* 81-7 (2001); Kurreck, et al., *Nucleic Acids Res.* 301911-1918 (2002)). In some forms, the nucleic acids are synthetic RNA-like high affinity nucleotide analogue, locked nucleic acids. In some forms, the nucleotides are locked nucleic acids.

ii. Peptide Nucleic Acid (PNA)

In some forms, the component building blocks are peptide nucleic acid (PNA). PNA is a nucleic acid analog in which the sugar phosphate backbone of natural nucleic acid has been replaced by a synthetic peptide backbone usually formed from N-(2-amino-ethyl)-glycine units, resulting in an achiral and uncharged mimic (Nielsen P E et al., Science 254, 1497-1500 (1991)). It is chemically stable and resistant to hydrolytic (enzymatic) cleavage. In some forms, the scaffolded DNAs are PNAs. In other forms, the nucleotide component building blocks are PNAs. In some forms PNAs, DNAs, RNAs, or LNAs are used for capture, or proteins or other small molecules of interest to target, or otherwise interact with complementary binding sites on structured RNAs, or DNAs. In other forms, a combination of PNAs, DNAs, RNAs and/or LNAs is used in the microfluidic device-based synthesis of nucleic acids.

In some forms, a combination of PNAs, DNAs, and/or LNAs is used for the microfluidic device-based synthesis of nucleic acids. In some forms, the nucleic acids produced according to the described methods are modified to incorporate fluorescent molecules. Exemplary fluorescent molecules include fluorescent dyes and stains, such as Cy5 modified CTP.

b. Nucleotide Inhibitors

In some forms, component building blocks include nucleotide analogs that inhibit or prevent addition of subsequent nucleotides to the growing nucleic acid, such as "inhibitory nucleotide analogs". Exemplary inhibitory nucleotide analogs include a charged inhibitory group that, upon incorporation into a growing nucleic acid, prevents subsequent nucleotide incorporation until the inhibitory group is removed. Therefore, in some forms, inhibitory nucleotide analogs include a nucleotide triphosphate, a linker (or tether), a detectable label, and a charged inhibitory group, wherein the label and the inhibitory group are removable.

In some forms, an inhibitor group can cause inhibition of subsequent nucleotide incorporation without steric hindrance. For example, the inhibition is caused by chemical or charge interaction with the enzyme and not be a physical blocking of the enzyme. In other forms, the charged inhibitor also provides steric inhibition of enzyme activity. Therefore, in some forms, component building blocks include one or more inhibitory nucleotide analogs including a charged inhibitor group that provides steric hindrance, or which does not provides steric hindrance.

In some forms, the inhibitor moiety is negatively charged or capable of becoming a negatively charged. In other forms, the inhibitor moiety is positively charged or capable of becoming positively charged. In some forms, the Inhibitor includes a charged moiety (e.g., a negatively charged moiety, a positively charged moiety, or both) or a moiety that is capable of becoming charged. The Inhibitor can include two or more charged groups. In some forms, the Inhibitor includes a charged group selected from the group consisting of —COOH, —PO4, —SO4, —SO3, —SO2, —NRwRv, where Rw and Rv independently is H, an alkyl or aryl group. In some forms, the inhibitor moiety does not comprise a —PO4 group. In some other forms, the inhibitor moiety does not comprise an aryl group. In certain other forms, the inhibitor does not include a nucleotide or nucleoside or analogs thereof.

2. Amino Acid Component Building Blocks

In some forms, the component building blocks are naturally occurring amino acids, or derivatives thereof. For example, when a polypeptide sequence is synthesized, the microfluidic device (e.g., EWOD chip) is loaded with one or more reservoirs including one or more amino acids in a suitable buffer. Exemplary buffers include sterile filtered water and physiological saline.

Exemplary amino acid component building blocks include, but are not limited to the twenty standard amino acids (alanine, glycine, cysteine, arginine, aspartic acid, asparagine, histidine, lysine, glutamine, methionine, glutamic acid, threonine, proline, leucine, serine, valine, isoleucine, phenylalanine, tyrosine, tryptophan) in L-forms or D-forms, and modified variants thereof.

a. Modified Amino Acids

In some forms, the amino acid component building blocks are modified amino acids. For example, any of the twenty standard amino acids ca be modified by the addition of a chemical entity such as a carbohydrate group, a phosphate group, a farnesyl group, an isofarnesyl group, a fatty acid group, a linker for conjugation, functionalization, or other modification, etc. Additional modifications include acetylation, propionylation, methylation, myristoylation, palmitoylation to add one or more acetyl, methyl, myristoyl, or palmitoyl groups to an amino acid. Exemplary modified amino acids include hydroxy proline, γ-carboxyglutamate, O-phosphoserine, β-alanine, α-amino butyric acid, γ-amino butyric acid, α-amino isobutyric acid, ε-amino caproic acid, 7-amino heptanoic acid, β-aspartic acid, ε-glutamic acid, cysteine (ACM), ε-lysine, ε-lysine (A-Fmoc), methionine sulfone, norleucine, norvaline, ornithine, d-ornithine, p-nitro-phenylalanine, hydroxy proline, and thioproline.

b. Amino Acid Inhibitors

In some forms, component building blocks include amino acid analogs that inhibit or prevent addition of subsequent amino acids to the growing polypeptide, such as "inhibitory amino acid analogs". Exemplary inhibitory amino acid analogs include a charged inhibitory group that, upon incorporation into a growing polypeptide, prevents subsequent amino acid incorporation until the inhibitory group is removed. Therefore, in some forms, inhibitory amino acids include a linker (or tether), a detectable label, and a charged inhibitory group, wherein the label and the inhibitory group are removable.

In some forms, component building blocks include a peptide of 2 to 20 units of amino acids or analogs, a peptide of 2 to 10 units of amino acids or analogs, a peptide of 3 to 7 units of amino acids or analogs, a peptide of 3 to 5 units of amino acids or analogs. In some embodiments, the Inhibitor includes a group selected from the group consisting of Glu, Asp, Arg, His, and Lys, and a combination thereof (e.g., Arg, Arg-Arg, Asp, Asp-Asp, Asp, Glu, Glu-Glu, Asp-Glu-Asp, Asp-Asp-Glu or AspAspAspAsp). Peptides or groups may be combinations of the same or different amino acids or analogs.

3. Carbohydrate Component Building Blocks

In some forms, the component building blocks are naturally occurring monosaccharides, or derivatives thereof. For example, when a oligosaccharide sequence is synthesized, the microfluidic device (e.g., EWOD chip) is loaded with one or more reservoirs including one or more monosaccharides in a suitable buffer. Exemplary buffers include sterile filtered water and physiological saline.

Exemplary monosaccharide component building blocks include, but are not limited to glucose (dextrose), fructose, galactose, ribose, xylose, allose, N- or O-substituted derivatives of neuraminic acid, and modified variants thereof. In some forms, the monosaccharide component building blocks can be α-anomers, or β-anomers of D-isomers, L-isomers, or combinations thereof.

In some forms, monosaccharide component building blocks are modified with lipids,

4. Other Polymer Building Blocks

For example, a non-limiting list of polymer building blocks that can be coupled to synthetic nucleic acids prepared using microfluidic device-based methods includes poly(beta-amino esters); aliphatic polyesters; polyphosphoesters; poly(L-lysine) containing disulfide linkages; SOMA-MERS® (see, Hensley, *Journal of Biomolecular Techniques*: TBT. 2013; 24(Suppl):S5); poly(ethylenimine) (PEI); disulfide-containing polymers such as DTSP or DTBP crosslinked PEI; PEGylated PEI crosslinked with DTSP; Crosslinked PEI with DSP; Linear SS-PEI; DTSP-Crosslinked linear PEI; branched poly(ethylenimine sulfide) (b-PEIS). Typically, the polymer has a molecular weight of between 500 Da and 20,000 Da, inclusive, for example, approximately 1,000 Da to 10,000 Da, inclusive. In some forms, the polymer is ethylene glycol. In some forms, the polymer is polyethylene glycol. In an exemplary form, one or more polymer are conjugated to the modified nucleic acids at one or more positions in the sequence.

F. Enzyme Catalysts

Methods for template-free synthesis of biopolymers require catalysts to enable the addition of each component building block onto the initiator sequence. Useful catalysts enable or increase the rate of incorporation of a component building block onto the biopolymer.

Exemplary catalysts enzymes are matched to a corresponding initiator sequence. For example, in some forms, the initiator sequence is selected according to class and composition of the catalyst used for the synthesis.

In some forms, the catalyst includes one or more sequences designed to hybridize or otherwise bind to a solid support or stationary-phase objects such as magnetic beads, surfaces, agarose or other polymer beads. In other instances, the catalyst includes one or more sites for conjugation to a molecule. For example, the catalyst can be conjugated to a protein, or non-protein molecule, for example, to enable affinity-binding of the catalyst, for example, to remove the catalyst from the synthesized polymer.

1. Enzyme Catalysts for Nucleic Acid Synthesis

Exemplary catalysts useful for the enzymic template-free synthesis of nucleic acids include Terminal deoxynucleotidyl transferases (TdT), Telomerases and Qbeta replicases.

a. Terminal Deoxynucleotidyl Transferases

Terminal deoxynucleotidyl transferase (TdT), also known as DNA nucleotidylexotransferase (DNTT), or terminal transferase, is a specialized DNA polymerase.

TdT is a template independent polymerase that catalyzes the addition of deoxynucleotides to the 3' hydroxyl terminus of DNA molecules. TdT is a member of the Pol X family TdT catalyses the template-free addition of nucleotides to the 3' terminus of a DNA molecule. The preferred substrate of this enzyme is a 3'-overhang, but it can also add nucleotides to blunt or recessed 3' ends. Cobalt is a necessary cofactor, however the enzyme catalyzes reaction upon Mg and Mn administration in vitro. TdT does not discriminate among the four base pairs when adding them to the N-nucleotide segments, it has shown a bias for guanine and cytosine base pairs.

TdT is used to add labeled nucleotides to one or more termini of a nucleic acid (e.g., DNA). for radio-labeling, cloning, and other labeling strategies. Commercially sources of TdT enzymes are known in the art (e.g., NEB Catalog. #M0315).

In some forms, the DNA polymerase is DNA polymerase mu (Pol μ). Pol μ displays intrinsic terminal deoxynucleotidyltransferase activity and a strong preference for activating $Mn^{2+}$ ions.

A number of error-prone DNA polymerases efficiently incorporate nucleotides in DNA lesions where template information is missing (Goodman, *Annu Rev Biochem.* 71:17-50 (2002)). In some forms, the DNA polymerase is a Y-family DNA polymerase. Rev1, which was originally identified and isolated because of its UV-induced expression and UV sensitivity in its absence, is present universally among eukaryotes. Rev1 is a template-independent deoxycytidyl transferase (Lawrence C W et al., J. Mol. Biol. 122(1), 1-21(1978)). Protruding, recessed or blunt-ended double or single-stranded DNA molecules serve as a substrate for TdT. The 58.3 kDa enzyme does not have 5' or 3' exonuclease activity. The addition of Co' in the reaction makes tailing more efficient.

An exemplary reaction buffer for TdT includes 50 mM Potassium Acetate, 20 mM Tris-acetate, and 10 mM Magnesium Acetate (pH 7.9 @ 25° C.)

b. Telomerase

Telomerase is another example of a DNA-template free polymerase. Telomerase is a special reverse transcriptase that extends one strand of the telomere repeat by using a template embedded in an RNA subunit. However, in the presence of manganese, both yeast and human telomerase can switch to a template- and RNA-independent mode of DNA synthesis, acting in effect as a terminal transferase (Lue, et al., *PNAS.* 102 (28) 9778-9783 (2005)).

c. Q-Beta Replicase

Qbeta replicase is another example of template free polymerase for nucleic acids, in particular for RNA (Biebricher et al., *Nature.* 321(6065):89-91(1986) Biebricher et al., *EMBO J,* 15(13): 3458-3465 (1996)).

RNA-dependent RNA polymerase (RdRP), (RDR), or RNA replicase, is an enzyme that catalyzes the replication of RNA from an RNA template. This is in contrast to a typical DNA-dependent RNA polymerase, which catalyzes the transcription of RNA from a DNA template.

G. Buffers and Wash Reagents

In some forms, methods for microfluidic device-based synthesis of biopolymers employ buffers and wash reagents. Wash buffers can be any solution that is used to remove or reduce the local concentration of another component, for example, an enzyme.

Exemplary buffers and wash reagents include water, physiological salt solutions, for example, PBS, and DMEM.

1. Stop Reagents and Blocking Buffers

In some forms, methods for microfluidic device-based synthesis of biopolymers employ blocking buffers and stop reagents. Blocking buffers are used to prevent or reduce the activity of a catalyst, for example, a polymerase enzyme. In some forms, the stop or block reagent quenches the enzymic catalysis that incorporates the component building block onto the growing biopolymer chain. Typically, the methods include stop reagents and/or blocking reagents that are specific or effective to stop, reduce or otherwise mediate the activity of the catalyst enzyme that is employed. Blocking buffers and stop reagents effective for specific catalyst enzymes are known in the art.

In some forms, the methods include the enzyme TdT as a catalyst for addition of nucleic acids to a nucleic acid biopolymer. Therefore, the methods provide inhibitors for the inhibition of TdT. Exemplary inhibitors of TdT include metal chelators (e.g., EDTA), sodium, ammonium, chloride, iodide, phosphate ions, and TRIS buffer. Therefore, in some forms, the stop buffer for TdT includes one or more of EDTA, sodium, ammonium, chloride, iodide, phosphate ions, and TRIS buffer. Exemplary inhibitors of TdT polymerase include Genistin and Heptelidic acid.

Exemplary inhibitors of telomerase enzymes include BIBR 1532, BRACO 19 trihydrochloride, Costunolide, RHPS 4 methosulfate, TMPyP4 tosylate. Exemplary inhibitors of DNA polymerase include amikhelline, actinomycin D, aphidicolin, cytarabine, mithramycin A, 7-Aminoactinomycin D, rifamycin SV monosodium salt, 1-beta-D-Arabinofuranosylcytosine, 2prime-O-Methyl Guanosine, acridine orange hemi(zinc chloride) salt, deacetylcolchiceine, Foscarnet sodium, rubrofusarin, rugulosin, resistomycin, juglone, alpha-amanitin, rifapentine, and vernolepin. Exemplary inhibitors of RNA polymerase include amatoxins (10 P), RNA Polymerase III Inhibitor, and rifamycin antibiotics, aureothricin, 2prime-C-Methyl Cytidine, and Thiolutin.

In some forms, stop reagents include one or more inhibitory component building blocks, for example, one or more inhibitory nucleotide analogs, or one or more inhibitory amino acids.

In some forms, stop reagents include molecules that immediately prevent activity of a catalyst enzyme. An exemplary agent that immediately prevents the activity of a catalyst enzyme is a molecule that sequesters and/or chelates one or more enzyme co-factors. Exemplary co-factor that can be sequestered include ions, such as metal ions.

In some forms, a stop reagent includes one or more molecules that chelate ions. In some forms, the methods include chelating agents that chelate Mg2+ ions. Chelating agents that chelate enzyme co-factors are known in the art. Exemplary chelating agents include EDTA, BAPTA and EGTA.

EDTA (ethylenediaminetetraacetic acid) is an aminopolycarboxylic acid and a colorless, water-soluble solid. Its conjugate base is ethylenediaminetetraacetate. It is a widely used chelating agent to sequester metal ions such as Ca2+ and Fe3+. After being bound by EDTA into a metal complex, metal ions remain in solution but exhibit diminished reactivity. EDTA is produced as several salts, notably disodium EDTA and calcium disodium EDTA.

EGTA (ethylene glycol-bis(β-aminoethyl ether)-N,N,N',N'-tetraacetic acid), also known as egtazic acid (INN, USAN), is an aminopolycarboxylic acid, a chelating agent. It is a colourless solid that is related to the better known EDTA. Compared to EDTA, it has a lower affinity for magnesium, making it more selective for calcium ions.

In some forms, the activity of one or more stop or blocking reagents is enhanced or enabled by one or more external factors. For example, in some forms, TdT enzymes are inactivated by heating at 70° C. for 10 minutes. The heating can occur in the presence of one or more stop reagents, such as EDTA.

H. Encapsulation Agents

In some forms, sequence-encoded polymers are packaged into discrete SMOs via encapsulation. Suitable encapsulating agents include gel-based beads, protein viral packages, micelles, mineralized structures, siliconized structures, or polymer packaging.

In some forms, the encapsulating agents are viral capsids or a functional part, derivative and/or analogue thereof. In some forms, the encapsulating agents are lipids forming micelles, or liposomes surrounding the nucleic acid encoding a format of information. In some forms, the encapsulating agents are natural or synthetic polymers. In some forms, the encapsulating agents are mineralized, for example, calcium phosphate mineralization of alginate beads, or polysaccharides. In other forms, the encapsulating agents are siliconized. Packaging of bitstream polymer sequences into memory blocks allows for selection and superstructuring by use of molecular identifiers, or "addresses". In addition to nucleic acid overhangs, other purification tags can be incorporated into the overhang nucleic acid sequence in any SMOs for purification (i.e. data retrieval). In some forms, the overhang contains one or more purification tags. In some forms, the overhang contains purification tags for affinity purification. In some forms, the overhang contains one or more sites for conjugation to a nucleic acid, or non-nucleic acid molecule. For example, the overhang tag can be conjugated to a protein, or non-protein molecule, for example, to enable affinity-binding of the SMOs. Exemplary proteins for conjugating to overhang tags include biotin, antibodies, or antigen-binding fragments of antibodies.

I. Reagents for Modification of Biopolymers

Biopolymers designed and synthesized according to the described microfluidic device-based methods can be modified to add, remove, modify or otherwise interact with molecules having a known function.

Exemplary modifying moieties can be selected according to the biopolymer, and can include small molecules, proteins, peptides, nucleic acids, lipids, saccharides, or polysaccharides.

a. Enzymes for Modifying Nucleic Acids

Enzymes that modify one or more components of a nucleic acid biopolymer are described for use with the described methods. Enzymes that degrade, cleave or otherwise remove one or more nucleotides at one or more sites within a nucleic acid are provided.

i. Exonucleases

In some forms the methods employ one or more exonucleases to remove one or more nucleic acids from either end of a nucleic acid biopolymer. Exonuclease enzymes, and appropriate buffer conditions for optimal exonuclease activity are known in the art. Exemplary exonuclease enzymes include Lambda Exonuclease, *E. coli* Exonuclease I, Exonuclease II, *E. coli* Exonuclease III, Exonuclease V, Exonuclease VI, Exonuclease VII, and Exonuclease T.

ii. Endonucleases

In some forms the methods employ one or more endonucleases to remove one or more nucleic acids from within a nucleic acid biopolymer. Endonuclease enzymes, and appropriate buffer conditions for optimal exonuclease activity are known in the art. Exemplary endonuclease enzymes include Mung Bean Nuclease, DNase I, Micrococcal Nuclease, T7 Endonuclease I, Thermostable FEN1, and Nuclease BAL-31.

iii. Restriction Endonucleases

In some forms the methods employ one or more restriction endonucleases to cut, cleave or remove one or more nucleic acids at a sequence-controlled region of a biopolymer. Restriction endonucleases (RE) are enzymes that cut the sugar-phosphate backbones of complementary nucleic acids within the DNA double helix to produce blunt-ended nucleic acid fragments (i.e., both strands terminate in a base pair). Restriction endonuclease enzymes that recognize a specific sequence of nucleotides and cut both strands of DNA to yield blunt-ended DNA fragments are well known in the art. Recognition sequences for restriction endonuclease enzymes are generally between 4 and 8 bases. Restriction endonuclease enzymes that digest double stranded DNA to produce a blunt-ended DNA fragments (i.e., blunt-cutting RE) can recognize palindromic or non-palindromic sequences. The cut site can be within the recognition sequence, or can be contiguous with the recognition sequence, or at a distance from the recognition sequence. A non-limiting list of blunt-end restriction endonuclease enzymes includes AanI, Acc16I, AccBSI, AccII, AcvI, AfaI, AfeI, AhaIII, AjiI, AleI, AluBI, AluI, Aor51HI, Asp700I, AssI, BalI, BbrPI, BmcAI, BmgBI, BmiI, BoxI, BsaAI, BsaBI, Bse8I, BseJI, Bsh1236I, BshFI, BsnI, Bsp68I, BspFNI, BspLI, BsrBI, BssNAI, Bst1107I, BstBAI, BstC8I, BstFNI, BstPAI, BstSNI, BstUI, BstZ17I, BsuRI, BtrI, BtuMI, Cac8I, CdiI, CviJI, CviKI_1, CviRI, DinI, DpnI, DraI, Ec113611, Eco105I, Eco147I, Eco32I, Eco47III, Eco53kI, Eco72I, EcoICRI, EcoRV, EgeI, EheI, EsaBC3I, FaiI, FnuDII, FspAI, FspI, GlaI, Had, HaeIII, HincII, HindII, HpaI, Hpy166II, Hpy8I, HpyCH4V, KspAI, LpnI, MalI, MbiI, MlsI, MluNI, MlyI, MroXI, MscI, Ms1I, Msp20I, MspA1I, MssI, MstI, MvnI, NaeI, NlaIV, NruI, NsbI, NspBII, OliI, PceI, PdiI, PdmI, PmaCI, PmeI, PmlI, Ppu21I, PshAI, PsiI, PspCI, PspN4I, PvuII, RruI, RsaI, RseI, ScaI, SchI, SciI, SfoI, SmaI, SmiI, SmiMI, SnaBI, SrfI, SseBI, SspD5I, SspI, Sth302II, StuI, SwaI, XmnI, ZraI, and ZrmI

V. Uses

The described methods and compositions for automated template-free synthesis and manipulation of sequence controlled biopolymers can be used for a wide range of applications. Exemplary applications include preparation and organization of biopolymer-based memory systems.

A. Microfluidic Synthesis for Nucleic Acid Memory

The described methods for the design, synthesis and/or manipulation of biopolymers using microfluidic devices can be implemented for automated large-scale simultaneous production of a multiplicity of uniquely addressed, user-defined biopolymers.

The methods can synthesize biopolymers for use in a wide variety of applications, including for biopolymer-based memory storage. In some forms, the methods include organizing information within memory storage units, such as nucleic acid, or polypeptide encapsulation units, through movement of droplets actuated through a microfluidics platform. In further forms, the methods include retrieving the bitstream-encoded sequence from the biopolymer memory storage units.

1. Nucleic Acid Memory Storage

Methods of synthesizing and manipulating user-defined nucleic acids for memory storage are provided. In some forms, microfluidic systmes are implemented to synthesize and manipulate data-sequence nucleic acids encoding a format of data are encapsulated within a layer of natural, or synthetic material. A nucleic acid of any arbitrary form can be encapsulated, for example, a linear, a single-stranded, base-paired double stranded, or a scaffolded nucleic acid. Exemplary encapsulating agents include proteins, lipids, saccharides, polysaccharides, nucleic acids, and any derivatives thereof, as well as hydrogel and synthetic polymers including polystyrene, or silica, glass, and paramagnetic materials. These encapsulated nucleic acids form discrete memory storage units that allow for controlled segregation of blocks of information. In some forms, the methods also optionally include organizing information within nucleic acid memory storage units. In some forms, the methods also optionally include accessing the data-encoded sequence, for example, accessing bitstream-encoded data from an enclosed nucleic acid sequence. In some forms, the methods also include steps of retrieving the bitstream-encoded sequence from the biopolymer memory storage units.

Methods for microfluidic-based production of biopolymers and particles encapsulating biopolymers can be applied for the creation of nucleic acid memory objects for storage of information using nucleic acids of any length, or any form have also been developed. Typically, nucleic acids of any desired length are packaged, encapsulated, enveloped, or encased in gel-based beads, protein viral packages, micelles, mineralized structures, siliconized structures, or polymer packaging, herein referred to as "nucleic acid package". In some forms, linear nucleic acids, encoding a bitstream of information, are base-paired, double-stranded. In other forms, linear nucleic acids consist of a long continuous single-stranded nucleic acid polymer or many such polymers. These discrete nucleic acid packages serve as nucleic acid memory objects (NMOs) and allow incorporation of one or more specific tags on the surface of the structures. Some exemplary tags include nucleic acid sequence tags, protein tags, carbohydrate tags, and any affinity tags.

The manner in which the indices/barcodes are attached to the external surface of the core particle and/or biopolymer sequence can be varied according to the desired manner for pooling, sorting, organizing and accessing the information. In other forms, encapsulated particle are formed in which the "shell" that is the product of "shelling" contains the encoded data.

Typically, the methods for assembling and storing a desired media as sequence-controlled polymer memory object (SMO) include one or more of the following steps:
  (A) Providing a bitstream encoded sequence containing the desired media;
  (B) Creating a sequence-controlled polymer memory object (SMO) including the bitstream encoded sequence; and
  (C) Storing the SMO including the bitstream encoded.

In some forms, the methods also include one or more of the following steps:
  (D) Organizing or combining information within two or more SMOs;
  (E) Retrieving the bit stream encoded sequence within one or more selected SMOs; and
  (F) Accessing the media encoded within the selected SMO.

Each of these steps can be implemented within microfluidic devices to control the movement of droplets or fluid flow to organize the synthesis, manipulation, storage and retrieval of encoded information.

a. Conversion of Data to Biopolymer Sequence

Typically, the methods require providing a polymer sequence that encodes a piece of desired information, such as bitstream data. Suitable polymers include sequence-controlled polymers, such as macromolecules composed of a non-random sequence of discrete monomers. An exemplary sequence-controlled polymer is a nucleic acid, such as single or double-stranded DNA, or RNA. For example, in some forms, a single-stranded nucleic acid sequence encoding bitstream data is input for the design of a nucleic acid nanostructure having a user-defined shape and size.

In some forms, a portion or portions of a digital format of information, such as an html format of information or any other digital format such as a book with text and/or images, audio, or movie data, is converted to bits, i.e., zeros and ones. In some forms, the information can be otherwise converted from one format (e.g., text) to other formats such as through compression by Lempel-Ziz-Markov chain algorithm (LZMA) or other methods of compression, or through encryption such as by Advanced Encryption Standard (AES) or other methods of encryption. Other formats of information that can be converted to bits are known to those of skill in the art.

Therefore, in some forms, the methods include converting a format of information into one or more bit sequences of a bit stream. One or more bit sequences can be converted into one or more corresponding polymer subunits. In an exemplary form, bit sequences are converted to nucleic acid sequences. Methods for converting bit sequences into one or more sequence-controlled polymers are known in the art.

In exemplary forms, a digital file, encoded on a computer as a bit stream of 0's and 1's, is reversibly converted to a nucleic acid sequence using any of the methods known in the art.). In some forms, an oligonucleotide or DNA using a 1 bit per base encoding (A or C=0; T or G=1) to form a corresponding encoded oligonucleotide sequence, i.e. the oligonucleotide sequence corresponds to or encodes for the bit sequence. In some forms the choice of digital format, for example the encryption salt, and the choice of bitstream to equivalent nucleic acid sequence, for example choice of A rather than C, is optimized such that the sequence repetition and sequence self-complementarity are avoided, identified by methods known to the art.

The nucleic acid sequence generated from the bit stream data of a desired media is termed the "bit stream encoded sequence". The bit stream data encoded within the long scaffold sequence is typically "broken-up" into fragments. For example, data can be fragmented into any size range from about 100 to about 1,000,000 nucleotides, such as from about 375 to about 51,000 bases, inclusive, per object, for example, 500 bp up to 50,000 bp. In the digital storage field this is conceptually synonymous with "page" or "block". The bit stream-encoded nucleic acid sequence is synthesized according to the described template-free synthesis methods using a microfluidic device, and is optionally amplified or purified using a variety of known techniques (i.e., asymmetric PCR, bead-based purification and separation, cloning and purification).

In some forms, the memory page will have identifying information as part of each sequence, including a file format signature, a sequence encoding an encryption salt, a unique identifying page number, a memory block length, and a sequence for DNA amplification.

In an exemplary form, a digital file is compressed, for example, using the LZMA method, or the file is encrypted, for example, using AES128 encryption using a supplied password.

In some forms, the methods include synthesizing, or otherwise providing a nucleic acid sequence from a pool containing a multiplicity of similar or different sequences. In some forms, the pool is a database of known sequences. For example, in certain forms a discrete "block" of information is contained within a pool of nucleic acid sequences ranging from about 100-1,000,000 bases in size, though this upper limit is theoretically unlimited. In some forms, the nucleic acid sequences within a pool of multiple nucleic acid sequences share one or more common sequences. When nucleic acids that are provided are selected from a pool of sequences, the selection process can be carried out manually, for example, by selection based on user-preference, or automatically.

b. Assembly of Memory Objects

Assembly of memory objects by encapsulation, or direct assembly of sequence-encoded biopolymers and address tags/barcodes can be carried out according the described microfluidic-based methods to produce memory objects having a range of different structures. For example, in some forms, memory objects include a core particle, onto which one or more sequence-encoded biopolymers is bound. Binding of sequence encoded biopolymers to a particle core can be achieved according to the microfluidic methods, for example, using enzymes to catalyze covalent or non-covalent linkages. In some forms, a core molecule is coated or coupled to a molecule which is an intermediary receptor, for example, a binding site that is recognized by one or more ligands associated with the sequence encoded biopolymer.

In some forms, sequence-encoded biopolymers are coupled or hybridized to a receptor-coated core molecule. In some forms, the polymer/core substructure is then coated with one or more encapsulating agents (i.e., "molecular shelling") to produce a coated polymer/core structure, which is then coupled to one or more address labels, or barcodes.

Binding of address labels to a coated polymer/core particle can be achieved using covalent or non-covalent linkages, or hybridization of complementary nucleic acids. In some forms, assembly of a memory object includes loading or complexing one or more sequence-encoded biopolymers within the interior space(s) of a porous, or otherwise accessible polymer core molecule or structure. In some forms, assembly of a memory object includes encapsulating, or shelling the polymer-loaded core to create an encapsulated polymer-loaded particle, which is then complexed with one or more address tags or barcodes.

In some forms, memory objects include a sequence-encoded polymer, and optionally core molecules and/or encapsulating agents that are coated with multiple different types of address tags or barcodes. For example, in some forms, memory objects are assembled to enable multiplexed molecular logic operations and data selection. For example, in some forms, encapsulation or molecular shelling of one or more sequence-encoded biopolymers, including multiple pieces of bit-stream encoded data are labelled with multiple address tags or barcodes. The address tags or barcodes can be attached directly to the molecular core, or absorbed by a molecular core are further surrounded by a molecular shell and functionalized with addressing/specificity tags for multiplexed computation.

In some forms, the described methods for microfluidic-actuated movement of droplets synthesize biopolymers into memory objects including:

(i) one or more sequence-encoded biopolymers;
(ii) optionally core molecules or encapsulating agents that are coated with address tags or barcodes; and
(iii) a shell or core which itself produces a signal, or has another property that can be detected and measured to produce a readout.

The outer "shell", or inner "core" of a memory particle can, therefore, be used to address or label the memory object. Exemplary physical or chemical properties that can be detected and measured include optical, magnetic, electric, or physical properties.

Therefore, in some forms, the outer shell or inner core of a memory object produces a readout based on optical, magnetic, electric, or physical properties of the shell/core. Therefore, in some forms, data streams are encoded directly on a molecular core, which has a readout based on optical, magnetic, electric, or physical properties of the core. The molecular core also contains address/specificity tags for molecular logic and data retrieval operations. In some forms, the data stream is encoded on a molecular shell surrounding a molecular core. The shell/core has readouts based on the optical, magnetic, electric, or physical properties of the shell/core. The shell is functionalized with addressing/specificity tags for molecular logic and data retrieval operations.

Synthesized biopolymer memory objects prepared according to described microfluidic methods are suitable for many applications. Some exemplary uses include in memory storage, in nano-electronic circuitry, etc. Sequence-controlled biopolymer memory objects including nucleic acids or other sequence-controlled biopolymers that encode a format of data, encapsulated within natural, or synthetic material, are also provided. In some forms, a nucleic acid or other biopolymer of any arbitrary form can be encapsulated. For example, in some forms a linear, a single-stranded, a base-paired double stranded, or a scaffolded nucleic acid is encapsulated. Exemplary encapsulating agents include proteins, lipids, saccharides, polysaccharides, nucleic acids, synthetic polymers, hydrogel polymers, silica, paramagnetic materials, and metals, as well as any derivatives thereof. These encapsulated nucleic acids or other biopolymer are associated with one or more overhang nucleic acid sequences that are used for adding addresses, and/or purification tags. In some forms, multiple layers of encapsulation and overhang nucleic acids are designed for additional sorting and tagging the format of information.

In some forms, the bit stream encoded nucleic acid sequence is not the same sequence as chromosomal DNA, or mRNA, or prokaryotic DNA. For example, in some forms, the entire bit stream encoded sequence has less than 20% sequence identity to a naturally-occurring nucleic acid sequence, for example, less than 10% identity, or less than 5% identity, or less than 1% identity, up to 0.001% identity. In other forms, the bitstream sequences are composed of the sequences of cDNAs, genes, protein sequences, protein coding open reading frames, or biological sequences that together in a pool form a database of biological sequences.

The disclosed compositions and methods can be further understood through the following text.

In some forms, the method is a method for synthesis of a specific nucleic acid sequence programmed by the movement of nucleotides, enzymes, buffer, salts, and water in aqueous droplets using electrowetting on dielectric (EWOD) movement of droplets. In some forms, the method is a method of addressed location synthesis of nucleic acid polymers by the movement of drops containing the next nucleic acid to be added into the drop containing the growing synthesized polymer. In some forms, the microfluidic device is a chip design allowing for the addition of nucleic acids in droplets on the EWOD chip in controlled volumes for the addition to a growing polymer. In some forms, the microfluidic device is a chip design for the stable fixation of a growing nucleic acid polymer to a defined, addressed location on a chip used in EWOD droplet movement. In some forms, the method is a method of simultaneously carrying out instructions in parallel to massively parallelize the synthesis of many different sequences at many different addressed locations across the chip.

Disclosed are methods for synthesizing a biopolymer having a desired size and sequence in the absence of a template, where the method comprises: (a) combining, on a microfluidic device, a droplet comprising a component initiation sequence with one or more droplets collectively comprising a component building block and an attachment catalyst to form a combined droplet; and (b) optionally repeating step (a) to perform the step-wise addition of component building blocks to the biopolymer to form a biopolymer having a preselected, desired polymer sequence and length. The droplets comprises a component initiation sequence and each of the droplets collectively comprising the component building block and the attachment catalyst were, prior to the combining, at different locations on the microfluidic device. One or more additional droplets, each comprising an additional component building block, are at different locations on the microfluidic device than the droplet comprising the component sequence, the droplets collectively comprising the component building block and the attachment catalyst, or the combined droplet. The combining comprises conditions suitable for the attachment catalyst to attach the component initiation sequence to the component building block to form a biopolymer.

In some forms, the conditions suitable for the attachment of the component initiation sequence with the component building block to form a biopolymer in step (a) comprise contacting the combined droplet with one or more reagents selected from the group consisting of a wash reagent, a blocking reagent, and a stop reagent. In some forms, each of the wash reagent, blocking reagent, and stop reagent are provided as independent droplets on the microfluidic device. In some forms, the combining of droplets in step (a) is accomplished by moving one or more of the droplets on the microfluidic device using electrical charge provided by an optic fiber.

In some forms, the sequence of movement for each droplet on the microfluidic device to produce the desired polymer sequence is provided in the form of a computer-readable program. In some forms, two or more biopolymers are simultaneously or consecutively synthesized at different locations of the same microfluidic device. In some forms, the two or more biopolymers have different sequences, different sizes, or both different sequences and different sizes. In some forms, each of the two or more synthesized biopolymers is synthesized and purified at a distinct location on the same microfluidic device. In some forms, each of the two or more biopolymers comprises a unique address tag.

In some forms, the component initiation sequence is coupled to a stable support matrix. In some forms, the support matrix is a bead. In some forms, the bead is magnetic.

In some forms, the droplet is an aqueous droplet having a volume between one femtoliter (fl) and 100 microliters (µl), preferably between one picoliter (pl) and one nanoliter (nl). In some forms, the creation, movement and combination of the droplets on the microfluidic device is controlled by a computer program.

In some forms, the method further comprises (c) manipulating, purifying, or isolating the synthesized biopolymer on the microfluidic device. In some forms, manipulating the synthesized biopolymer in step (c) comprises inducing one or more structural or functional changes in the biopolymer. In some forms, isolating the synthesized biopolymer in step (c) comprises a complexity-reduction step. In some forms, the complexity-reduction step includes isolating the synthesized biopolymer on the basis of one or more properties selected from the group consisting of mass, size, electrochemical charge, hydrophobicity, pH, melting temperature, conformation, and affinity for one or more ligands. In some forms, manipulating the synthesized biopolymer in step (c) comprises incorporating into the biopolymer one or more labels selected from the group consisting of a dye, a fluorescent molecule, a radiolabel, an affinity tag, and a barcode.

In some forms, the method further comprises, prior to step (a), forming one or more of the droplets comprising the component initiation sequence and the droplets collectively comprising the component building block and the attachment catalyst by splitting the droplets from reservoirs that collectively comprise the component initiation sequence, the component building block, and the attachment catalyst.

In some forms, the method further comprises, prior to step (a), forming one or more of the additional droplets by splitting the additional droplets from reservoirs that collectively comprise the additional component building blocks.

In some forms, the biopolymer is a nucleic acid. In some forms, the nucleic acid has a length of between 100 and 100,000 bases in length, between 200 and 10,000 bases in length, between 500 and 5,000 bases, or between 1,000 and 3,000 bases in length. In some forms, one or more of the component building blocks is selected from the group consisting of adenosine, cytidine, guanosine, thymidine, uridine, inosine, uridine, xanthosine, and pseudouridine. In some forms, the nucleic acid is single-stranded DNA.

In some forms, the attachment catalyst is a polymerase enzyme selected from the group consisting of TdT, Qbeta replicase, and telomerase.

In some forms, step (c) comprises the polymerase chain reaction to amplify the synthesized nucleic acid.

In some forms, the method further comprises the step of sequencing the synthesized nucleic acid.

In some forms, one or more droplets comprises a restriction endonuclease and one or more suitable buffers for the effective function of the restriction endonuclease.

Also disclosed are methods for the automated manipulation of a nucleic acid sequence comprising combining, on a microfluidic device, the nucleic acid sequence and one or more endonuclease or exonuclease enzymes, where the combining comprises conditions under which the one or more endonuclease or exonuclease enzymes remove or degrade one or more nucleotides from the nucleic acid sequence to produce a degraded nucleic acid.

In some forms, the nucleic acid is immobilized on a solid support or surface. In some forms, the method further comprises purifying the degraded nucleic acid. In some forms, purifying the degraded nucleic acid comprises washing the degraded nucleic acid on the microfluidic device to remove the one or more endonuclease or exonuclease enzymes.

In some forms, the method further comprises adding one or more nucleotides to the degraded nucleic acid on the microfluidic device, to form a modified nucleic acid. In some forms, adding one or more nucleotides to the degraded nucleic acid comprises: (a) combining, on the microfluidic device, a droplet comprising the degraded nucleic acid with one or more droplets collectively comprising a component building block and an attachment catalyst to form a combined droplet; and (b) optionally repeating step (a) one or more times. The droplets comprise the degraded nucleic acid and each of the droplets collectively comprising the component building block and the attachment catalyst were, prior to the combining, at different locations on the microfluidic device. The combining comprises conditions suitable for the attachment catalyst to attach the degraded nucleic to the component building block to form a modified nucleic acid.

In some forms, the nucleic acid is encodes bitstream data. In some forms, the manipulation is carried out in a region of the nucleic acid that is a barcode. In some forms, the microfluidic device is an electrowetting on dielectric (EWOD) device. In some forms, the nucleic acid is a barcode.

In some forms, the barcode is attached to a nucleic acid memory object. In some forms, the barcode is not the exact sequence of the barcode associated to the concept or metadata, but it mutated away from the barcode by 1, 2, 3, 4, 5, 6, 7, 8, 9, 10, 11, 12, 13, 14, 15, 16, 17, 18, 19, 20, 21, 22, 23, 24, 25, or more than 25 mutations.

In some forms, the mutated barcode is associated with metadata or a concept of the nearest barcode held in a barcode hash table associating to metadata contained within the nucleic acid memory object. In some forms, the mutated barcode is associated with variations of metadata or a concept of the nearest barcode held in a barcode hash table. In some forms, the barcode is associated with metadata describing biological information of the nucleic acid sequence contained in the nucleic acid memory object. In some forms, the nucleic acid sequence is encapsulated within a nucleic acid memory object, where the nucleic acid memory object encodes a gene, and the barcode sequence describes one or more features selected from the group consisting of gene name, mutations of the gene, the source organism, gene length, the protein(s) encoded the gene, and one or more ligands of the encoded protein.

In some forms, the barcode is associated with metadata describing the digital information contained in a DNA sequence contained in the nucleic acid memory object. In some forms, the nucleic acid sequence encodes information about an image or images, and the metadata barcode contains the amount of any given characteristic in the image, and where one or more point mutations of the barcode of are associated with varied amounts of that characteristic. In some forms, the characteristic of the image is the intensity of one or more colors. In some forms, the DNA sequence encodes a digital representation of an image or images, and the metadata barcode contains descriptions of objects in the image or images, where the mutations of the barcodes of claim 42 are associated with the likeness to the object.

The disclosed compositions and methods can be further understood through the following numbered paragraphs.

1. A method for synthesizing a biopolymer having a desired size and sequence in the absence of a template, the method comprising:
    (a) combining, on a microfluidic device, a droplet comprising a component initiation sequence with one or more droplets collectively comprising a component building block and an attachment catalyst to form a combined droplet,
    wherein the droplets comprising a component initiation sequence and each of the droplets collectively comprising the component building block and the attachment catalyst were, prior to the combining, at different locations on the microfluidic device, wherein one or more additional droplets, each comprising an additional component building block, are at different locations on the microfluidic device than the droplet comprising the component sequence, the droplets collectively comprising the component building block and the attachment catalyst, or the combined droplet, wherein the combining comprises conditions suitable for the attachment catalyst to attach the component initiation sequence to the component building block to form a biopolymer; and (b) optionally repeating step (a) to perform the step-wise addition of component building blocks to the biopolymer to form a biopolymer having a preselected, desired polymer sequence and length.

2. The method of paragraph 1, wherein the conditions suitable for the attachment of the component initiation sequence with the component building block to form a biopolymer in step (a) comprise contacting the combined droplet with one or more reagents selected from the group consisting of a wash reagent, a blocking reagent, and a stop reagent.

3. The method of paragraph 2, wherein each of the wash reagent, blocking reagent, and stop reagent are provided as independent droplets on the microfluidic device.

4. The method of paragraph 1, wherein the combining of droplets in step (a) is accomplished by moving one or more of the droplets on the microfluidic device using electrical charge provided by an optic fiber.

5. The method of any one of paragraphs 1-4, wherein the sequence of movement for each droplet on the microfluidic device to produce the desired polymer sequence is provided in the form of a computer-readable program.

6. The method of paragraph 1, wherein two or more biopolymers are simultaneously or consecutively synthesized at different locations of the same microfluidic device.

7. The method of paragraph 6, wherein the two or more biopolymers have different sequences, different sizes, or both different sequences and different sizes.

8. The method of paragraph 7, wherein each of the two or more synthesized biopolymers is synthesized and purified at a distinct location on the same microfluidic device.

9. The method of paragraph 8, wherein each of the two or more biopolymers comprises a unique address tag.

10. The method of any one of paragraphs 1-9, wherein the component initiation sequence is coupled to a stable support matrix.

11. The method of paragraph 10, wherein the support matrix is a bead.

12. The method of paragraph 11, wherein the bead is magnetic.

13. The method of any one of paragraphs 1-12, wherein the droplet is an aqueous droplet having a volume between one femtoliter (fl) and 100 microliters (µl), preferably between one picoliter (pl) and one nanoliter (nl).

14. The method of any one of paragraphs 1-13, wherein the creation, movement and combination of the droplets on the microfluidic device is controlled by a computer program.

15. The method of any one of paragraphs 1-14, further comprising (c) manipulating, purifying, or isolating the synthesized biopolymer on the microfluidic device.

16. The method of paragraph 15, wherein manipulating the synthesized biopolymer in step (c) comprises inducing one or more structural or functional changes in the biopolymer.

17. The method of paragraph 16, wherein isolating the synthesized biopolymer in step (c) comprises a complexity-reduction step.

18. The method of paragraph 17, wherein the complexity-reduction step includes isolating the synthesized biopolymer on the basis of one or more properties selected from the group consisting of mass, size, electrochemical charge, hydrophobicity, pH, melting temperature, conformation, and affinity for one or more ligands.

19. The method of paragraph 16, wherein manipulating the synthesized biopolymer in step (c) comprises incorporating into the biopolymer one or more labels selected from the group consisting of a dye, a fluorescent molecule, a radiolabel, an affinity tag, and a barcode.

20. The method of any one of paragraphs 1-19 further comprising, prior to step (a), forming one or more of the droplets comprising the component initiation sequence and the droplets collectively comprising the component building block and the attachment catalyst by splitting the droplets from reservoirs that collectively comprise the component initiation sequence, the component building block, and the attachment catalyst.

21. The method of paragraph 20 further comprising, prior to step (a), forming one or more of the additional droplets by splitting the additional droplets from reservoirs that collectively comprise the additional component building blocks.

22. The method of any one of paragraphs 1-21, wherein the biopolymer is a nucleic acid.

23. The method of paragraph 22, wherein the nucleic acid has a length of between 100 and 100,000 bases in length, between 200 and 10,000 bases in length, between 500 and 5,000 bases, or between 1,000 and 3,000 bases in length.

24. The method of paragraph 22 or 23, wherein one or more of the component building blocks is selected from the group consisting of adenosine, cytidine, guanosine, thymidine, uridine, inosine, uridine, xanthosine, and pseudouridine.

25. The method of paragraph 23, wherein the nucleic acid is single-stranded DNA.

26. The method of any one of paragraphs 22-25, wherein the attachment catalyst is a polymerase enzyme selected from the group consisting of TdT, Qbeta replicase, and telomerase.

27. The method of any one of paragraphs 22-26, wherein step (c) comprises the polymerase chain reaction to amplify the synthesized nucleic acid.

28. The method of any one of paragraphs 22-27, further comprising the step of sequencing the synthesized nucleic acid.

29. The method of any one of paragraphs 22-27, wherein one or more droplets comprises a restriction endonuclease and one or more suitable buffers for the effective function of the restriction endonuclease.

30. A method for the automated manipulation of a nucleic acid sequence comprising combining, on a microfluidic device, the nucleic acid sequence and one or more endonuclease or exonuclease enzymes, wherein the combining comprises conditions under which the one or more endonuclease or exonuclease enzymes remove or degrade one or more nucleotides from the nucleic acid sequence to produce a degraded nucleic acid.

31. The method of paragraph 30, wherein the nucleic acid is immobilized on a solid support or surface.

32. The method of paragraph 30 or 31, further comprising purifying the degraded nucleic acid.

33. The method of paragraph 32, wherein purifying the degraded nucleic acid comprises washing the degraded nucleic acid on the microfluidic device to remove the one or more endonuclease or exonuclease enzymes.

34. The method of any one of paragraphs 30 to 33, further comprising adding one or more nucleotides to the degraded nucleic acid on the microfluidic device, to form a modified nucleic acid.

35. The method of paragraph 34, wherein adding one or more nucleotides to the degraded nucleic acid comprises:
(a) combining, on the microfluidic device, a droplet comprising the degraded nucleic acid with one or more droplets collectively comprising a component building block and an attachment catalyst to form a combined droplet,
wherein the droplets comprising the degraded nucleic acid and each of the droplets collectively comprising the component building block and the attachment catalyst were, prior to the combining, at different locations on the microfluidic device,
wherein the combining comprises conditions suitable for the attachment catalyst to attach the degraded nucleic to the component building block to form a modified nucleic acid; and
(b) optionally repeating step (a) one or more times.

36. The method of any one of paragraphs 30 to 35, wherein the nucleic acid is encodes bitstream data.

37. The method of any one of paragraphs 30 to 36, wherein the manipulation is carried out in a region of the nucleic acid that is a barcode.

38. The method of any one of paragraphs 1 to 37, wherein the microfluidic device is an electrowetting on dielectric (EWOD) device.

39. The method of any one of paragraphs 22 or 23, wherein the nucleic acid is a barcode.

40. The method of paragraph 39, wherein the barcode is attached to a nucleic acid memory object.

41. The method of any one of paragraphs 39 or 40, wherein the barcode is not the exact sequence of the barcode associated to the concept or metadata, but it mutated away from the barcode by 1, 2, 3, 4, 5, 6, 7, 8, 9, 10, 11, 12, 13, 14, 15, 16, 17, 18, 19, 20, 21, 22, 23, 24, 25, or more than 25 mutations.

42. The method of paragraph 41, wherein the mutated barcode is associated with metadata or a concept of the nearest barcode held in a barcode hash table associating to metadata contained within the nucleic acid memory object.

43. The method of paragraph 41, wherein the mutated barcode is associated with variations of metadata or a concept of the nearest barcode held in a barcode hash table.

44. The method of any one of paragraphs 39-43, wherein the barcode is associated with metadata describing biological information of the nucleic acid sequence contained in the nucleic acid memory object.

45. The method of paragraph 44, wherein the nucleic acid sequence is encapsulated within a nucleic acid memory object, wherein the nucleic acid memory object encodes a gene, and the barcode sequence describes one or more features selected from the group consisting of gene name, mutations of the gene, the source organism, gene length, the protein(s) encoded the gene, and one or more ligands of the encoded protein.

46. The method of any one of paragraphs 39-43, wherein the barcode is associated with metadata describing the digital information contained in a DNA sequence contained in the nucleic acid memory object.

47. The method of paragraph 46, wherein the nucleic acid sequence encodes information about an image or images, and the metadata barcode contains the amount of any given characteristic in the image, and wherein one or more point mutations of the barcode of are associated with varied amounts of that characteristic.

48. The method of paragraph 47, wherein the characteristic of the image is the intensity of one or more colors.

49. The method of paragraph 46, wherein the DNA sequence encodes a digital representation of an image or images, and the metadata barcode contains descriptions of objects in the image or images, wherein the mutations of the barcodes of paragraph 42 are associated with the likeness to the object.

The present invention will be further understood by reference to the following non-limiting examples.

EXAMPLES

Example 1: Echo-Based Synthesis of Nucleic Acids in Solution

A destination 96-well plate was loaded with 3×16 wells containing 10 μM tdt polymerase from New England Biolabs in 1×tdt buffer supplied with the reagent and an initiator sequence (GTCGTCGTCCCCTCAAACT) (SEQ ID NO: 22) at 1 μM. 16 numbers were chosen for conversion to nucleotide sequences by using single-precision IEEE 754 binary code (pi, e, gravitational constant, Avagadro's number, Planck's constant, SI electron volt, electron mass, proton mass, golden ratio, permittivity of free space, square root of 2, fine structure constant, hydrogen frequency, Boltzmann constant, $1,000,000^{th}$ prime number, and a test sequence). The binary representation was then converted to nucleotide sequences by a Huffman coding scheme to allow for the data to be encoded in the nucleotide switch, such that A>T, T>C, and C>A homopolymer stretches were encoded 1, and A>C, T>A, and C>T homopolymer stretches were encoding for 0.

The sequences were then converted to a cherry pick list with nucleotides being loaded into the source plate of an Echo 555 (LabCyte) and distributed to the well that contains the sequence encoding the number, in triplicated. After each distribution for the wells, the destination plate was removed and placed in a 37 C incubator for 15 minutes in high humidity. Samples were removed after every 4 homopolymer stretches that were taken for gel analysis on a 10% polyacrylamide gel stained with SybrGold (ThermoFisher). The sequences were poly(A) tailed by addition of dATP as the final nucleotide. The second strand was completed by 4 cycles with PCR with a poly(T) oligonucleotide primer, and size purified to enrich around 500 nucleotide length products.

The products were prepped for Illumina MiSeq 500×2 sequencing and the sequences were compiled to read out the encoded numbers.

Example 2: Developing Neighborhood Molecular Hash Barcodes

Two oligonucleotide primers were selected from a list of 240,000 known orthogonal primers (Xu, et al., *Proc Natl Acad Sci*, 106 (7) 2289-2294 (2009)). Pseudo-random mutations were generated for each of the primers such that the mutations were predicted to raise the binding energy by approximately 20 kJ/mol, or approximately 5° C., with calculations made by the ΔH and ΔS, when known.

Pseudo-random mutations that lowered too much or not enough were removed. Those primers that remained were mutated again with the same binding energy constraint, until the list was pared down to an ordered list of 11 primers with binding energies between adjacent primers destabilized by 20 kJ/mol relative to binding energy between primers and their exact complements. These binding energies between a barcode-complement pair were chosen to be destabilized by an amount proportional to their distance from each other in the list of all possible qualifying primers. Each of the two original primers produced an ordered list of 10 primer mutants, plus the original primer. These primer neighborhoods were associated with two arbitrary metadata terms ("Red" and "Blue") for description of images that are encoded in DNA sequences. The prescribed binding affinity relationship was verified experimentally with a melting temperature assay. A 384-well plate was generated with 10 mM Tris-HCl pH 8.1, 150 mM NaCl, 1 mM EDTA, and 2 µM per oligo of each possible primer-complement pair between "Red" primers and "Red" and "Blue" complements. 1×SybrGreen was added and a QuantStudio 6 was used to assay the melting temperature by imaging during a temperature ramp (annealing from 95° C. to 25° C. and melting 25° C. to 95° C., and repeating).

The melting temperature was calculated based on the inflection point of the melting curve, and these data plotted as a heat map. Perfect capture was shown as a high melting temperature, while imperfect capture was seen as a low melting temperature. Each temperature of melting was associated to the barcode pair in a matrix and a heatmap was generated.

The heatmap showed the expected results, with a high melting temperature along the diagonal of the red-like to red-like-complement strands, and a falling melting temperature with each successive mutation along both axes, while no specific binding was shown between the red barcodes and blue barcodes. For comparison, a computational heatmap was generated by using the Santa-Lucia thermodynamic values, showing a high correlation with the experimental results.

To validate the quantitative PCR melting experiment, UV/Vis monitoring absorbance at 260 nm over the same temperature range was used to determine the melting temperature. This was applied to the middle strand (50% "Red"-like barcode) against the other "Red"-like complementary strands. The results of the melting experiment showed excellent agreement with the values from the quantitative PCR melting program. Thus, it was possible to predict "neighborhoods" of controlled sequence for orthogonal barcoding with programmed noisy crosstalk.

Example 3: Barcode Selection by Fluorescent Bait Sequences

Fluorescent barcodes were purchased from IDT with sequences complementary to 3 barcodes chosen from the list of 240,000 orthogonal barcodes (Xu, et al., *Proc Natl Acad Sci,* 106 (7) 2289-2294 (2009)), associated in an external table to be encoding "cat", "wild", and "orange". 3 images of house cats (1 black and white, one brown, one orange) and a tiger and a lion, and 2 house dogs (1 retriever, 1 greyhound) and a wolf were encoded as 27×27 black and white images and converted to DNA encoding after compression (run-length-encoding) and encryption of the bitmap image.

The DNA sequences were put into plasmid form and encapsulated in silica as described above with methods in International Publication No. WO 2017/189914.

The plasmids were barcoded with metadata tags such that approximately 1,000 redundant barcode overhangs are present on each of the blocks encoding the images.

10× molar excess of the fluorescent strand was added to the barcoded material and annealed at the predicted melting temperature. The unbound fraction was washed using 30 mM Tris HCl pH 8.1 and 150 mM NaCl in multiple wash steps.

The barcoded images can be tested by fluorescence microscopy and fluorescent sorting, enabling rapid sorting using biochemical barcoding of plasmids and also digital information.

We claim:

1. A method for synthesizing a biopolymer having a user-defined sequence of component building blocks on a microfluidic system, the method comprising:
   (a) forming, on a microfluidic device, first, second, and third droplets, wherein the microfluidic device comprises:
      (i) a multiplicity of spatially distinct addressed locations;
      (ii) a multiplicity of distinct fluid reservoirs; and
      (iii) a microfluidic handling system that can actuate (1) splitting of droplets from each of the multiplicity of reservoirs through motive force induced by electric potential or optical excitation at the fluid reservoirs, and (2) movement of droplets from each of the addressed locations to another of the addressed locations through motive force induced by electric potential or optical excitation at the addressed locations,
      wherein each of the multiplicity of fluid reservoirs is located at a spatially distinct addressed location on the microfluidic device,
      wherein a first of the multiplicity of fluid reservoirs comprises a solution comprising a component initiation sequence,
      wherein a second of the multiplicity of fluid reservoirs comprises a solution comprising a first component building block,
      wherein a third of the multiplicity of fluid reservoirs comprises a solution comprising an attachment catalyst that can catalyze the attachment of the component building block to the component initiation sequence and/or a further component building block, and
      optionally wherein a fourth or further of the multiplicity of fluid reservoirs comprises a solution comprising a further component building block;
      wherein the first droplet comprises a component initiation sequence,
      wherein the first droplet is formed by splitting from the first reservoir,
      wherein the second droplet comprises a first component building block,
      wherein the second droplet is formed by splitting from the second reservoir,
      wherein the third droplet comprises an attachment catalyst,
      wherein the third droplet is formed by splitting from the third fluid reservoir,
      wherein the splitting comprises moving a droplet of fluid away from a fluid reservoir, and
      wherein each of the droplets is formed at a distinct addressed location on the microfluidic device;
   (b) combining the first, second, and third droplets to form a combined droplet,
      wherein the combining comprises moving each of the droplets to the same addressed location on the microfluidic device,
      wherein the combining is performed under conditions suitable for the attachment catalyst to attach the component initiation sequence to the first component building block within the combined droplet;

(c) forming, on the microfluidic device, a further droplet comprising a component building block, wherein forming the further droplet comprises splitting a droplet from the second, or fourth or further reservoir, and optionally forming an additional droplet comprising an attachment catalyst, wherein forming the additional droplet comprises splitting a droplet from the third reservoir;

(d) combining the combined droplet with the further droplet and, optionally, with the additional droplet, to synthesize a biopolymer, wherein the combining comprises moving the further droplet and/or the combined droplet and, optionally, the additional droplet, to the same addressed location, and wherein the combining is performed under conditions suitable for the attachment catalyst to attach the component building block from the further droplet to the component building block within the combined droplet;

(e) optionally repeating steps (c) and (d) one or more times to perform step wise addition of component building blocks to the biopolymer; and (f) manipulating, purifying, or isolating the synthesized biopolymer on the microfluidic device, wherein the sequence of the synthesized biopolymer is defined by the order in which droplets comprising component building blocks are combined with the combined droplet, and wherein the order in which the droplets are combined is controlled by the user.

2. The method of claim 1, further comprising in step (b) contacting the combined droplet with one or more reagents selected from the group consisting of a wash reagent, a blocking reagent, and a stop reagent.

3. The method of claim 2, wherein each of the wash reagent, blocking reagent, and stop reagent are provided as independent droplets on the microfluidic device.

4. The method of claim 1, wherein the combining of droplets in step (b) is accomplished by moving one or more of the droplets on the microfluidic device using electrical charge provided by an optic fiber.

5. The method of claim 1, wherein the microfluidic handling system is operably connected with a computer, and
wherein the splitting of droplets and movement of droplets is controlled by the user through an interface with the computer.

6. The method of claim 5, wherein the control by the user of the splitting of each droplet and the movement of each droplet on the microfluidic device to produce the biopolymer is provided by the user to the computer in the form of a computer-readable program.

7. The method of claim 1, wherein two or more biopolymers are simultaneously or consecutively synthesized at different locations of the same microfluidic device.

8. The method of claim 7, wherein the two or more biopolymers have different sequences, different sizes, or both different sequences and different sizes.

9. The method of claim 8, wherein each of the two or more synthesized biopolymers is synthesized and purified at a distinct location on the same microfluidic device.

10. The method of claim 9, wherein each of the two or more biopolymers comprises a unique address tag.

11. The method of claim 1, wherein the component initiation sequence is coupled to a stable support matrix.

12. The method of claim 11, wherein the support matrix is a bead.

13. The method of claim 12, wherein the bead is magnetic.

14. The method of claim 1, wherein the droplets are aqueous droplets having a volume between one femtoliter (fl) and 100 microliters (µl).

15. The method of claim 5, wherein the formation, movement and combination of the droplets on the microfluidic device is controlled by a computer program.

16. The method of claim 1, wherein manipulating the synthesized biopolymer in step (f) comprises inducing one or more structural or functional changes in the biopolymer.

17. The method of claim 16, wherein isolating the synthesized biopolymer in step (f) comprises a complexity-reduction step.

18. The method of claim 17, wherein the complexity-reduction step includes isolating the synthesized biopolymer on the basis of one or more properties selected from the group consisting of mass, size, electrochemical charge, hydrophobicity, pH, melting temperature, conformation, and affinity for one or more ligands.

19. The method of claim 16, wherein manipulating the synthesized biopolymer in step (f) comprises incorporating into the biopolymer one or more labels selected from the group consisting of a dye, a fluorescent molecule, a radio-label, an affinity tag, and a barcode.

20. The method of claim 1 further comprising, prior to step (a), forming one or more further droplets by splitting the further droplets from reservoirs that comprise further component building blocks.

21. The method of claim 1, wherein the biopolymer is a nucleic acid.

22. The method of claim 21, wherein the nucleic acid has a length of between 100 and 100,000 bases in length, between 200 and 10,000 bases in length, between 500 and 5,000 bases, or between 1,000 and 3,000 bases in length.

23. The method of claim 21, wherein one or more of the component building blocks is selected from the group consisting of adenosine, cytidine, guanosine, thymidine, uridine, inosine, uridine, xanthosine, and pseudouridine.

24. The method of claim 22, wherein the nucleic acid is single-stranded DNA.

25. The method of claim 21, wherein the attachment catalyst is a polymerase enzyme selected from the group consisting of TdT, Qbeta replicase, and telomerase.

26. The method of claim 21, wherein step (f) comprises a polymerase chain reaction to amplify the synthesized nucleic acid.

27. The method of claim 21, further comprising a step of sequencing the synthesized nucleic acid.

28. The method of claim 21, wherein one or more droplets comprises a restriction endonuclease and one or more suitable buffers for the effective function of the restriction endonuclease.

29. The method of claim 1, wherein the microfluidic device is an electrowetting on dielectric (EWOD) device.

30. The method of claim 21, wherein the nucleic acid is a barcode.

31. The method of claim 30, wherein the barcode is attached to a nucleic acid memory object.

32. The method of claim 30, wherein the barcode is not the exact sequence of the barcode associated to the concept or metadata, but it mutated away from the barcode by 1, 2, 3, 4, 5, 6, 7, 8, 9, 10, 11, 12, 13, 14, 15, 16, 17, 18, 19, 20, 21, 22, 23, 24, 25, or more than 25 mutations.

33. The method of claim 32, wherein the mutated barcode is associated with metadata or a concept of the nearest barcode held in a barcode hash table associating to metadata contained within the nucleic acid memory object.

34. The method of claim 32, wherein the mutated barcode is associated with variations of metadata or a concept of the nearest barcode held in a barcode hash table.

35. The method of claim 30, wherein the barcode is associated with metadata describing biological information of the nucleic acid sequence contained in the nucleic acid memory object.

36. The method of claim 35, wherein the nucleic acid sequence is encapsulated within a nucleic acid memory object, wherein the nucleic acid memory object encodes a gene, and the barcode sequence describes one or more features selected from the group consisting of gene name, mutations of the gene, the source organism, gene length, the protein(s) encoded the gene, and one or more ligands of the encoded protein.

37. The method of claim 30, wherein the barcode is associated with metadata describing the digital information contained in a DNA sequence contained in the nucleic acid memory object.

38. The method of claim 37, wherein the nucleic acid sequence encodes information about an image or images, and the metadata barcode contains the amount of any given characteristic in the image, and wherein one or more point mutations of the barcode of are associated with varied amounts of that characteristic.

39. The method of claim 38, wherein the characteristic of the image is the intensity of one or more colors.

40. The method of claim 37, wherein the DNA sequence encodes a digital representation of an image or images, and the metadata barcode contains descriptions of objects in the image or images, wherein the mutations of the barcodes of claim 33 are associated with the likeness to the object.

41. The method of claim 1, wherein the droplets are aqueous droplets having a volume between one picoliter (pl) and one nanoliter (nl).

42. A method for synthesizing a biopolymer having a user-defined sequence of component building blocks on a microfluidic system, the method comprising:
   (a) forming, on a microfluidic device, a first and second droplets, wherein the microfluidic device comprises:
      (i) a multiplicity of spatially distinct addressed locations;
      (ii) a multiplicity of distinct fluid reservoirs; and
      (iii) a microfluidic handling system that can actuate (1) splitting of droplets from each of the multiplicity of reservoirs through motive force induced by electric potential or optical excitation at the fluid reservoirs, and (2) movement of droplets from each of the addressed locations to another of the addressed locations through motive force induced by electric potential or optical excitation at the addressed locations,
   wherein each of the multiplicity of fluid reservoirs is located at a spatially distinct addressed location on the microfluidic device,
   wherein a first of the multiplicity of fluid reservoirs comprises a solution comprising a component initiation sequence,
   wherein a second of the multiplicity of fluid reservoirs comprises
      (i) a component building block; and
      (ii) an attachment catalyst that can catalyze the attachment of the component building block to the component initiation sequence and/or another component building block;
   optionally wherein a third or further of the multiplicity of fluid reservoirs comprises
      (i) a solution comprising a component building block; and
      (ii) an attachment catalyst that can catalyze the attachment of the component building block to the component initiation sequence and/or another component building block;
   wherein the first droplet comprises a component initiation sequence and is formed by splitting from the first of the multiplicity of fluid reservoirs,
   wherein the second droplet comprises a component building block and an attachment catalyst and is formed by splitting from the second of the multiplicity of fluid reservoirs,
   wherein the splitting comprises moving a droplet of fluid away from a fluid reservoir, and
   wherein each of the droplets is formed at a distinct addressed location on the microfluidic device;
   (b) combining the first and second droplets to form a combined droplet,
   wherein the combining comprises moving each of the droplets to the same addressed location on the microfluidic device,
   wherein the combining is performed under conditions suitable for the attachment catalyst to attach the component initiation sequence to the component building block within the combined droplet;
   (c) forming, on the microfluidic device, a third or further droplet comprising a component building block and attachment catalyst,
   wherein forming the further droplet comprises splitting a droplet from the second, third, or further of the multiplicity of fluid reservoirs;
   (d) combining the combined droplet with the third or further droplet to synthesize a biopolymer,
   wherein the combining comprises moving the further droplet and/or the combined droplet to the same addressed location, and
   wherein the combining is performed under conditions suitable for the attachment catalyst to attach the component building block from the third droplet to the component building block within the combined droplet;
   (e) optionally repeating steps (c) and (d) one or more times to perform step wise addition of component building blocks to the biopolymer; and
   (f) manipulating, purifying, or isolating the synthesized biopolymer on the microfluidic device,
   wherein the sequence of the synthesized biopolymer is defined by the order in which droplets comprising component building blocks are combined with the combined droplet, and
   wherein the order in which the droplets are combined is controlled by the user.

43. The method of claim 42, wherein the second of the multiplicity of fluid reservoirs comprises a first species of component building block, and
   wherein the third of the multiplicity of fluid reservoirs comprises a second species of component building block.

* * * * *

UNITED STATES PATENT AND TRADEMARK OFFICE
CERTIFICATE OF CORRECTION

| | | |
|---|---|---|
| PATENT NO. | : 11,851,651 B2 | |
| APPLICATION NO. | : 16/012583 | |
| DATED | : December 26, 2023 | |
| INVENTOR(S) | : James Banal et al. | |

It is certified that error appears in the above-identified patent and that said Letters Patent is hereby corrected as shown below:

In the Claims

Claim 32, Column 94, Lines 60 and 61, replace "the barcode associated to the concept or metadata, but it mutated" with --a barcode associated to a concept or metadata but is mutated--

Claim 33, Column 94, Line 67, replace "the nucleic acid memory object" with --a nucleic acid memory object--

Claim 35, Column 95, Lines 6 and 7, replace "the nucleic acid memory object" with --a nucleic acid memory object--

Claim 36, Column 95, Line 14, replace "encoded the gene" with --encoded by the gene--

Claim 37, Column 95, Line 17, replace "describing the digital" with --describing digital--

Claim 37, Column 95, Lines 18 and 19, replace "the nucleic acid memory object" with --a nucleic acid memory object--

Claim 38, Column 95, Line 24, replace "barcode of are" with --barcode are--

Claim 40, Column 95, Lines 31 and 32, replace "the mutations of the barcodes of claim 33 are" with --mutation of the barcode is--

Signed and Sealed this
Twenty-third Day of April, 2024

Katherine Kelly Vidal
*Director of the United States Patent and Trademark Office*